United States Patent
Kourtis et al.

(10) Patent No.: US 11,015,016 B2
(45) Date of Patent: *May 25, 2021

(54) POLYMERIC ADHESIVE FOR ANCHORING COMPLIANT MATERIALS TO ANOTHER SURFACE

(71) Applicant: Hyalex Orthopaedics, Inc., Lexington, MA (US)

(72) Inventors: Lampros Kourtis, Cambridge, MA (US); David Myung, San Jose, CA (US); Daniel Chang, Danville, CA (US); Bing Yu, Berkeley, CA (US); Timothy Sun, Berkeley, CA (US); Michael J. Jaasma, San Francisco, CA (US); Vernon Hartdegen, Collierville, TN (US)

(73) Assignee: Hyalex Orthopaedics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/688,351

(22) Filed: Nov. 19, 2019

(65) Prior Publication Data

US 2020/0087440 A1 Mar. 19, 2020

Related U.S. Application Data

(63) Continuation of application No. 15/668,547, filed on Aug. 3, 2017, now Pat. No. 10,519,270, which is a (Continued)

(51) Int. Cl.
*A61F 2/30* (2006.01)
*A61K 47/32* (2006.01)
(Continued)

(52) U.S. Cl.
CPC .......... *C08G 18/6229* (2013.01); *A61F 2/30* (2013.01); *A61K 47/32* (2013.01); *A61L 24/001* (2013.01);
(Continued)

(58) Field of Classification Search
None
See application file for complete search history.

(56) References Cited

U.S. PATENT DOCUMENTS 3,030,327 A 4/1962 Hosch
3,053,251 A 9/1962 Black et al.
(Continued)

FOREIGN PATENT DOCUMENTS

EP 0674888 A1 10/1995
EP 0994911 B1 8/2003
(Continued)

OTHER PUBLICATIONS

Barszczewska-Rybarek, Izabela M.; Quantitative determination of degree of conversion in photocured poly (urethane-dimethacrylate)s by Fourier transform infrared spectroscopy; Journal of Applied Polymer Science; vol. 123; issue 3; pp. 1604-1611; Feb. 5, 2012.
(Continued)

*Primary Examiner* — Peter A Salamon
(74) *Attorney, Agent, or Firm* — Clark & Elbing LLP

(57) ABSTRACT

Methods, compositions, and kits for adhering polymers and other materials to another material, and in particular to bone or bone-like structures or surfaces. A composition of matter includes a urethane dimethacrylate-methyl methacrylate copolymer with a plurality of first polymer regions based on urethane dimethacrylate and a plurality of second polymer regions based on methyl methacrylate. The method includes placing an orthopedic joint implant having an attachment surface in a joint space, applying a first non-urethane-
(Continued)

containing precursor, a second urethane-containing precursor, and a initiator to the attachment surface; contacting the first and second precursors and the initiator with the joint surface; and copolymerizing the first and second precursors and forming an adhesive copolymer and attaching the implant to the joint.

20 Claims, 26 Drawing Sheets

Related U.S. Application Data continuation of application No. 14/877,884, filed on Oct. 7, 2015, now Pat. No. 9,750,842, which is a continuation of application No. 13/573,788, filed on Oct. 3, 2012, now abandoned.

(60) Provisional application No. 61/672,203, filed on Jul. 16, 2012, provisional application No. 61/542,740, filed on Oct. 3, 2011.

(51) Int. Cl.
  C08G 18/62 (2006.01)
  C08G 18/48 (2006.01)
  C08G 18/65 (2006.01)
  C08G 18/67 (2006.01)
  C08G 18/32 (2006.01)
  C09J 4/06 (2006.01)
  C09J 135/02 (2006.01)
  C08L 33/08 (2006.01)
  C08L 33/12 (2006.01)
  F01D 5/08 (2006.01)
  F01D 11/02 (2006.01)
  F01D 11/00 (2006.01)
  A61M 5/19 (2006.01)
  B65D 85/00 (2006.01)
  C09J 133/14 (2006.01)
  A61L 24/06 (2006.01)
  A61L 24/00 (2006.01)
  A61L 24/04 (2006.01)
  C08G 18/72 (2006.01)
  C08G 81/02 (2006.01)
  A61B 17/56 (2006.01)

(52) U.S. Cl.
  CPC ......... *A61L 24/0015* (2013.01); *A61L 24/043* (2013.01); *A61L 24/06* (2013.01); *A61M 5/19* (2013.01); *B65D 85/70* (2013.01); *C08G 18/3206* (2013.01); *C08G 18/4854* (2013.01); *C08G 18/6511* (2013.01); *C08G 18/6705* (2013.01); *C08G 18/728* (2013.01); *C08G 81/024* (2013.01); *C08L 33/08* (2013.01); *C08L 33/12* (2013.01); *C09J 4/06* (2013.01); *C09J 133/14* (2013.01); *C09J 135/02* (2013.01); *F01D 5/082* (2013.01); *F01D 11/001* (2013.01); *F01D 11/025* (2013.01); *A61B 17/56* (2013.01); *A61L 2300/406* (2013.01); *A61L 2430/24* (2013.01); *F05D 2240/57* (2013.01); *F05D 2260/14* (2013.01)

(56) References Cited

U.S. PATENT DOCUMENTS

| | | |
|---|---|---|
| 3,702,611 A | 11/1972 | Fishbein |
| 3,826,678 A | 7/1974 | Hoffman et al. |
| 3,833,404 A | 9/1974 | Sperling et al. |
| 3,873,640 A | 3/1975 | Owston et al. |
| 3,939,049 A | 2/1976 | Ratner et al. |
| 4,035,848 A | 7/1977 | Wagner |
| 4,107,386 A | 8/1978 | Gruber et al. |
| 4,128,600 A | 12/1978 | Skinner et al. |
| 4,192,827 A | 3/1980 | Mueller et al. |
| 4,224,699 A | 9/1980 | Weber |
| 4,302,553 A | 11/1981 | Frisch et al. |
| 4,312,079 A | 1/1982 | Dorre et al. |
| 4,320,709 A | 3/1982 | Hladun |
| 4,391,797 A | 7/1983 | Folkman et al. |
| 4,423,099 A | 12/1983 | Mueller et al. |
| 4,431,787 A | 2/1984 | Werber |
| 4,439,583 A | 3/1984 | Gould et al. |
| 4,452,925 A | 6/1984 | Kuzma et al. |
| 4,468,499 A | 8/1984 | Siegfried et al. |
| 4,477,604 A | 10/1984 | Oechsle, III |
| 4,487,865 A | 12/1984 | Balazs et al. |
| 4,500,676 A | 2/1985 | Balazs et al. |
| 4,502,161 A | 3/1985 | Wall |
| 4,536,554 A | 8/1985 | Lim et al. |
| 4,575,539 A | 3/1986 | DeCrosta et al. |
| 4,621,637 A | 11/1986 | Fishbein |
| 4,657,941 A | 4/1987 | Blackwell et al. |
| 4,678,468 A | 7/1987 | Hiroyoshi |
| 4,680,336 A | 7/1987 | Larsen et al. |
| 4,693,715 A | 9/1987 | Abel, Jr. |
| 4,693,721 A | 9/1987 | Ducheyne |
| 4,816,495 A | 3/1989 | Blackwell et al. |
| 4,836,884 A | 6/1989 | McAuslan |
| 4,846,841 A | 7/1989 | Oh |
| 4,865,601 A | 9/1989 | Caldwell et al. |
| 4,913,144 A | 4/1990 | Del Medico |
| 4,931,287 A | 6/1990 | Bae et al. |
| 4,966,934 A | 10/1990 | Huang et al. |
| 4,973,493 A | 11/1990 | Guire |
| 4,978,352 A | 12/1990 | Fedorov et al. |
| 5,030,230 A | 7/1991 | White |
| 5,061,270 A | 10/1991 | Aboczky |
| 5,067,961 A | 11/1991 | Kelman et al. |
| 5,087,392 A | 2/1992 | Burke et al. |
| 5,091,205 A | 2/1992 | Fan |
| 5,094,876 A | 3/1992 | Goldberg et al. |
| 5,100,689 A | 3/1992 | Goldberg et al. |
| 5,112,350 A | 5/1992 | Civerchia et al. |
| 5,115,056 A | 5/1992 | Mueller et al. |
| 5,122,133 A | 6/1992 | Evans |
| 5,133,769 A | 7/1992 | Wagner et al. |
| 5,171,318 A | 12/1992 | Gibson et al. |
| 5,180,756 A | 1/1993 | Rehmer et al. |
| 5,258,024 A | 11/1993 | Chavel et al. |
| 5,264,495 A | 11/1993 | Irie et al. |
| 5,276,070 A | 1/1994 | Arroyo |
| 5,282,851 A | 2/1994 | Jacob-LaBarre |
| 5,290,548 A | 3/1994 | Goldberg et al. |
| 5,300,116 A | 4/1994 | Chirila et al. |
| 5,314,478 A | 5/1994 | Oka et al. |
| 5,374,515 A | 12/1994 | Parenteau et al. |
| 5,403,893 A | 4/1995 | Tanaka et al. |
| 5,412,049 A | 5/1995 | Argyropoulos et al. |
| 5,476,515 A | 12/1995 | Kelman et al. |
| 5,519,071 A | 5/1996 | Rheinberger et al. |
| 5,554,665 A | 9/1996 | Tateosian et al. |
| 5,556,429 A | 9/1996 | Felt |
| 5,562,738 A | 10/1996 | Boyd et al. |
| 5,576,072 A | 11/1996 | Hostettler et al. |
| 5,587,406 A | 12/1996 | Yamamoto et al. |
| 5,589,563 A | 12/1996 | Ward et al. |
| 5,591,170 A | 1/1997 | Spievack et al. |
| 5,643,390 A | 7/1997 | Don et al. |
| 5,644,049 A | 7/1997 | Giusti et al. |
| 5,645,592 A | 7/1997 | Nicolais et al. |
| 5,656,210 A | 8/1997 | Hill et al. |
| 5,660,692 A | 8/1997 | Nesburn et al. |
| 5,674,942 A | 10/1997 | Hill et al. |
| 5,693,034 A | 12/1997 | Buscemi et al. |
| 5,716,633 A | 2/1998 | Civerchia |
| 5,733,289 A | 3/1998 | Seedhom et al. |
| 5,763,529 A | 6/1998 | Lucas |

(56) References Cited

U.S. PATENT DOCUMENTS

| | | |
|---|---|---|
| 5,770,669 A | 6/1998 | Robertson et al. |
| 5,773,485 A | 6/1998 | Bennett et al. |
| 5,800,412 A | 9/1998 | Zhang et al. |
| 5,824,079 A | 10/1998 | Siegler et al. |
| 5,834,532 A | 11/1998 | Yamamoto et al. |
| 5,836,313 A | 11/1998 | Perez et al. |
| 5,837,752 A | 11/1998 | Shastri et al. |
| 5,856,366 A | 1/1999 | Shiveley et al. |
| 5,904,927 A | 5/1999 | Amiji |
| 5,913,858 A | 6/1999 | Calandruccio et al. |
| 5,962,005 A | 10/1999 | Saga et al. |
| 5,976,648 A | 11/1999 | Li et al. |
| 5,977,199 A | 11/1999 | Xie |
| 6,001,894 A | 12/1999 | Ottersbach et al. |
| 6,005,160 A | 12/1999 | Hsiue et al. |
| 6,019,766 A | 2/2000 | Ling et al. |
| 6,027,742 A | 2/2000 | Lee et al. |
| 6,030,606 A | 2/2000 | Holmes |
| 6,031,017 A | 2/2000 | Waki et al. |
| 6,057,406 A | 5/2000 | Pojman et al. |
| 6,071,983 A | 6/2000 | Yamamoto et al. |
| 6,096,842 A | 8/2000 | Friese et al. |
| 6,120,904 A | 9/2000 | Hostettler et al. |
| 6,160,084 A | 12/2000 | Langer et al. |
| 6,171,300 B1 | 1/2001 | Adams |
| 6,210,438 B1 | 4/2001 | Sheets, Jr. et al. |
| 6,214,044 B1 | 4/2001 | Silverstrini |
| 6,221,467 B1 | 4/2001 | Nazarova et al. |
| 6,224,893 B1 | 5/2001 | Langer et al. |
| 6,231,605 B1 | 5/2001 | Ku |
| 6,231,611 B1 | 5/2001 | Mosseri |
| 6,239,209 B1 | 5/2001 | Yang et al. |
| 6,251,965 B1 | 6/2001 | Wang et al. |
| 6,254,637 B1 | 7/2001 | Lee et al. |
| 6,262,163 B1 | 7/2001 | Weitzel et al. |
| 6,264,695 B1 | 7/2001 | Stoy |
| 6,265,016 B1 | 7/2001 | Hostettler et al. |
| 6,281,271 B1 | 8/2001 | Rumphorst et al. |
| 6,306,177 B1 | 10/2001 | Felt et al. |
| 6,306,424 B1 | 10/2001 | Vyakarnam et al. |
| 6,312,799 B1 | 11/2001 | Hosokawa et al. |
| 6,331,578 B1 | 12/2001 | Turner et al. |
| 6,368,315 B1 | 4/2002 | Gillis et al. |
| 6,372,815 B1 | 4/2002 | Sulc et al. |
| 6,376,742 B1 | 4/2002 | Zdrahala et al. |
| 6,388,043 B1 | 5/2002 | Langer et al. |
| 6,391,055 B1 | 5/2002 | Ikada et al. |
| 6,428,576 B1 | 8/2002 | Haldimann |
| 6,429,256 B1 | 8/2002 | Vandevoorde et al. |
| 6,437,018 B1 | 8/2002 | Gertzman et al. |
| 6,440,444 B2 | 8/2002 | Boyce et al. |
| 6,479,565 B1 | 11/2002 | Stanley |
| 6,482,209 B1 | 11/2002 | Engh et al. |
| 6,494,917 B1 | 12/2002 | McKellop et al. |
| 6,509,098 B1 | 1/2003 | Merrill et al. |
| 6,521,732 B2 | 2/2003 | Perez et al. |
| 6,585,771 B1 | 7/2003 | Buttermilch et al. |
| 6,610,067 B2 | 8/2003 | Tallarida et al. |
| 6,629,997 B2 | 10/2003 | Mansmann |
| 6,632,235 B2 | 10/2003 | Weikel et al. |
| 6,632,246 B1 | 10/2003 | Simon et al. |
| 6,645,715 B1 | 11/2003 | Griffith et al. |
| 6,652,587 B2 | 11/2003 | Felt et al. |
| 6,673,079 B1 | 1/2004 | Kane |
| 6,673,112 B2 | 1/2004 | Nigam |
| 6,676,795 B1 | 1/2004 | Levandoski |
| 6,679,917 B2 | 1/2004 | Ek |
| 6,689,165 B2 | 2/2004 | Jacob et al. |
| 6,706,836 B1 | 3/2004 | Holguin et al. |
| 6,726,322 B2 | 4/2004 | Andino et al. |
| 6,733,533 B1 | 5/2004 | Lozier |
| 6,740,087 B2 | 5/2004 | Knox |
| 6,755,865 B2 | 6/2004 | Tarabishy |
| 6,759,449 B2 | 7/2004 | Kimura et al. |
| 6,787,584 B2 | 9/2004 | Jia et al. |
| 6,846,875 B2 | 1/2005 | Pennings et al. |
| 6,852,125 B2 | 2/2005 | Simon et al. |
| 6,866,936 B2 | 3/2005 | Opolski |
| 6,911,212 B2 | 6/2005 | Gertzman et al. |
| 6,918,914 B2 | 7/2005 | Bauer |
| 6,921,264 B2 | 7/2005 | Mayer et al. |
| 6,949,251 B2 | 9/2005 | Dalal et al. |
| RE38,839 E | 10/2005 | Magnante |
| 6,953,594 B2 | 10/2005 | Lee et al. |
| 6,955,540 B2 | 10/2005 | Mayer et al. |
| 6,960,617 B2 | 11/2005 | Omidian et al. |
| 6,976,997 B2 | 12/2005 | Noolandi et al. |
| 7,008,226 B2 | 3/2006 | Mayer et al. |
| 7,008,635 B1 | 3/2006 | Coury et al. |
| 7,018,460 B2 | 3/2006 | Xu et al. |
| 7,019,192 B2 | 3/2006 | Gertzman et al. |
| 7,029,479 B2 | 4/2006 | Tallarida et al. |
| 7,037,984 B2 | 5/2006 | Lendlein et al. |
| 7,049,351 B2 | 5/2006 | Phelan et al. |
| 7,066,958 B2 | 6/2006 | Ferree |
| 7,067,194 B2 | 6/2006 | Mao et al. |
| 7,083,650 B2 | 8/2006 | Moskowitz et al. |
| 7,094,286 B2 | 8/2006 | Liu |
| 7,105,026 B2 | 9/2006 | Johnson et al. |
| 7,160,305 B2 | 1/2007 | Schmieding |
| 7,163,541 B2 | 1/2007 | Ek |
| 7,173,074 B2 | 2/2007 | Mitra et al. |
| 7,176,247 B1 | 2/2007 | Walker, Jr. |
| 7,204,897 B2 | 4/2007 | Stoy et al. |
| 7,217,294 B2 | 5/2007 | Kusanagi et al. |
| 7,220,491 B2 | 5/2007 | Rouns et al. |
| 7,235,592 B2 | 6/2007 | Muratoglu et al. |
| 7,259,210 B2 | 8/2007 | Puckett, Jr. et al. |
| 7,279,174 B2 | 10/2007 | Pacetti et al. |
| 7,279,507 B2 | 10/2007 | Hu et al. |
| 7,279,508 B2 | 10/2007 | Bellare et al. |
| 7,303,814 B2 | 12/2007 | Lamberti et al. |
| 7,335,205 B2 | 2/2008 | Aeschlimann et al. |
| 7,341,593 B2 | 3/2008 | Auxepaules et al. |
| 7,371,257 B2 | 5/2008 | Sahatjian et al. |
| 7,387,810 B2 | 6/2008 | Hossainy |
| 7,452,924 B2 | 11/2008 | Aasen et al. |
| 7,468,075 B2 | 12/2008 | Lang et al. |
| 7,476,398 B1 | 1/2009 | Doillon et al. |
| 7,563,483 B2 | 7/2009 | Hossainy et al. |
| 7,618,462 B2 | 11/2009 | Ek |
| 7,659,324 B2 | 2/2010 | Moszner et al. |
| 7,678,151 B2 | 3/2010 | Ek |
| 7,713,305 B2 | 5/2010 | Ek |
| 7,824,666 B2 | 11/2010 | Wolff et al. |
| 8,076,389 B2 | 12/2011 | Rao et al. |
| 8,252,851 B2 | 8/2012 | Young et al. |
| 8,292,625 B2 | 10/2012 | Skaria et al. |
| 8,497,023 B2 | 7/2013 | Myung et al. |
| 8,501,834 B2 | 8/2013 | Maletz et al. |
| 8,679,190 B2 | 3/2014 | Myung et al. |
| 8,795,382 B2 | 8/2014 | Lin et al. |
| 8,816,029 B2 | 8/2014 | Wang et al. |
| 8,829,073 B2 | 9/2014 | Nies |
| 8,834,772 B2 | 9/2014 | Schindler et al. |
| 8,853,294 B2 | 10/2014 | Myung et al. |
| 8,883,915 B2 | 11/2014 | Myung et al. |
| 9,114,024 B2 | 8/2015 | Kourtis et al. |
| 9,333,149 B2 | 5/2016 | Lueck |
| 9,387,082 B2 | 7/2016 | Myung et al. |
| 9,387,275 B2 | 7/2016 | Vogt et al. |
| 9,750,842 B2 * | 9/2017 | Kourtis ............... C08G 18/728 |
| 10,457,803 B2 | 10/2019 | Myung et al. |
| 2001/0029399 A1 | 10/2001 | Ku |
| 2001/0044026 A1 | 11/2001 | Vaghefi et al. |
| 2002/0022884 A1 | 2/2002 | Mansmann |
| 2002/0055007 A1 | 5/2002 | Soane et al. |
| 2002/0082699 A1 | 6/2002 | Ward et al. |
| 2002/0091229 A1 | 7/2002 | Hubbell et al. |
| 2002/0173855 A1 | 11/2002 | Mansmann |
| 2002/0198280 A1 | 12/2002 | Baba et al. |
| 2003/0008396 A1 | 1/2003 | Ku |
| 2003/0022216 A1 | 1/2003 | Mao et al. |
| 2003/0028196 A1 | 2/2003 | Bonutti |

(56) References Cited

U.S. PATENT DOCUMENTS

| | | |
|---|---|---|
| 2003/0064102 A1 | 4/2003 | Nakatsuka |
| 2003/0083389 A1 | 5/2003 | Kao et al. |
| 2003/0083433 A1 | 5/2003 | James et al. |
| 2003/0092777 A1 | 5/2003 | Leitner |
| 2003/0100666 A1 | 5/2003 | DeGroot et al. |
| 2003/0100694 A1 | 5/2003 | Holguin |
| 2003/0114936 A1 | 6/2003 | Sherwood et al. |
| 2003/0130741 A1 | 7/2003 | McMinn |
| 2003/0153981 A1 | 8/2003 | Wang et al. |
| 2003/0170308 A1 | 9/2003 | Cleary et al. |
| 2004/0028804 A1 | 2/2004 | Anderson et al. |
| 2004/0034437 A1 | 2/2004 | Schmieding |
| 2004/0044410 A1 | 3/2004 | Ferree et al. |
| 2004/0059425 A1 | 3/2004 | Schmieding |
| 2004/0116564 A1 | 6/2004 | Devlin et al. |
| 2004/0133275 A1 | 7/2004 | Mansmann |
| 2004/0134502 A1 | 7/2004 | Mizuno et al. |
| 2004/0138382 A1 | 7/2004 | Dous |
| 2004/0139382 A1 | 7/2004 | Kim |
| 2004/0147466 A1 | 7/2004 | Barman et al. |
| 2004/0147927 A1 | 7/2004 | Tsougarakis et al. |
| 2004/0153040 A1 | 8/2004 | Martineau et al. |
| 2004/0153079 A1 | 8/2004 | Tsougarakis et al. |
| 2004/0153163 A1 | 8/2004 | Posner |
| 2004/0167528 A1 | 8/2004 | Schantz |
| 2004/0171740 A1 | 9/2004 | Ruberti et al. |
| 2004/0199250 A1 | 10/2004 | Fell |
| 2004/0204760 A1 | 10/2004 | Fitz et al. |
| 2004/0214914 A1 | 10/2004 | Marmo |
| 2004/0230315 A1 | 11/2004 | Ek |
| 2004/0236424 A1 | 11/2004 | Berez et al. |
| 2004/0266941 A1 | 12/2004 | Houston et al. |
| 2004/0267363 A1 | 12/2004 | Fell et al. |
| 2005/0004306 A1 | 1/2005 | Lubnin et al. |
| 2005/0013793 A1 | 1/2005 | Beckman et al. |
| 2005/0027364 A1 | 2/2005 | Kim et al. |
| 2005/0033295 A1 | 2/2005 | Wisnewski |
| 2005/0038520 A1 | 2/2005 | Binette et al. |
| 2005/0049459 A1 | 3/2005 | Hern |
| 2005/0055044 A1 | 3/2005 | Kangas |
| 2005/0065616 A1 | 3/2005 | Ankorina-Stark et al. |
| 2005/0090612 A1 | 4/2005 | Soane et al. |
| 2005/0113836 A1 | 5/2005 | Lozier et al. |
| 2005/0113928 A1 | 5/2005 | Cragg et al. |
| 2005/0126680 A1 | 6/2005 | Aeschlimann et al. |
| 2005/0142162 A1 | 6/2005 | Hunter et al. |
| 2005/0147685 A1 | 7/2005 | Osada et al. |
| 2005/0171604 A1 | 8/2005 | Michalow |
| 2005/0186248 A1 | 8/2005 | Hossainy et al. |
| 2005/0187146 A1 | 8/2005 | Helmus et al. |
| 2005/0215660 A1 | 9/2005 | Tomikawa et al. |
| 2005/0218541 A1 | 10/2005 | Peng et al. |
| 2005/0228161 A1 | 10/2005 | Benz et al. |
| 2005/0251267 A1 | 11/2005 | Winterbottom et al. |
| 2005/0251268 A1 | 11/2005 | Truncale |
| 2005/0267482 A1 | 12/2005 | Hyde |
| 2005/0267584 A1 | 12/2005 | Burdulis et al. |
| 2005/0278025 A1 | 12/2005 | Ku et al. |
| 2005/0283255 A1 | 12/2005 | Geremakis et al. |
| 2005/0287187 A1 | 12/2005 | Mansmann |
| 2006/0008506 A1 | 1/2006 | Cipriano De Sousa et al. |
| 2006/0052878 A1 | 3/2006 | Schmieding |
| 2006/0083773 A1 | 4/2006 | Myung et al. |
| 2006/0093648 A1 | 5/2006 | Coury et al. |
| 2006/0105295 A1 | 5/2006 | Mayer et al. |
| 2006/0111726 A1 | 5/2006 | Felt et al. |
| 2006/0122543 A1 | 6/2006 | Mayer et al. |
| 2006/0134186 A1 | 6/2006 | Carlton et al. |
| 2006/0142406 A1 | 6/2006 | Schmitt et al. |
| 2006/0148985 A1 | 7/2006 | Karthauser |
| 2006/0188487 A1 | 8/2006 | Thomas et al. |
| 2006/0188940 A1 | 8/2006 | Cima et al. |
| 2006/0193899 A1 | 8/2006 | Sawhney |
| 2006/0224244 A1 | 10/2006 | Thomas et al. |
| 2006/0233855 A1 | 10/2006 | Seliktar et al. |
| 2006/0235517 A1 | 10/2006 | Hodorek |
| 2006/0235539 A1 | 10/2006 | Blunn et al. |
| 2006/0235542 A1 | 10/2006 | Hodorek et al. |
| 2006/0240478 A1 | 10/2006 | Nishimi et al. |
| 2006/0241629 A1 | 10/2006 | Krebs et al. |
| 2006/0241759 A1 | 10/2006 | Trieu |
| 2006/0246241 A1 | 11/2006 | Kruger et al. |
| 2006/0282169 A1 | 12/2006 | Felt et al. |
| 2006/0287721 A1 | 12/2006 | Myung et al. |
| 2006/0287730 A1 | 12/2006 | Segal et al. |
| 2007/0014828 A1 | 1/2007 | Fitzhugh et al. |
| 2007/0016211 A1 | 1/2007 | Botimer |
| 2007/0048382 A1 | 3/2007 | Meyer et al. |
| 2007/0067032 A1 | 3/2007 | Felt et al. |
| 2007/0068816 A1 | 3/2007 | Solomon et al. |
| 2007/0078388 A1 | 4/2007 | Kangas |
| 2007/0078518 A1 | 4/2007 | Lavi |
| 2007/0083266 A1 | 4/2007 | Lang |
| 2007/0087031 A1 | 4/2007 | Ashman et al. |
| 2007/0088444 A1 | 4/2007 | Hodorek et al. |
| 2007/0098675 A1 | 5/2007 | Elisseeff et al. |
| 2007/0099840 A1 | 5/2007 | Ulijn et al. |
| 2007/0100457 A1 | 5/2007 | Hyde |
| 2007/0118218 A1 | 5/2007 | Hooper |
| 2007/0126982 A1 | 6/2007 | Myung et al. |
| 2007/0134291 A1 | 6/2007 | Ting et al. |
| 2007/0135922 A1 | 6/2007 | Trieu |
| 2007/0141108 A1 | 6/2007 | Thomas et al. |
| 2007/0142914 A1 | 6/2007 | Jones et al. |
| 2007/0149441 A1 | 6/2007 | Aeschlimann et al. |
| 2007/0167541 A1 | 7/2007 | Ruberti et al. |
| 2007/0179605 A1 | 8/2007 | Myung et al. |
| 2007/0179607 A1 | 8/2007 | Hodorek et al. |
| 2007/0179622 A1 | 8/2007 | Denoziere et al. |
| 2007/0191963 A1 | 8/2007 | Winterbottom et al. |
| 2007/0198022 A1 | 8/2007 | Lang et al. |
| 2007/0202148 A1 | 8/2007 | Ringeisen et al. |
| 2007/0219640 A1 | 9/2007 | Steinberg |
| 2007/0224238 A1 | 9/2007 | Mansmann et al. |
| 2007/0225823 A1 | 9/2007 | Hawkins et al. |
| 2007/0233240 A1 | 10/2007 | Frank et al. |
| 2007/0233269 A1 | 10/2007 | Steines et al. |
| 2007/0265704 A1 | 11/2007 | Mayer et al. |
| 2007/0270783 A1 | 11/2007 | Zumsteg et al. |
| 2007/0276394 A1 | 11/2007 | Johnson et al. |
| 2008/0058954 A1 | 3/2008 | Trieu |
| 2008/0070086 A1 | 3/2008 | Fukuchi et al. |
| 2008/0077249 A1 | 3/2008 | Gradel |
| 2008/0103505 A1 | 5/2008 | Fransen |
| 2008/0124376 A1 | 5/2008 | Pruitt et al. |
| 2008/0139694 A1 | 6/2008 | Ratcliffe |
| 2008/0182919 A1 | 7/2008 | Saimi et al. |
| 2008/0241214 A1 | 10/2008 | Myung et al. |
| 2008/0269370 A1 | 10/2008 | Myung et al. |
| 2008/0302479 A1 | 12/2008 | Barker et al. |
| 2008/0317818 A1 | 12/2008 | Griffith et al. |
| 2009/0035344 A1 | 2/2009 | Thomas et al. |
| 2009/0062408 A1 | 3/2009 | Liu et al. |
| 2009/0062423 A1 | 3/2009 | Betz et al. |
| 2009/0088846 A1 | 4/2009 | Myung et al. |
| 2009/0105366 A1 | 4/2009 | Vogt et al. |
| 2009/0142508 A1 | 6/2009 | Lai et al. |
| 2009/0163860 A1 | 6/2009 | Patrick et al. |
| 2009/0176891 A1 | 7/2009 | Chogle et al. |
| 2009/0209966 A1 | 8/2009 | Chandler |
| 2009/0221730 A1 | 9/2009 | Kowalski et al. |
| 2009/0233887 A1 | 9/2009 | Shalaby et al. |
| 2009/0234044 A1 | 9/2009 | Rheinberger et al. |
| 2009/0240337 A1 | 9/2009 | Myung et al. |
| 2009/0270527 A1 | 10/2009 | Lin et al. |
| 2009/0281545 A1 | 11/2009 | Stubbs |
| 2009/0312807 A1 | 12/2009 | Boudreault et al. |
| 2010/0010114 A1 | 1/2010 | Myung et al. |
| 2010/0032090 A1 | 2/2010 | Myung et al. |
| 2010/0056646 A1 | 3/2010 | Shalaby et al. |
| 2010/0125341 A1 | 5/2010 | Frauens |
| 2011/0152868 A1 | 6/2011 | Kourtis et al. |
| 2011/0184423 A1 | 7/2011 | Rushton et al. |
| 2011/0237705 A1 | 9/2011 | Leonard et al. |

(56) References Cited

U.S. PATENT DOCUMENTS

| | | | |
|---|---|---|---|
| 2012/0045651 | A1 | 2/2012 | Myung et al. |
| 2012/0116531 | A1 | 5/2012 | Forsell |
| 2012/0209396 | A1 | 8/2012 | Myung et al. |
| 2012/0232512 | A1 | 9/2012 | Myung et al. |
| 2012/0277807 | A1 | 11/2012 | Myung et al. |
| 2012/0308508 | A1 | 12/2012 | Saunders et al. |
| 2013/0030058 | A1 | 1/2013 | Vogt et al. |
| 2013/0096691 | A1 | 4/2013 | Myung et al. |
| 2013/0103157 | A1* | 4/2013 | Kourtis ............. C08G 18/6511 623/18.11 |
| 2013/0131741 | A1 | 5/2013 | Kourtis et al. |
| 2013/0138210 | A1 | 5/2013 | Myung et al. |
| 2013/0138211 | A1 | 5/2013 | Myung et al. |
| 2013/0197126 | A1 | 8/2013 | Vogt |
| 2013/0217829 | A1 | 8/2013 | Myung et al. |
| 2014/0005635 | A1 | 1/2014 | Boger et al. |
| 2014/0172098 | A1 | 6/2014 | Myung et al. |
| 2015/0025161 | A1 | 1/2015 | Myung et al. |
| 2015/0122418 | A1 | 5/2015 | Gerst et al. |
| 2015/0272599 | A1 | 10/2015 | Kourtis et al. |
| 2015/0284654 | A1 | 10/2015 | Myung et al. |
| 2015/0299345 | A1 | 10/2015 | Xu et al. |
| 2016/0015604 | A1 | 1/2016 | Aechtner |
| 2016/0346089 | A1 | 12/2016 | Myung et al. |
| 2017/0107370 | A1 | 4/2017 | Myung et al. |
| 2017/0327624 | A1* | 11/2017 | Kourtis ............. C08G 18/6229 |
| 2017/0348011 | A1 | 12/2017 | Kourtis et al. |
| 2018/0236136 | A1 | 8/2018 | Kourtis et al. |
| 2019/0218386 | A1 | 7/2019 | Kourtis et al. |
| 2019/0224367 | A1 | 7/2019 | Kourtis et al. |
| 2020/0023098 | A1 | 1/2020 | Kourtis et al. |
| 2020/0046880 | A1 | 2/2020 | Kourtis et al. |

FOREIGN PATENT DOCUMENTS

| | | |
|---|---|---|
| EP | 0971677 B1 | 2/2005 |
| EP | 1779875 A1 | 5/2007 |
| EP | 2139530 B1 | 8/2011 |
| EP | 1900761 B1 | 6/2012 |
| EP | 2284238 B1 | 7/2013 |
| EP | 2609154 A1 | 7/2013 |
| EP | 2139967 B1 | 12/2014 |
| EP | 2828314 A1 | 1/2015 |
| EP | 2411426 B1 | 8/2016 |
| GB | 2372707 A | 9/2002 |
| JP | H06-287443 A | 10/1994 |
| JP | H09-077809 A | 3/1997 |
| JP | H10-500038 A | 1/1998 |
| JP | 2002514233 A | 5/2002 |
| JP | 2002518564 A | 6/2002 |
| JP | 2002518565 A | 6/2002 |
| JP | 2003171475 A | 6/2003 |
| WO | WO-94/01468 A1 | 1/1994 |
| WO | WO-95/30388 A1 | 11/1995 |
| WO | WO-99/45978 A1 | 9/1999 |
| WO | WO-00/02937 A1 | 1/2000 |
| WO | WO-00/043050 A1 | 7/2000 |
| WO | WO-02/026848 A2 | 4/2002 |
| WO | WO-2004/055057 A1 | 7/2004 |
| WO | WO-2004/091685 A2 | 10/2004 |
| WO | WO-2007/067697 A2 | 6/2007 |
| WO | WO-2007/112305 A2 | 10/2007 |
| WO | WO-2009/071937 A1 | 6/2009 |
| WO | WO-2010/037685 A1 | 4/2010 |
| WO | WO-2010/059495 A2 | 5/2010 |
| WO | WO-2015/023569 A1 | 2/2015 |

OTHER PUBLICATIONS

Bobyn et al., The optimum pore size for the fixation of porous-surfaced metal implants by the ingrowth of bone. Clin Orthop Relat Res, Jul./Aug. 1980(150): p. 263-270.

Borden et al.; The sintered microsphere matrix for bone tissue engineering: In vitro osteoconductivity studies; J. Biomed. Mat. Res.; 61(3); pp. 421-429; Sep. 2002.

Brodbeck et al., Biomaterial adherent macrophage apoptosis is increased by hydrophilic and anionic substrates in vivo. Proc Natl Acad Sci U S A, Aug. 6, 2002. 99(16): p. 10287-10292.

Brown et al.; Solvent/Non-solvent sintering: A novel route to create porous microsphere scaffolds for tissue regeneration; J. Biomed. Mat. Res. (Part B: Applied Biomaterials); 86B(2); pp. 396-406; Aug. 2008.

Causton et al.; Dental materials: 1981 literature review Part 1; Journal of Dentistry; vol. 12; Issue 1; pp. 1R28; Mar. 1984.

Charnley, J.; Anchorage of the femoral head prosthesis to the shaft of the femur; J Bone Joint Surg Br.; 42-B:28-30; Feb. 1960.

Chen et al.; Mechanical Properties of Polyepichlorohydrin Polyurethane/Poly(methyl methacrylate) IPNs; Chinese J Appl Chem; 12(4):66-69; Aug. 1995 (wEngAbs).

Covert et al.; Friction characteristics of a potential articular cartilage biomaterial. Wear, Aug. 2003. 255: p. 1064-1068.

Depuy Orthopaedics; Bone Cement Time Setting Chart; product file; date of publication unknown; available to applicants at least as of Jul. 2012.

Dror et al.; Gradient interpenetrating polymer networks. I. Poly(ether urethane) and polyacrylamide IPN; J of Applied Polymer Science; 26; pp. 1741-1757; Jun. 1981.

Elmer's Products Inc.; Material Safety Data Sheet; "Elmer's Nano Glue"; Jun. 13, 2007.

Elsabee et al.; Gradient interpenetrating polymer networks. II. Polyacrylamide gradients in poly(ether urethane); J of Applied Polymer Science; 28(7); pp. 2151-2166; Jun. 1983.

Esstech, Inc.; Urethane Dimethacrylate (product specification); 1 pg.; Note: this document was available to applicant(s) at least as of (Apr. 8, 2015).

Evans et al.; The use of corneal organ culture in biocompatibility studies; Biomaterials; vol. 23; pp. 1359-1367; Mar. 2002.

Frank, Curt; Structure-property relationships for hydrogels with applications to biomedical devices; Presentation at American Chemical Society Mtg; San Francisco, CA; Sep. 11, 2006.

Gao et al.; Grafting of hydrophilic monomers onto polyurethane membranes by solution or pre-absorbing methods for acceleration of cell compatibility; Chinese Journal of Polymer Science; vol. 19; No. 5; pp. 493-498; Oct. 20, 2001.

Gong et al.; Double-network hydrogels with extremely high mechanical strength; Adv. Mater.; vol. 15; No. 14; pp. 1155-1158; Jul. 17, 2003.

Gorna et al.; Preparation, degradation, and calcification of biodegradable polyurethane foams for bone graft substitutes; J Biomed Mater Res A. 67(3): 813-827 (2003).

Guelcher et al.; Synthesis and in vitro biocompatibility of injectable polyurethane foam scaffolds; Tissue Engineering; 12(5); pp. 1247-1259; May 2006.

Guelcher et al.; Synthesis of biocompatible segmented polyurethanes from aliphatic diisocyanates and diurea diol chain extenders; Acta biomaterialia; 1(4); pp. 471-484; Jul. 2005.

Gunatillake et al.; Designing biostable polyurethane elastomers for biomedical implants; Aust. J. Chem.; vol. 56; pp. 545-557; Jun. 2003.

Hern et al.; Incorporation of adhesion peptides into nonadhesive hydrogels useful for tissue resurfacing; J. Biomed. Materials Research; vol. 39; No. 1; pp. 266-276; Feb. 1998.

Ithaca College Gross Anatomy; Joints of the Back; ; 4 pgs. (downloaded Dec. 1, 2013 from http://www.ithaca.edu/faculty/lahr/LE2000/Back/Jointpage.htm).

Iwasaki et al., Hydrogel-like elastic membrane consisting of semi-interpenetrating polymer networks based on a phosphorylcholine polymer and a segmented polyurethane; J. Polym. Sci Part A: Polym Chem; 41; pp. 68-75; Jan. 2003.

Jones et al.; Sequential Polyurethane-Poly(Methylmethacrylate) Interpenetrating Polymer Networks as Ureteral Biomaterials: Mechanical Properties and Comparative Resistance to Urinary Encrustation; J Mater Sci Mater Med; 8(11):713-717; Nov. 1997.

Kanie et al.; Flexural properties of ethyl or methyl methacrylate-UDMA blend polymers; Dent Mater J; 29(5); pp. 575-581; Oct. 2010.

(56) References Cited

OTHER PUBLICATIONS

Khan et al., Analysis and evaluation of a biomedical polycarbonate urethane tested in an in vitro study and an ovine arthroplasty model. Part I: materials selection and evaluation. Biomaterials, Feb. 2005. 26(6): p. 621-631.
Kim et al.; Electrical/pH Responsive Properties of Poly(2-acrylamido-2-methylpropane sulfonic acid)/Hyaluronic Acid Hydrogels; Journal of Applied Polymer Science; vol. 92; issue 3; pp. 1731-1736; May 2004.
Kim et al.; Electrochemical behavior of an interpenetrating polymer network hydrogel composed of poly (propylene glycol) and poly(acrylic acid); Journal of Applied Polymer Science; vol. 89; pp. 2301-2305; Aug. 2003.
Kim et al.; Water sorption of ploy(propylene glycol)/poly(acrylic acid) interpenetrating polymer network hydrogels; Reactive & Functional Polymers; vol. 55; pp. 69-73; Feb. 2003.
Kourtis et al., U.S. Appl. No. 13/683,731, entitled "Systems, Devices, and Methods for Anchoring Orthopaedic Implants to Bone," filed Nov. 21, 2012 (130 pages).
Kwong et al., "A comparison of the shrinkage of commercial bone cements when mixed under vacuum" J Bone Joint Surg Br. 88(1):120-2 (2006).
Lam et al.; Update on Ureteral Stents; Urology; 64:9-15; Jul. 2004.
Lamba et al.; Polyurethanes in Biomedical Applications; CRC Press; pp. 11, 14, 16, 18-20, 57-59, 73, 79 & 104; Nov. 1997.
Lee et al.; Interpenetrating polymer network hydrogels based on poly (ethylene glycol) macromer and chitosan; Carbohydrate Polymer; vol. 41; No. 2; pp. 197-205; Feb. 2000.
Lewis G., "Properties of acrylic bone cement: state of the art review," J Biomed Mater Res. 38(2):155-82 (1997).
Lipatov et al.; Gradient interpenetrating polymer networks; Journal of Materials Science; 30(4); pp. 1095-1104; Feb. 1995.
Lu et al.; Release behavior of high molecular weight solutes from poly(ethylene glycol)-based degradable networks; Macromolecules; vol. 33(7); pp. 2509-2515; Mar. 2000.
Maroudas et al.; Permeability of articular cartilage; Nature; vol. 219(5160); pp. 1260-1261; Sep. 21, 1968.
MIT.edu; Material Modulus Properties; 2pgs.; Feb. 8, 2007 (downloaded Nov. 27, 2013 from http://web.archive.org/web/*/http://web.mit.edu/course/3/3.11/www/modules- /props.pdf).
Morgan et al., "Dependence of yield strain of human trabecular bone on anatomic site," J Biomech. 34(5):569-77 (2001).
Mow et al., Basic Orthopaedic Biomechanics and Mechano-Biology, Lippincot Williams and Wilkins, 3rd Edition, Apr. 2005, pp. 459-461.
Myung et al.; Biomimetic strain hardening in interpenetrating polymer network hydrogels; Polymer, ; vol. 48; No. 18; pp. 5376-5387; Jun. 2007.
Myung et al.; U.S. Appl. No. 13/748,573, entitled "Hydrophilic Interpenetrating Polymer Networks Derived From Hydrophobic Polymers," filed Jan. 23, 2013 (99 pages).
Myung et al.; U.S. Appl. No. 13/748,576, entitled "Hydrophilic Interpenetrating Polymer Networks Derived From Hydrophobic Polymers," filed Jan. 23, 2013 (103 pages).
Myung et al.; U.S. Appl. No. 13/816,537, entitled "Hydrophobic and Hydrophilic Interpenetrating Polymer Networks Derived From Hydrophobic Polymers and Methods of Preparing the Same," filed Apr. 24, 2013 (153 pages).
Myung et al.; U.S. Appl. No. 13/905,028, entitled "Polyurethane-grafted hydrogels," filed May 29, 2013 (58 pages).
Myung, David; Structure, properties, and medical device applications of mechanically enhanced, biometric hydrogel alloys; Doctoral Thesis; Stanford University; Dec. 2007.
Neurosurgical.com; Spinal Anatomy: The Regions of the Spine; 5pgs. (downloaded Dec. 1, 2013 http://www.neurosurgical.com/neuro_medical_info/spinal_anatomy.htm).
Ohman et al.; Mechanical testing of cancellous bone from the femoral head: experimental errors due to off-axis measurements; J Biomech.; 40(11):2426-33; (year of publication is sufficiently earlier than the effective U.S. filing date and any foreignpriority date) 2007.
Orr et al., "Shrinkage stresses in bone cement," Biomaterials. 24(17):2933-40 (2003).
Park et al.; Synthesis of PVA/PVP hydrogels having two-layer by radiation and their physical properties; Radiation Physics and Chemistry; 67(3-4); pp. 361-365; Jun. 2003.
Puska et al.; Exothermal Characteristics and Release of Residual Monomers from Fiber-reinforced Oligomer-modified Acrylic Bone Cement; J Biomat App; 20:51-64; Jul. 2005.
Realdictionary; Definition of Implant; 4pgs. (downloaded Dec. 1, 2013 from www.realdictionary.com/?q=implant).
Saito et al.; Preparation and properties of transparent cellulose hydrogels; J. Applied Polymer Science; 90(11); pp. 3020-3025; Dec. 2003.
Scholes et al.; Compliant layer acetabular cups: friction testing of a range of materials and designs for a new generation of prosthesis that mimics the natural joint; Proc. IMechE; vol. 220(5); Part H; J. Engineering in Medicine; pp. 583-596, Jul. 2006.
Shalaby; U.S. Appl. No. 61/069,046 entitled "Hydroswellable, segmented, aliphatic polyurethanes and polyurethane ureas," filed Mar. 12, 2008.
Sigma-Aldrich; Methyl Methacrylate (product specification); 1 pg.; Note: this document was available to applicant(s) at least as of (Jun. 19, 2014).
Spector et al.; Porous polymers for biological fixation. Clin Orthop Relat Res, Oct. 1988 (235): p. 207-219.
Stammen et al., Mechanical properties of a novel PVA hydrogel in shear and unconfined compression. Biomaterials, Apr. 2001. 22(8): p. 799-806.
Stryker Orthopaedics; SimplexTM P Bone Cement; Product Literature LSB Rev. 3, Mar. 2006.
Tanaka et al.; Polymer properties on resins composed of UDMA and methacrylates with the carboxyl group; Dental Materials Journal; 20(3); pp. 206-215; Sep. 2001.
Tariq et al.; (Abstract) Sodium benzoate attenuates iminodipropionitrile-induced behavioral syndrome in rats. Behav pharmacol; Dec. 2004.
Tawfik, Dan; Amidation of carboxyl groups; The Protein Protocols Handbook, 2nd Ed.; Humana Press; pp. 477-478; Feb. 2002.
The Engineering Toolbox; Polyurethane insulation: {http://www.engineeringtoolbox.com/polyurethane-insulation-k-values-d_117-4.html} pp. 1-3; printed Oct. 21, 2011.
The Engineering Toolbox;Thermal conductivity of some common materials and gases: {http://www.engineeringtoolbox.com/thrmal-conductivity-d_429.html} pp. 1-2; printed Oct. 21, 2011.
The Gorilla Glue Company; Material Safety Data Sheet; "New Fast Cure-Dries White Gorilla Glue.RTM."; Jan. 30, 2007.
The Gorilla Glue Company; Material Safety Data Sheet; "New Stronger-Faster Gorilla Glue.RTM."; Jan. 26, 2007.
Van Landuyt et al.; Reinforcement of Osteosynthesis Screws with Brushite Cement; Bone; 25(2)(Suppl 1):95S-98S; Aug. 1999.
Wittemann et al.; Adsorption of proteins on spherical polyelectrolyte brushes in aqueous solution; Phys. Chem. Chem. Phys., Mar. 2003, vol. 5(8), pp. 1671-1677.
Wright et al., Wear studies on prosthetic materials using the pin-on-disc machine. Biomaterials, vol. 3, Issue 1, Jan. 1982, pp. 41R48.
Yang et al.; Preparation of poly(acrylic acid) modified polyurethane membrane for biomaterial by UV radiation without degassing; J. Biomed. Mater. Res.; vol. 45(2); pp. 133-139; May 1999.
Yim et al., Biocompatibility of poly(ethylene glycol)/poly(acrylic acid)interpenetrating polymer network hydrogel particles inRAW 264.7 macrophage and MG-63 osteoblast cell lines. Journal of Biomedical Materials Research, 91A(3); pp. 894-902; Dec. 1, 2009.
Zhu et al.; (Abstract) Promoting the cytocompatibility of polyurethane scaffolds via surface photo-grafting polymerization of acrylamide; J. Mater. Sci. Mater. Med.; vol. 15; No. 3; pp. 283-289; Mar. 2004.

\* cited by examiner

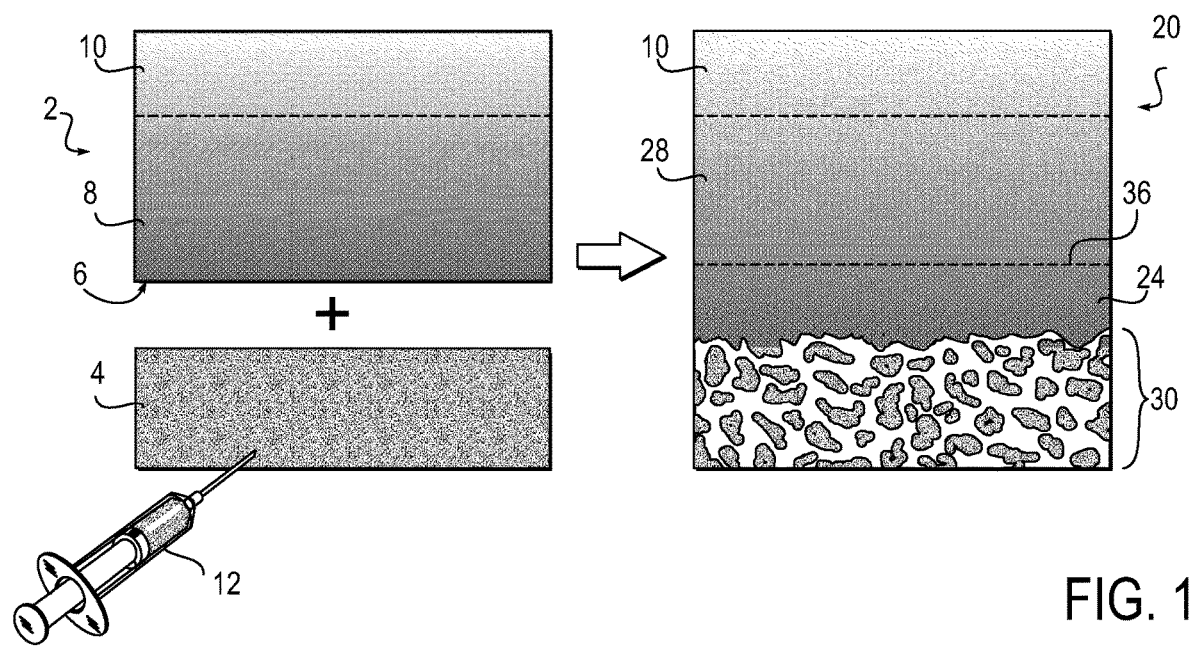
FIG. 1
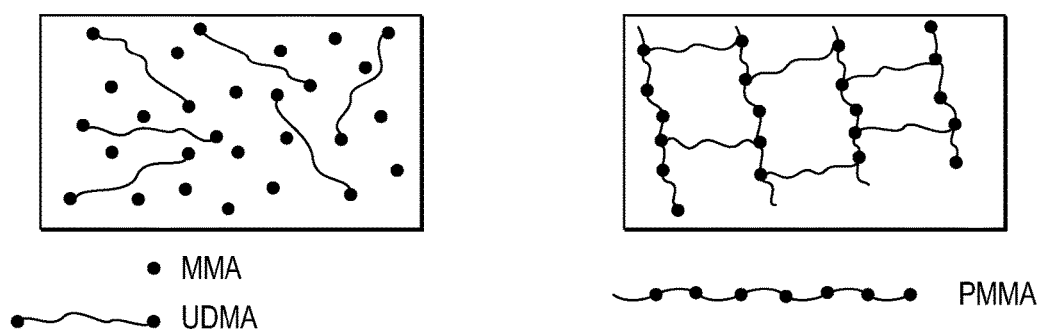
FIG. 2A
FIG. 2B

| Company Name | Product Name | Application | Active Ingredient (pre cured) |
|---|---|---|---|
| Heraeus Dental | iBond Total Etch | Dental Adhesive Cement | UDMA |
| Dentsply International | SmartCem2 | Dental Adhesive Cement | UDMA, Acrylated Esters of Phosphoric Acid |
| Ivoclar vivadent | Tetric EvoFlow | Dental Adhesive Cement | UDMA, Bis-GMA |
| PulpDent | Lime-Lite | Dental cavity liner | UDMA, Hydroxyapatite |
| Stryker | Simplex P | Orthopedic Bone Cement | MMA, MMA-Styrene Copolymer |
| Zimmer | Palacos | Orthopedic Bone Cement | MMA-Methyl Acrylate Copolymer |
| DePuy | CMW | Orthopedic Bone Cement | PMMA |

FIG. 6A

| Components | (w/w) | Commercial product that contains constituent |
|---|---|---|
| Urethane Dimethacrylate (UDMA) | 60%-80% | iBond, SmartCem2, Tetric EvoFlow, Lime-Lite |
| Methyl Methacrylate (MMA) | 20%-40% | Simplex P, Palacos R, CMW |
| Camphorquinone (initiator) | <1% | iBond, SmartCem2, Tetric EvoFlow, Lime-Lite |
| Benzoyl Peroxide (initiator) | <1% | Simplex P, Palacos R, CMW |
| N,N-dimethyl-p-toluidine (accelerator) | <1% | Simplex P, Palacos R, CMW |
| Hydroquinone (inhibitor) | 0.1% | Simplex P, Palacos R, CMW |

| Ingredient | %(w/w) | Chemical Formula |
|---|---|---|
| UDMA-MMA Copolymer (initiators and accelerators incorporated) | >95% | |
| Methyl methacrylate | <3% | |
| 4,4'-Methylenebis(phenyl isocyanate) | <0.1% | |
| Poly(tetrahydrofuran) | <0.1% | |
| 2-Hydroxyethyl methacrylate | <1% | |
| N,N-Dimethly-p-toluidine (DMPT) | <1% | |
| Camphorquinone | <0.5% | |
| Benzoyl Peroxide | <0.5% | |

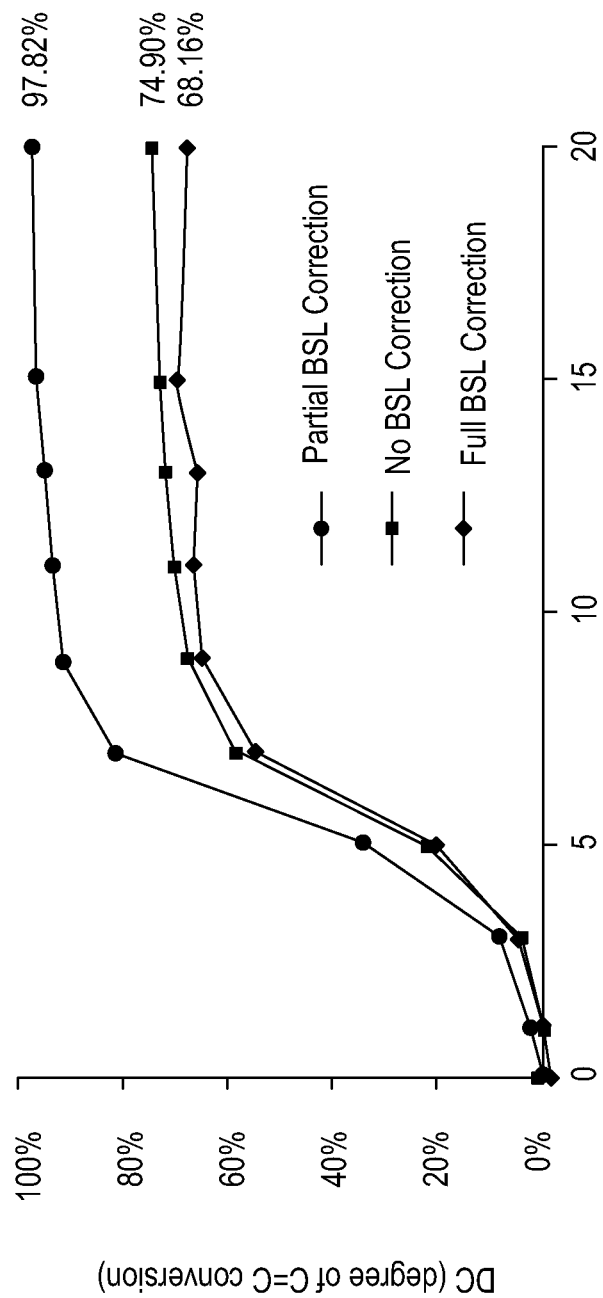

| | Cancellous Bone | PMMA bone cements | Polymeric Adhesive | IPN/semi-IPN containing material/device |
|---|---|---|---|---|
| Viscosity (@18°C) | - | 10-500 Pa·s | 2-98 Pa·s | - |
| Curing Temperature | - | 55-92°C | <70°C | - |
| Working Time | - | 3-8 min | 2.5-5 min | - |
| Setting Time (light) | - | - | <2 min | - |
| Setting Time (thermal) | - | 6-14 min | 5-8 min | - |
| Tensile Modulus (@ 2 MPa) | 500-3500 MPa | 1500-4100 MPa | 530 ± 27 MPa | 36.8 ± 0.4 MPa |
| Tensile Strength | 4.5-11 MPa | 25-49 MPa | 29.2 ± 0.7 MPa | 107 ± 11 MPa |
| Ultimate Tensile Strain | 0.60-0.65% | 0.9-2.5% | 117.6 ± 2.7% | 175 ± 24% |
| Compressive Modulus | 500-3500 MPa | 1900-3200 MPa | 214 ± 42 | 29.2 ± 4.5 MPa |
| Compressive Strength | 6-18 MPa | 73-117 MPa | > 30 MPa | >> 12 MPa |
| Ultimate/Yield Compressive Strain | 0.70-0.85% | 5.0-7.5% | >> 10% | > 60% |
| Permanent Creep (@2.7 MPa) | - | - | 3.5% | - |
| Tear Strength | - | - | - | 28.0 ± 2.5 N/mm |
| Peel Strength (initiation) | - | <1 N/mm | 14.4 ± 3.4 N/mm | - |
| Peel Strength (propagation) | - | <1 N/mm | 4.2 ± 1.1 N/mm | - |
| Static PU-Bone Shear | - | 4.8 ± 0.4 MPa | 5.7 ± 1.4 MPa | - |

FIG. 22

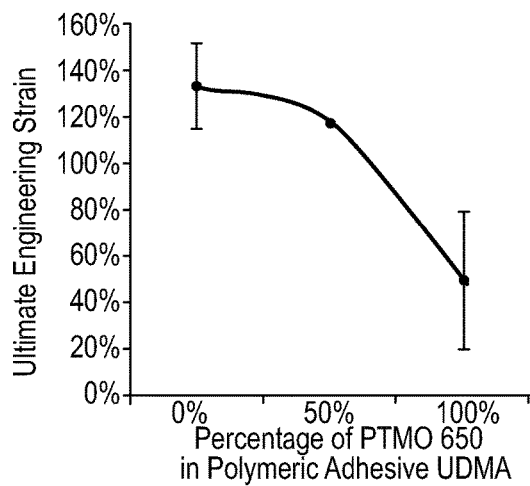
FIG. 42A
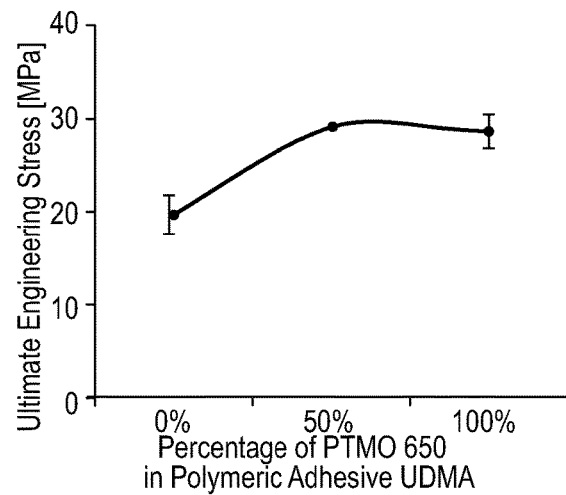
FIG. 42B
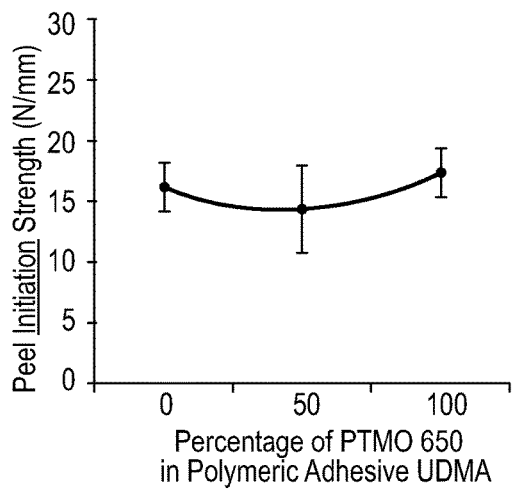
FIG. 43A
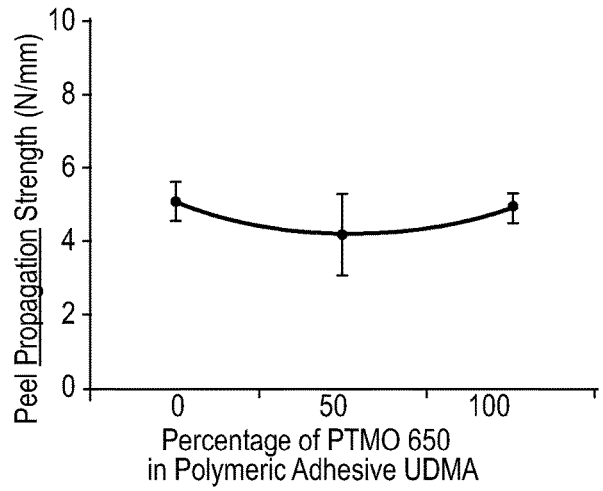
FIG. 43B
FIG. 44

POLYMERIC ADHESIVE FOR ANCHORING COMPLIANT MATERIALS TO ANOTHER SURFACE

CROSS REFERENCE TO RELATED APPLICATIONS

This application is a continuation of U.S. patent application Ser. No. 15/668,547, filed Aug. 3, 2017, which is a continuation of U.S. patent application Ser. No. 14/877,884, filed Oct. 7, 2015, now U.S. Pat. No. 9,750,842, which is a continuation of U.S. patent application Ser. No. 13/573,788, filed Oct. 3, 2012, which claims the benefit of U.S. Provisional Patent Application No. 61/542,740, filed Oct. 3, 2011, and to U.S. Provisional Patent Application No. 61/672,203, filed Jul. 16, 2012. Each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention pertains to methods, compositions, and kits for making and using an adhesive copolymer.

BACKGROUND

The art has described semi- and fully interpenetrating polymer networks (IPNs) for use in a variety of applications. For example, U.S. application Ser. No. 12/499,041 filed Jul. 7, 2009, U.S. application Ser. No. 13/219,348 filed Aug. 26, 2011, and U.S. application Ser. No. 13/347,647 filed Jan. 10, 2012 (all of which are incorporated by reference herein) describe IPNs formed from hydrophobic and hydrophilic polymer for use, e.g., in orthopedic applications. U.S. application Ser. No. 13/219,348 also describes how to increase the adhesive properties of such IPNs and the articles they are made from and gives some examples of attachment of such articles to, e.g., bones or bone-like structures.

U.S. application Ser. No. 12/409,359 (filed Mar. 23, 2009 and incorporated by reference herein) describes the use of polyurethane polymers to adhere hydrated polymers (such as hydrogels and hydrogel composites) to mammalian bone or bone-like structures.

SUMMARY OF THE DISCLOSURE

The present invention relates in general to methods, kits, and compositions for adhering two substances together. One aspect takes advantage of the physical and chemical properties of a polymer to achieve the goal of high mechanical strength in addition to other desirable properties. The invention also relates to the use of a polymer, such as a polyurethane-based copolymer, to attach a medical implant to a joint.

One aspect of the invention provides a composition of matter including a urethane dimethacrylate-methyl methacrylate copolymer having a plurality of first polymer regions based on urethane dimethacrylate and a plurality of second polymer regions based on methyl methacrylate. In some embodiments, the first polymer regions based on urethane dimethacrylate include about 60%-99% (w/w) of the copolymer and the second polymer regions based on methyl methacrylate include about 1%-40% (w/w) of the copolymer. In some embodiments, the first polymer regions based on urethane dimethacrylate includes about 60%-80% (w/w) of the copolymer and the second polymer regions based on methyl methacrylate includes from about 20%-40% (w/w) of the copolymer. In some embodiments, the first polymer regions based on urethane dimethacrylate include soft segments based on poly(tetramethyl) glycol, the soft segments having a molecular weight between about 100 Da and about 5000 Da.

In some embodiments, the urethane dimethacrylate-methyl methacrylate copolymer defines a compressive modulus between about 30 MPa and about 2000 MPa. In some embodiments, the urethane dimethacrylate-methyl methacrylate copolymer defines a tensile modulus between about 30 MPa and 2000 MPa. In some embodiments, the urethane dimethacrylate-methyl methacrylate copolymer defines a failure strain between about 25% and 200%.

In some embodiments, the composition further includes a radiopaque material.

Another aspect of the invention provides a composition of matter including from about 60% (w/w) to about 99% (w/w) urethane dimethacrylate monomer; from about 1% (w/w) to about 40% (w/w) methyl methacrylate monomer; an initiator; an accelerator; and an inhibitor.

In some embodiments, the composition includes between 0% (w/w) to about 1% (w/w) initiator, between 0% (w/w) to about 1% (w/w) accelerator; and between 0% (w/w) to about 0.1% (w/w) inhibitor. In some embodiments, the composition includes from about 60% (w/w) to about 80% (w/w) urethane dimethacrylate monomer and from about 20% (w/w) to about 40% (w/w) methyl methacrylate monomer.

In some embodiments, the composition includes from about 1% (w/w) to about 70% (w/w) poly(methyl methacrylate) powder.

In some embodiments, the composition includes a photoinitiator and/or a thermal initiator (such as camphorquinone or benzoyl peroxide). In some embodiments, the accelerator includes N,N-dimethyl-p-toluidine. In some embodiments, the inhibitor includes hydroquinone.

In some embodiments, the composition includes an additive configured to prevent an infection (such as an antibiotic). In some embodiments, the composition includes a radiopaque material.

In some embodiments, the composition the composition defines a viscosity between about 1 Pa·s and about 5000 Pa·s.

Another aspect of the invention provides an adhesive kit including a first reservoir having a first mixture including at least one of a urethane dimethacrylate monomer and a methyl methacrylate monomer; at least one of a photoinitiator and a thermal initiator; and an inhibitor; a second reservoir having a second mixture including at least one of a urethane dimethacrylate monomer and a methyl methacrylate monomer; and an accelerator; and an instruction for use; wherein at least one of the first reservoir and the second reservoir includes a urethane dimethacrylate monomer and at least one of the first reservoir and the second reservoir includes a methyl methacrylate monomer. In some embodiments, both the first reservoir and the second reservoir include a urethane dimethacrylate monomer and a methyl methacrylate monomer.

In some embodiments, the second reservoir further includes an inhibitor.

In some embodiments, the adhesive kit further includes poly(methyl methacrylate), such as, e.g., a third reservoir including a poly(methyl methacrylate) powder. In some embodiments the first mixture, the second mixture and the poly(methyl methacrylate) define a component weight, and a weight of the poly(methyl methacrylate) powder is from about 1% to about 70% of the component weight.

In some embodiments, the adhesive kit further includes a polystyrene. In some embodiments, the adhesive kit further includes a photoinitiator and a thermal initiator.

In some embodiments, the first reservoir includes a first chamber in a syringe and the second reservoir includes a second chamber in the syringe, wherein the syringe is configured to combine the first mixture with the second mixture to create an adhesive mixture. In some embodiments, the syringe includes a nozzle connected with the syringe configured to dispense the adhesive mixture.

In some embodiments, the first reservoir and the second reservoir each includes from about 60% (w/w) to about 80% (w/w) urethane dimethacrylate monomer. In some embodiments, the first reservoir and the second reservoir each includes from about 20% (w/w) to about 40% (w/w) methyl methacrylate.

In some embodiments, the at least one initiator includes a photoinitiator having between 0% (w/w) and about 1% (w/w) camphorquinone. In some embodiments, the at least one initiator includes a thermal initiator having between 0% (w/w) and about 1% (w/w) benzoyl peroxide. In some embodiments, the accelerator includes between 0% (w/w) and about 1% (w/w) N,N-dimethyl-p-toluidine. In some embodiments, the inhibitor includes between 0% (w/w) and about 0.1% (w/w) hydroquinone.

In some embodiments, the adhesive kit includes an additive configured to prevent an infection, such as, e.g., an antibiotic. In some embodiments, the adhesive kit includes a radiopaque material.

In some embodiments, the first mixture defines a viscosity between about 1 Pa·s and 5000 Pa·s.

Another aspect of the invention provides a method of attaching an orthopedic joint implant to a joint. In some embodiments, the method includes the steps of placing an orthopedic joint implant in a joint space, the orthopedic joint implant having a bearing surface and an attachment surface adapted to attach the orthopedic joint implant to a joint surface of a joint; applying a first non-urethane-containing precursor, a second urethane-containing precursor, and a first initiator to the attachment surface of the orthopedic joint implant; contacting the first precursor, the second precursor, and the first initiator with the joint surface; and copolymerizing the first non-urethane-containing precursor with the second urethane-containing precursor and forming an adhesive copolymer including a non-urethane-containing portion based on the first precursor and a urethane-containing portion based on the second precursor to thereby attach the orthopedic joint implant to the joint.

In some embodiments, the first precursor includes a first chemical functional group, the second precursor includes a second chemical functional group, and the first initiator includes a free-radical initiator, and the method includes first precursor includes a first chemical functional group, the second precursor includes a second chemical functional group, and the first initiator includes a free-radical initiator, and the step of copolymerizing includes forming a covalent bond between the first functional group and the second functional group in response to the free-radical initiator. In some embodiments, the first precursor includes a first ethylenically unsaturated group and the second precursor includes a second ethylenically unsaturated group and the step of copolymerizing includes forming a covalent bond between the first ethylenically unsaturated group and the second ethylenically unsaturated group in response to a free-radical initiator. In some embodiments, the first precursor includes first precursor molecules each having an acrylic group, and the step of copolymerizing includes covalently bonding a plurality of first precursor molecules through the acrylic groups. In some embodiments, the second precursor includes second precursor molecules having two acrylic groups, and the step of copolymerizing includes covalently bonding a plurality of second precursor molecules through the acrylic groups.

In some embodiments, the copolymer includes a plurality of first structural units corresponding to the first non-urethane-containing precursor and a plurality of second structural units corresponding to the second urethane-containing precursor, the method further includes at least one of forming a crosslink between at least two of the first structural units, forming a crosslink between at least two of the second structural units, and forming a crosslink between a first structural unit and a second structural unit.

In some embodiments, the first precursor includes a methyl methacrylate monomer and the second precursor includes a urethane dimethacrylate monomer, and the step of copolymerizing includes forming a urethane dimethacrylate-methyl methacrylate copolymer. Some embodiments include the step of mixing the first non-urethane-containing precursor, the second urethane-containing precursor and the first initiator prior to the applying step.

In some embodiments, the first initiator include a photoinitiator, and the method includes the steps projecting light on the photoinitiator to activate the photoinitiator; and copolymerizing the first non-urethane-containing precursor with the second urethane-containing precursor and forming an adhesive copolymer to thereby attach the orthopedic joint implant to the joint in response to the activated photoinitiator. In some embodiments, the step of copolymerizing the first precursor with the second precursor includes projecting light for a time period less than about 2 minutes. In some embodiments, the step of projecting light includes projecting light discontinuously. In some embodiments, the step of projecting light includes projecting a blue light or a UV light. In some embodiments, the orthopedic joint implant includes a semi-transparent material, and the step of projecting light includes projecting light through at least a portion of the semi-transparent material.

Some embodiments include the step of placing a thermal inhibitor in the joint space.

In some embodiments, the first initiator includes a thermal initiator, and the method includes the step of polymerizing a portion of the first non-urethane-containing precursor in response to the thermal initiator to form a non-urethane-containing oligomeric molecule. In some such embodiments, copolymerizing includes copolymerizing the non-urethane-containing oligomeric molecule with the second precursor in response to the thermal initiator.

In some embodiments, the first initiator includes a photoinitiator, and the method includes the steps of placing a second initiator including a thermal initiator in the joint space; and projecting light on the photoinitiator to activate the photoinitiator; wherein copolymerizing includes copolymerizing a first portion of the first non-urethane-containing precursor with a first portion of the second urethane-containing precursor in response to the activated photoinitiator and copolymerizing a second portion of the first non-urethane-containing precursor with a second portion of the second urethane-containing precursor in response to the thermal initiator; thereby forming an adhesive copolymer including a non-urethane-containing portion based on the first precursor and a urethane-containing portion based on the second precursor.

In some embodiments, the method includes the step of placing a reaction accelerator in the joint space.

In some embodiments, the method includes priming the attachment surface of the implant with an organic solution, such as, e.g., acetone, prior to the contacting step.

In some embodiments, the method includes the step of swelling the orthopedic joint implant with a solvent prior to the applying step. In some embodiments, the method includes the step of forming an IPN or semi-IPN between the adhesive copolymer and the orthopedic joint implant.

In some embodiments, the method includes the step of removing a biological material from the joint prior to the contacting step.

In some embodiments, the method includes the step of interdigitating the adhesive copolymer in at least one of a feature, such as, e.g., at least one of a bump, a depression, a groove, a pore, and a space, on the attachment surface of the orthopedic joint implant and a feature on the joint surface. In some embodiments, the method includes the step of interdigitating the adhesive copolymer with cancellous bone.

In some embodiments, the attachment surface of the orthopedic joint implant includes a polyurethane IPN or polyurethane semi-IPN, the method includes the step of forming a non-covalent interaction, such as, e.g., least one of an absorption interaction, a crystallite formation, an entanglement, a hydrogen bond, a hydrophobic interaction, an ionic interaction, a pi-bond stacking, and a van der Waals interaction, between the adhesive copolymer and the polyurethane IPN or polyurethane semi-IPN. In some embodiments, the orthopedic joint implant includes a water-swellable IPN or a water-swellable semi-IPN, the method further includes interpenetrating a portion of the adhesive copolymer with the water-swellable IPN or water-swellable semi-IPN.

In some embodiments, the orthopedic joint implant includes an IPN or semi-IPN having a first phase domain, the method further includes the step of choosing a second precursor having a second phase domain configured to interfacially adhere to the first phase domain. In some such embodiments, the method includes the step forming a chemical bond, such as e.g. between the first phase domain and the second phase domain.

In some embodiments, the orthopedic joint implant includes an IPN or semi-IPN based on a polyether urethane having a hard segment based on methylene diphenyl diisocyanate, the method further includes the step of choosing a second precursor having a hard segment based on methylene diphenyl diisocyanate. In some embodiments, the orthopedic joint implant includes an IPN or semi-IPN based on a polyether urethane having a soft segment based on poly(tetramethyl) glycol, the method further includes the step of choosing a second precursor including a soft segment based on poly(tetramethyl) glycol.

Another aspect of the invention provides a method of attaching a first portion of a bone to a second portion of a bone. In some embodiments, the method includes the steps of applying a first non-urethane containing precursor, a second urethane-containing precursor, and a first initiator to the attachment surface of the orthopedic joint implant; and copolymerizing the first non-urethane-containing precursor with the second urethane-containing precursor and forming an adhesive copolymer to thereby attach the first portion of the bone to the second portion of the bone. In some embodiments, the step of forming an adhesive includes forming a biodegradable adhesive. In some embodiments, the step of applying a second urethane-containing precursor includes applying a precursor based on a lysine diisocyanate.

For purposes of this application, an "interpenetrating polymer network" or "IPN" is a material comprising two or more polymer networks which are at least partially interlaced on a molecular scale, but not covalently bonded to each other, and cannot be separated unless chemical bonds are broken. A "semi-interpenetrating polymer network" or "semi-IPN" is a material comprising one or more polymer networks and one or more linear or branched polymers characterized by the entanglement on a molecular scale of at least one of the networks by at least some of the linear or branched macromolecules. As distinguished from an IPN, a semi-IPN is a polymer composite in which at least one of the component polymer networks is not chemically crosslinked by covalent bonds. A "polymer" is a substance comprising macromolecules, including homopolymers (a polymer derived one species of monomer) and copolymers (a polymer derived from more than one species of monomer or macromonomer, in which the monomers and/or macromonomers are covalently linked to each other). "Phase separation" is defined as the conversion of a single-phase system into a multi-phase system, an example being the separation of two immiscible blocks of a block co-polymer into two phases, with the possibility of a small interphase in which a small degree of mixing occurs. A "urethane" is an ester of an N-substituted carbamic acid with the structure —RNHC(=O)OR'—, where R and R' are portions of a polymer chain joined by the "urethane linkage" which has the structure —NC(=O)O. A "polyurethane" is a material that contains multiple urethane linkages in its backbone. An "acrylic" functional group is a carbon-carbon double bond and a carbon-oxygen double bond, separated by a carbon-carbon single bond, with the carbon-carbon double bond rendering the group "ethylenically unsaturated". A "precursor" is a molecule which can undergo polymerization thereby contributing constitutional units to the essential structure of a polymer or copolymer.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 shows an orthopedic implant being attached to a surface of a joint according to one aspect of the invention.

FIGS. 2A-2B schematically illustrate the formation of an adhesive copolymer according to one aspect of the invention.

FIG. 6A shows components of existing dental and orthopedic products. FIG. 6B shows components of an adhesive according to one aspect of the invention.

FIG. 11 shows the composition of an adhesive mixture after polymerization to form an adhesive copolymer according to one embodiment of the invention.

FIG. 18A shows the chemical conversion occurring during the curing processes for adhesive copolymers made using thermal curing according to some embodiments of the invention.

FIG. 18B shows curing processes for adhesive copolymers made using blue light curing according to some embodiments of the invention.

FIG. 22 shows a summary of mechanical properties of an adhesive copolymer.

FIGS. 42A-42B shows another analysis of ultimate engineering strain and ultimate engineering stress of adhesive copolymers made with UDMA with different amounts of PTMO starting material.

FIGS. 43A-43B shows another set of results for peak peel initiation strength and peel propagation strength respectively, of adhesive copolymers made with UDMA with UDMA with different amounts of PTMO starting material adhered to a polyether urethane.

FIG. 44 shows a summary of various properties of adhesive copolymers made using different amounts of MMA monomer.

DETAILED DESCRIPTION

Figure 3C:
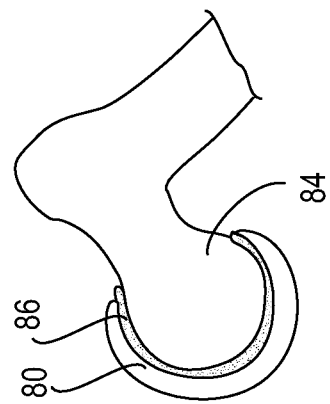
FIGS. 3A-3C show another view of an orthopedic implant being attached to a surface of a joint.
Figure 3B:
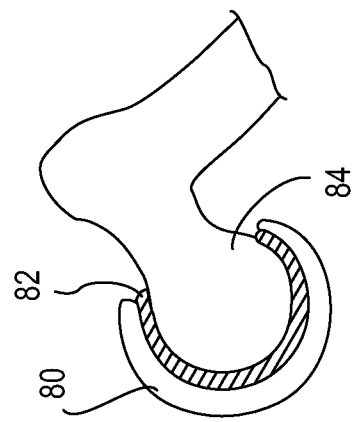
Figure 3A:
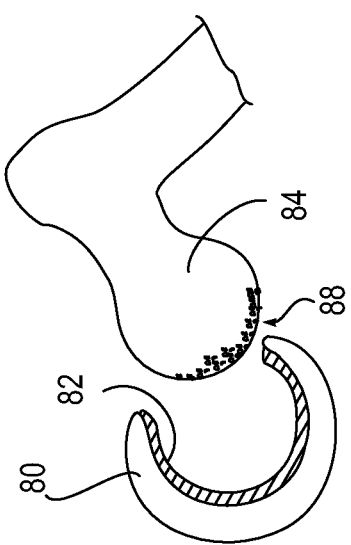

The present invention pertains to methods, compositions, and kits for adhering polymers and other materials to another material, and in particular to bone or bone-like structures or surfaces. It provides a thermal and/or lightcurable polymeric adhesive with excellent mechanical properties. The invention addresses a need in the art for anchoring polymer materials to other material surfaces for use in medical, commercial and industrial applications. These material surfaces may be either artificial (i.e., other polymer, metal, or ceramic compounds) or biologic tissues. A prime example of a biologic tissue is bone, either cortical or cancellous (porous). In particular, it addresses the need for robust fixation of a compliant orthopedic implant to bone through an easy-to-apply, biocompatible compound. In some embodiments, the polymer is a hydrated polymer (e.g., a hydrogel). In some embodiments, the polymeric orthopedic implant contains accessible chemical functional groups such as amine, hydroxyl, carboxyl, or urethane groups, or combinations of functional groups. It can have a homopolymer, copolymer, semi-interpenetrating or interpenetrating polymer network structure. It can also have a laminated structure comprising one or more of these, or a gradient IPN, semi-IPN, or co-polymer structure.

The invention also pertains to medical implants made with such polymers and their adhesion to bone and bone-like structures or surfaces. Some medical implants are formed with a lubricious bearing (articulating) surface designed to replace cartilage, and an attachment surface designed for fixation of the implant to bone for use in any joint in the body. The joint may be, for example a shoulder joint, a finger joint, a hand joint, an ankle joint, a foot joint, a toe joint, a knee medial compartment joint, a patellofemoral joint, a total knee joint, a knee meniscus, a femoral joint, an acetabular joint, a labral joint, an elbow, an intervertebral facet, or a vertebral joint. The device can be implanted on one side of joint forming a (hydrated) polymer-on-cartilage articulation in the mammalian joint. The device could further have a second mating component implanted on the opposing joint surface forming a (hydrated) polymer-on-(hydrated) polymer articulation. Alternatively, the device could further have a second mating component implanted on the opposing joint surface forming an articulation between a (hydrated) polymer on a metal or a ceramic.

Some embodiments of the polymeric adhesive provide fixation technology offer the advantage of a strong and secure bond to IPN or semi-IPN containing materials or devices. This enables a number of cartilage replacement applications. Conventional orthopaedic PMMA bone cement acts as a grout and relies on interdigitation with features on an implant (such as grooves), rather than actual adhesion, to secure the implant to bone. In some embodiments, the polymeric adhesive not only interdigitates with cancellous bone in the way that conventional PMMA bone cements do, it also provides direct adhesion to the anchoring surface of IPN or semi-IPN containing materials or devices.

FIG. 1 illustrates one embodiment of the invention. Medical implant 2 having a lubricious, hydrated articulation surface 10 and a stiff, attachment side 8 is fixed to bone 30 by means of an adhesive polymer 24 that acts as an intermediary between bone 30 and the attachment surface 6 of the implant 2. In the illustrated embodiment, the adhesive polymer mixture 4 is separate from the implant and can be applied to either the attachment surface 6 of the implant or to bone 30, such as using syringe 12. After the implant and bone are brought together and the adhesive polymer mixture is cured and hardened to form the adhesive polymer 24, the implant 20 is fixed to the bone. The mechanism of adhesion of the adhesive polymer 24 and the implant attachment surface 6 or the bone 30 is chemical and/or physical, with the chemical adhesion including, e.g., covalent bonds formed between reactive functional groups found on the device material or bone and the chemical groups in the adhesive polymer and/or a variety of non-covalent interactions such as absorption (e.g., chemisorption, physisorption), hydrophobic interaction, crystallite formation, hydrogen bonds, pi-bond stacking, van der Waals interactions and physical entanglements between the device and the cured adhesive copolymer (e.g., at the molecular level), mechanical interlocking. In some embodiments, the physical adhesion may be the result of in-filling or interdigitating of a bump(s), a depression(s), a groove(s), a pore(s), a rough area(s), a space(s) and/or other surface features. In some embodiments, the adhesive copolymer is interdigitated with cancellous bone. Some, all or none of the attachment surface may have features. In some embodiments, the attachment surface is smooth.

In some embodiments, the attachment surface of the orthopedic joint implant comprises one side of a gradient polyurethane (PU) IPN or gradient polyurethane (PU) semi-IPN (including a water swellable polyurethane IPN or semi-IPN), and the method further comprises forming a non-covalent interaction between the adhesive copolymer and the polyurethane IPN or semi-IPN.

One aspect of the invention includes a method of attaching an orthopedic joint implant to a joint, including placing an orthopedic joint implant in a joint space, the orthopedic joint implant having a bearing surface and an attachment surface adapted to attach the implant to a joint surface of a joint; applying a first, non-urethane containing precursor, a second, urethane-containing precursor, and a first initiator to the attachment surface of the implant; contacting the first precursor, the second precursor, and the first initiator with the joint surface; and copolymerizing the first, non-urethane-containing precursor with the second, urethane-containing precursor and forming an adhesive copolymer including a non-urethane-containing portion based on the first precursor and a urethane-containing portion based on the second precursor and to thereby attach the orthopedic joint implant to the joint.

A first precursor portion may be mixed with one or more other precursor portions to form a copolymer. A precursor portion may be in any form, such as a gel, a liquid, a paste, a putty, or an otherwise flowable material. In some embodiments, a precursor portion may include a solid, such as a bead, a grain, and/or a powder. A precursor portion may include, for example, one or more precursors, such as a monomer, a macromonomer, or a polymer, one or more initiators, one or more accelerators, one or more crosslinkers (e.g., bis-methylene-acrylamide), one or more fillers, one or more polymers one or more treatments, one or more radiopaque agents, and/or one or more solvents.

FIGS. 2A-2B illustrate one embodiment of the invention. A first, non-urethane-containing precursor 11 is mixed with a urethane containing precursor 13, along with an initiator (not shown) and the initiator is activated. In response to the activated initiator, the first precursor ("A") polymerizes with the second precursor ("B") to thereby form a copolymer with respect to the first and the second precursors.

In some embodiments, the first precursor may polymerize with itself. In other embodiments, the second precursor may also polymerize with itself. Thus, any type of copolymer may be formed, such as a block copolymer (AAABBBB), an alternating copolymer (ABABAB), or a statistical (random) copolymer (ABABBBA). Any number of "A" subunits (or any number of "B" subunits) may be present in each polymer region (block). Any number of copolymer strands may be present. A copolymer strand may start or end with either precursor or with the same precursors. Additional precursors (e.g. "C", "D", etc.) may also be included. The various combinations of A, B, C, D, etc. may form copolymers, including branch copolymers. A precursor may be any (e.g., a copolymer, a monomer, an oligomer, a polymer).

Referring to FIG. 2 B, in some embodiments, the copolymer may be crosslinked. In some embodiments, a crosslink(s) may be formed between two "A" subunits. In some embodiments, a crosslink(s) may be formed between two "B" subunits. In some embodiments, a crosslink may be formed between an "A" subunit and a "B" subunit. In some embodiments, a UDMA-based portion of a copolymer crosslinks an MMA based portion of a copolymer. Additional copolymer subunits may additionally self-crosslink, or crosslink with any other subunit.

The first precursor has a first chemical functional group that allows it to form a covalent bond with a second precursor which has a second chemical functional group to form a copolymer. The first precursor, as well as the second and any additional precursors, may have one, two, three, or four or more chemical functional groups. The first, second, and any additional chemical functional groups on a precursor may be the same or they may be different. Functional groups on different precursors may be the same or may be different. In some embodiments, a precursor has a chemical functional group that may form a covalent bond in response to a free-radical initiator or in response to another (e.g., an ionic/anionic) initiator. In some embodiments, a chemical functional group may be an unsaturated group, such as an ethylenically unsaturated group (e.g., a vinyl group). In some embodiments, a chemical functional group may be an acrylic group and may have a carbon-carbon double bond and a carbon-oxygen double bond separated by a carbon-carbon single bond. An "acrylic" functional group may, for example, be derived from an α,β-unsaturated carbonyl compound. A molecule containing an acrylic group may be decorated with additional chemical moieties. Examples of acrylic groups that can be used in the precursors include, but are not limited to acrylic acid, methacrylic acid, hydroxyethyl methacrylate, and methylmethacrylate. Examples of other ethylenically unsaturated groups that may be used in the precursors include acrylamides and methacrylamides (such as 2-Acrylamido-2-methyl-1-propanesulfonic, (3-Acrylamidopropyl)trimethylammonium chloride, N-Acryloylamido-ethoxyethanol, 3-Acryloylamino-1-propanol, N-tert-Butylacrylamide, Diacetone acrylamide, N,N-Dimethylacrylamide, N-[3-(Dimethylamino)propyl]methacrylamide, N-Diphenylmethylacrylamide, N,N'-Hexamethylenebis (methacrylamide), N-Hydroxyethyl acrylamide, N-(Hydroxymethyl)acrylamide, N-(Isobutoxymethyl)acrylamide, N-Isopropylacrylamide, N-Isopropylmethacrylamide, Methacrylamide, N-(3-Methoxypropyl)acrylamide, N-Phenylacrylamide, N-(Triphenylmethyl)methacrylamide, N-[Tris (hydroxymethyl)methyl]acrylamide), acid acrylates (such as Acryloyl chloride, 4-Acryloylmorpholine, [2-(Acryloyloxy) ethyl]trimethylammonium chloride, 2-(4-Benzoyl-3-hydroxyphenoxy)ethyl acrylate, Benzyl 2-propylacrylate, Butyl acrylate, tert-Butyl acrylate, 2-[[(Butylamino)carbonyl]oxy]ethyl acrylate, tert-Butyl 2-bromoacrylate, 4-tert-Butylcyclohexyl acrylate, 2-Carboxyethyl acrylate, 2-Chloroethyl acrylate, 2-(Diethylamino)ethyl acrylate, Di(ethylene glycol) ethyl ether acrylate, Di(ethylene glycol) 2-ethylhexyl ether acrylate, 2-(Dimethylamino)ethyl acrylate, 3-(Dimethylamino)propyl acrylate, Dipentaerythritol penta-/hexa-acrylate, Ethyl acrylate, 2-Ethylacryloyl chloride, Ethyl 2-(bromomethyl)acrylate, Ethyl cis-(β-cyano) acrylate, Ethylene glycol dicyclopentenyl ether acrylate, Ethylene glycol methyl ether acrylate, Ethylene glycol phenyl ether acrylate, Ethyl 2-ethylacrylate, 2-Ethylhexyl acrylate, Ethyl 2-propylacrylate, Ethyl 2-(trimethylsilylmethyl) acrylate, Hexyl acrylate, 4-Hydroxybutyl acrylate, 2-Hydroxyethyl acrylate, 2-Hydroxy-3-phenoxypropyl acrylate, Hydroxypropyl acrylate, Isobornyl acrylate, Isobutyl acrylate, Isodecyl acrylate, Isooctyl acrylate, Lauryl acrylate, Methyl 2-acetamidoacrylate, Methyl acrylate, Methyl a-bromoacrylate, Methyl 2-(bromomethyl)acrylate, Methyl 3-hydroxy-2-methylenebutyrate, Methyl 2-(trifluoromethyl)acrylate, Neopentyl glycol methyl ether propoxylate (2PO/OH) acrylate, Octadecyl acrylate, Pentabromobenzyl acrylate, Pentabromophenyl acrylate, Pentafluorophenyl acrylate, Poly(ethylene glycol) methyl ether acrylate, Poly(propylene glycol) acrylate, Soybean oil, epoxidized acrylate, 3-Sulfopropyl acrylate, Tetrahydrofurfuryl acrylate, 3-(Trimethoxysilyl)propyl acrylate, 5,5-Trimethylhexyl acrylate, 10-Undecenyl acrylate), acrylic acids and salts of acrylic acid (such as Acrylic acid anhydrous, 2-Bromoacrylic acid, 2-(Bromomethyl)acrylic acid, 2-Ethylacrylic acid, Hafnium carboxyethyl acrylate, Methacrylic acid, 2-Propylacrylic acid, Sodium acrylate, Sodium methacrylate, 2-(Trifluoromethyl)acrylic, Zinc acrylate, Zirconium acrylate, Zirconium bromonorbornanelactone carboxylate triacrylate, and Zirconium carboxyethyl acrylate), acrylonitriles (such as acrylonitrile, 1-Cyanovinyl acetate, and Ethyl 2-cyanoacrylate), bisphenol acrylics (such as Bisphenol A ethoxylate diacrylate, Bisphenol A glycerolate dimethacrylate, Bisphenol A glycerolate (1 glycerol/phenol) diacrylate, Bisphenol A dimethacrylate, and Bisphenol F ethoxylate (2 EO/phenol) diacrylate), fluorinated acrylics (such as 2,2,3,3,4,4,5,5,6,6,7,7-Dodecafluoroheptyl acrylate, 3,3,4,4,5,5,6,6,7,7,8,8,9,9,10,10,11,12,12,12-Eicosafluoro-11-(trifluoromethyl)dodecyl methacrylate, 3,3,4,4,5, 5,6,6,7,7,8,8,9,9,910,10,11,11,12,12,12-Heneicosafluorododecyl acrylate, 3,3,4,4,5,5,6,6,7,7,8,8,9,9,10,10,11,11,12,12, 12-Heneicosafluorododecyl methacrylate, 3,3,4,4,5,5,6,6,7, 7,8,8,9,9,10,10,10-Heptadecafluorodecyl methacrylate, 2,2, 3,3,4,4,4-Heptafluorobutyl acrylate, 2,2,3,3,4,4,4-Heptafluorobutyl methacrylate, 2,2,3,4,4,4-Hexafluorobutyl acrylate, 2,2,3,4,4,4-Hexafluorobutyl methacrylate, 1,1,1,3, 3,3-Hexafluoroisopropyl acrylate, 1,1,1,3,3,3-Hexafluoroisopropyl methacrylate, 2,2,3,3,4,4,5,5-Octafluoropentyl acrylate, 2,2,3,3,4,4,5,5-Octafluoropentyl methacrylate, 2,2, 3,3,3-Pentafluoropropyl acrylate, 2,2,3,3,3-Pentafluoropropyl methacrylate, 1H,1H,2H,2H-Perfluorodecyl acrylate, 2,2,3,3-Tetrafluoropropyl methacrylate, 3,3,4,4,5,5,6,6,7,7, 8,8,8-Tridecafluorooctyl acrylate, 2,2,2-Trifluoroethyl methacrylate, 1,1,1-Trifluoro-2-(trifluoromethyl)-2-hydroxy-4-methyl-5-pentyl methacrylate, and 2-[(1',1',1'-Trifluoro-2'-(trifluoromethyl)-2'-hydroxy)propyl]-3-norbornyl methacrylate), malemides (such as 2-[8-(3-Hexyl-2,6-dioctylcyclohexyl)octyl]pyromellitic diimide oligomer, maleimide terminated, 2-[8-(3-Hexyl-2,6-dioctylcyclohexyl)octyl]pyromellitic diimide oligomer, maleimide terminated, N,N'-(o-Phenylene)dimaleimide, N,N'-(1,3-Phenylene)dimaleimide, and N,N'-(1,4-Phenylene)dimaleimide), methacrylates (such as Allyl methacrylate, 2-Aminoethyl methacrylate, 2-[3-(2H-Benzotriazol-2-yl)-4-hydroxyphenyl] ethyl methacrylate, Benzyl methacrylate,Bis(2-methacryloyl)oxyethyl disulfide,2-(2-Bromoisobutyryloxy)ethyl methacrylate,2-(tert-Butylamino)ethyl methacrylate,Butyl methacrylate,tert-Butyl methacrylate, 9H-Carbazole-9-ethylmethacrylate, 3-Chloro-2-hydroxypropyl methacrylate,Cyclohexyl methacrylate,2-(Diethylamino)ethyl methacrylate, Di(ethylene glycol) methyl ether methacrylate,2-(Diisopropylamino) ethyl methacrylate,2-(Dimethylamino)ethyl methacrylate,2-Ethoxyethyl methacrylate,Ethylene glycol dicyclopentenyl ether methacrylate, Ethylene glycol methyl ether methacrylate,Ethylene glycol phenyl ether methacrylate,2-Ethylhexyl methacrylate, Ethyl methacrylate,Ferrocenylmethyl methacrylate, Furfuryl methacrylate, Glycidyl methacrylate, Glycidyl methacrylate, Glycosyloxyethyl methacrylate, Hexyl methacrylate,Hydroxybutyl methacrylate,2-Hydroxyethyl methacrylate,2-Hydroxyethyl methacrylate,Hydroxypropyl methacrylate,2-Hydroxypropyl 2-(methacryloyloxy)ethyl phthalate, Isobornyl methacrylate,Isobutyl methacrylate, 2-Isocyanatoethyl methacrylate,Isodecyl methacrylate, Lauryl methacrylate,Methacrylic acid N-hydroxysuccinimide ester, [3-(Methacryloylamino)propyl]dimethyl(3-sulfopropyl)ammonium hydroxide, [3-(Methacryloylamino)propyl] trimethylammonium chloride, Methacryloyl chloride purum, Methacryloyl chloride, [2-(Methacryloyloxy)ethyl] dimethyl-(3-sulfopropyl)ammonium hydroxide, 2-Methacryloyloxyethyl phosphorylcholine, [2-(Methacryloyloxy) ethyl]trimethylammonium chloride, [2-(Methacryloyloxy) ethyl]trimethylammonium methyl sulfate, 2-(Methylthio) ethyl methacrylate, mono-2-(Methacryloyloxy)ethyl maleate, mono-2-(Methacryloyloxy)ethyl succinate, 2-N-Morpholinoethyl methacrylate, 1-Naphthyl methacrylate, Pentabromophenyl methacrylate, Pentafluorophenyl methacrylate,Phenyl methacrylate, Phosphoric acid 2-hydroxyethyl methacrylate ester, Poly(ethylene glycol) behenyl ether methacrylate, Poly(ethylene glycol) 2,4,6-tris(1-phenylethyl)phenyl ether methacrylate, Poly(propylene glycol) methacrylate, Propyl methacrylate, 1-Pyrenemethyl methacrylate, Solketal methacrylate, Stearyl methacrylate, 3-Sulfopropyl methacrylate, TEMPO methacrylate, Tetrahydrofurfuryl methacrylate, 2,4,6-Tribromophenyl methacrylate, 3-(Trichlorosilyl)propyl methacrylate, Triethylene glycol methyl ether methacrylate, 1,1,1-Trifluoro-2-(trifluoromethyl)-2-hydroxy-4-methyl-5-pentyl methacrylate, 2-[(1',1', 1'-Trifluoro-2'-(trifluoromethyl)-2'-hydroxy)propyl]-3-norbornyl methacrylate, 3-(Trimethoxysilyl)propyl methacrylate, 3,3,5-Trimethylcyclohexyl methacrylate, (Trimethyl silyl)methacrylate, 2-(Trimethylsilyloxy)ethyl methacrylate, 3-[Tris(trimethylsiloxy)silyl]propyl methacrylate, and Vinyl methacrylate), and polyfunctional acrylics (such as Acrylamide: N,N'-Methylenebisacrylamide, 3-(Acryloyloxy)-2-hydroxypropyl methacrylate, Bis[2-(methacryloyloxy)ethyl] phosphate, Bisphenol A propoxylate diacrylate, 1,3-Butanediol diacrylate, 1,4-Butanediol, 1,3-Butanediol dimethacrylate, 1,4Butanedioldimethacrylate,N,N'(1,2Dihydroxyethylene)bisacrylamide, Di(trimethylolpropane) tetraacrylate, Diurethane dimethacrylate, N,N'-Ethylenebis(acrylamide), Glycerol 1,3-diglycerolate diacrylate, Glycerol dimethacrylate, Glycerol propoxylate 1,6-Hexanediol diacrylate, 1,6-Hexanediol dimethacrylate, 1,6-Hexanediol ethoxylate diacrylate, Hydroxypivalyl hydroxypivalate bis[6-(acryloyloxy)hexanoate], Neopentyl glycol diacrylate, Neopentyl glycol propoxylate, Pentaerythritol diacrylate monostearate, Pentaerythritol tetraacrylate, Pentaerythritol triacrylate, Poly(propylene glycol) diacrylate, Poly(propylene glycol) dimethacrylate, 1,3,5-Triacryloylhexahydro-1,3,5-triazine, Tricyclo[5.2.1.02,6]decanedimethanol diacrylate, Trimethylolpropane ethoxylate, Trimethylolpropane ethoxylate triacrylate, Trimethylolpropane ethoxylate triacrylate, Trimethylolpropane ethoxylate triacrylate, Trimethylolpropane propoxylate triacrylate, Trimethylolpropane triacrylate, Trimethylolpropane trimethacrylate, Tri(propylene glycol) diacrylate, and Tris [2-(acryloyloxy)ethyl] isocyanurate and salts and variations thereof. In some embodiments, urethane dimethyacrylate is used.

A precursor (e.g., with a chemical, functional group) may have any structure or any additional functional groups. In one embodiment, the first precursor is a monomer comprising an ethylenically unsaturated group and the second precursor is a macromonomer or oligomer containing ethylenically unsaturated end groups. In another embodiment, the first precursor is a monomer comprising an acrylic group and the second precursor is a macromonomer or oligomer containing acrylic end groups.

Figure 7:
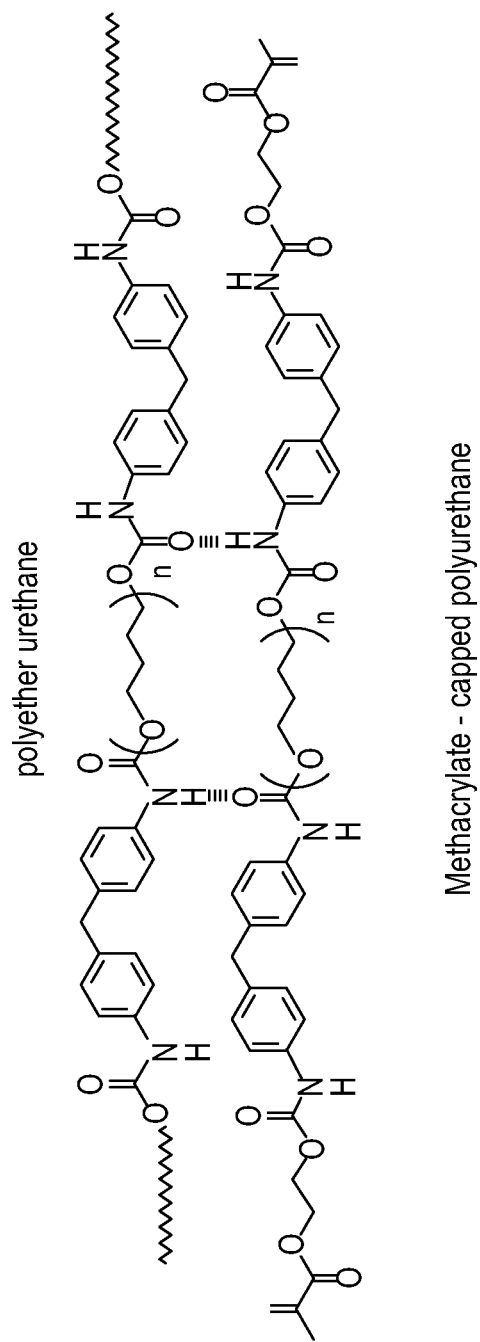
FIG. 7 shows interactions between a polyurethane-based adhesive polymer and a polyurethane material.

In some embodiments, a precursor may contain or may be capable of forming (e.g., with another precursor) a bond or interaction with a surface to which it may be attached. A precursor may be chosen to contain one or more subunits that are the same or similar to portions of a surface (e.g., subunits on a surface). A method may include choosing an adhesive precursor having a segment (e.g., a soft segment/phase such as based on PTMO, or a hard segment/phase such as based on MDI) that is based on the same material (segment or phase) present on an attachment surface. In some embodiments, segments from the adhesive copolymer may interfacially adhere with segments in the adhesive copolymer, such as by chemical bonds (e.g. hydrogen bonds) or any of the interactions described above. FIG. 7 shows hydrogen bonding (dashed lines) between Elasthane™ 75D (top) and the urethane portion of a methacrylate-capped polyurethane (e.g., UDMA) of a polymeric adhesive (bottom). The bonding may occur, for example, in the presence of a partial solvent, such as MMA. In one embodiment, the polymeric adhesive employs similar chemistry to Elasthane™ 75D, which comprises hard and soft urethane segments. In this embodiment, the polymeric adhesive was designed based on the chemical structure of Elasthane™ so that hydrogen bonding between urethane bonds of Elasthane™ and the polymeric adhesive was promoted to help achieve desired adhesion. It is speculated that the same type of hydrogen bonding that occurs between polyurethane (Elasthane™) chains, also occurs between Elasthane™ and the polymeric adhesive, and in particular for example, when the lengths and varieties of the hard and the soft segments have been chosen to be similar. The presence of MMA may also be important as it acts as a partial solvent for Elasthane™ and diffuses into it. While not wanting to be bound by any particular theory, it is hypothesized that this provides mobility to the Elasthane™ hard segments during curing, allowing more hydrogen bonds to form with the hard segments contained in the polymeric adhesive. MMA also improves wettability characteristics of the polymeric adhesive. In addition, it is speculated that MMA (or another precursor or another solvent) may partially penetrate a polyurethane or polyurethane-based hydrogel or other polymer and by polymerizing in situ, form hoops or loops or other entanglements with a polyurethane chain, a hydrogel chain, or another polymer chain. FIG. 7 depicts the hypothesized adhesive mechanism. In some embodiments, a segment of an adhesive precursor or adhesive copolymer has the same basic composition as a segment of an attachment surface to which the adhesive precursor is attached (or is prepared for attachment). In some embodiments, the overall length of an adhesive precursor (hard or soft) segment may be the same, similar, or may be different from the overall length of an attachment surface (hard or soft) segment. In some embodiments, an overall chain length between a hydrogen-bonding area of an adhesive precursor may be similar to the overall length between a hydrogen-bonding area of an adhesive precursor of an attachment surface.

An adhesive copolymer for medical use (e.g. as a medical adhesive) may be biocompatible or non-toxic or have low toxicity. In some embodiments, a precursor and/or a copolymer made from a precursor (e.g., for a non-medical use such as a non-medical adhesive, glue, or grout) may or may not be biocompatible or be non-toxic or have low toxicity.

In some embodiments, an adhesive copolymer may be tinted or colored. To detect polymeric adhesive that has been spilled or leaked outside (or inside) of the surgical area, some embodiments of the polymeric adhesive are a distinctive color, such as, a color not normally found in the body. Such coloring would make stray drops easily seen by a surgeon. An example of such coloring is through the use of trypan blue, which is a known, biocompatible surgical dye.

In some embodiments, a medical implant (e.g. an orthopedic device) may include a stiff backing comprising a biocompatible polyurethane IPN or polyurethane semi-IPN having soft segments based upon a first subunit and hard segments based upon a second subunit, and a precursor for an adhesive polymer may comprise the same (or similar) first subunits and/or second subunits.

In some embodiments, a (second) precursor may be or may be based on a urethane or polyurethane (e.g. a precursor may have one or more urethane linkages. A urethane linkage can be formed in any way, such as, for example, by the reaction of an isocyanate and a hydroxyl group. A urethane is described in the art as an ester of carbamic acid (or "carbamate esters"). For the purposes of this invention, and as is often done so in the art, the terms "urethane" and "carbamate" (as well as carbamate esters) are used interchangeably, such that polyurethanes are materials including multiple urethane (carbamate) linkages. In some embodiments, a polyurethane may also contain one or more other reaction products of an isocyanate(s), such as a urea linkage(s) which may be formed, for example, from the reaction between an isocyanate and an amine within their backbone, in which case it is referred to as a polyurethane urea. In some embodiments, a precursor (e.g. to be used with the urethane based precursor to generate an adhesive copolymer) may lack a urethane linkage (e.g., may be non-urethane-containing). In some embodiments, the first precursor that is lacking a urethane linkage does not generate a urethane linkage upon polymerization. In other words, it does not yield a polymer that contains urethane linkages in its backbone. In some embodiments, a first precursor may generate or contribute to the formation of a urethane linkage upon copolymerization.

In some embodiments, a first precursor comprises first precursor molecules having one acrylic group. In some embodiments, a second precursor comprises molecules having two acrylic groups. In some embodiments, the first precursor includes one acrylic group and no urethane linkages, and the second precursor includes two acrylic groups and one or more urethane linkages (e.g., one, two, three, four, five, or more than 5 urethane linkages).

Figure 4:
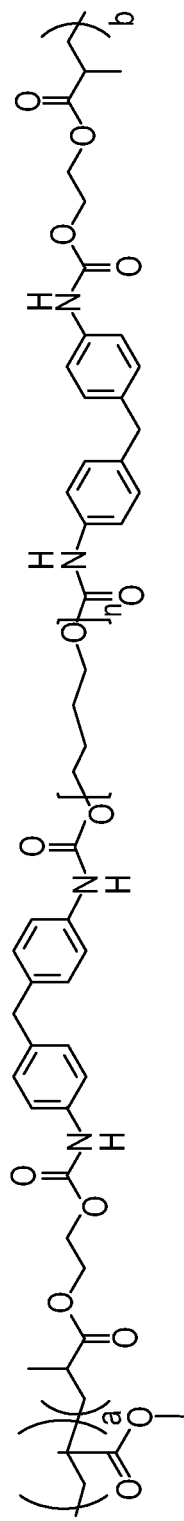
FIG. 4 shows the structure of an adhesive copolymer made according to one aspect of the invention.

FIG. 4 shows a urethane based adhesive copolymer according to one aspect of the invention. Any polyurethane or any polyether urethane based adhesive copolymer may be used. In one embodiment, Elasthane™ may be used as a polyether urethane based adhesive copolymer. In one embodiment, the adhesive comprises a methacrylate-capped polyether urethane (PEU) oligomer copolymerized with MMA as shown in FIG. 4.

Figure 5A:
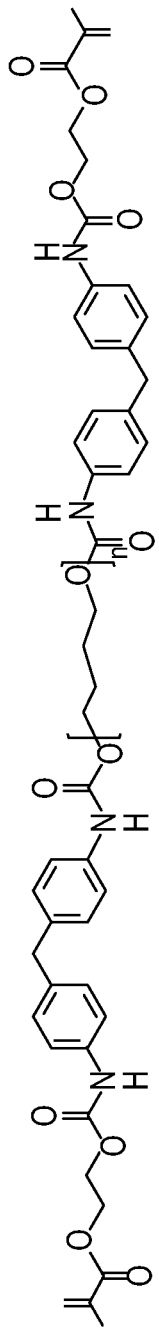
FIG. 5A shows an example of a chemical precursor that may be used to form an adhesive copolymer.

The urethane dimethacrylate-methyl methacrylate copolymer (e.g., a PMMA copolymer or PMMA-urethane copolymer) shown in FIG. 4 is made by copolymerizing a first precursor comprising a methyl methacrylate monomer (MMA) have an acrylic functional group and a second precursor comprising a urethane dimethacrylate monomer (UDMA), having two acrylic groups and a urethane linkage, as shown in FIG. 5A.

Figure 5D:
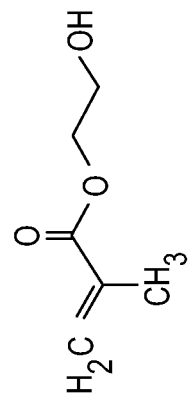
FIGS. 5B, 5C, and 5D show structures of chemicals that may be used to form a precursor such as the one shown in FIG. 5A.
Figure 5C:
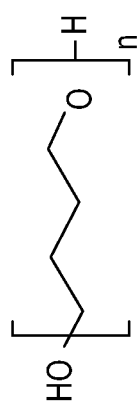
Figure 5B:
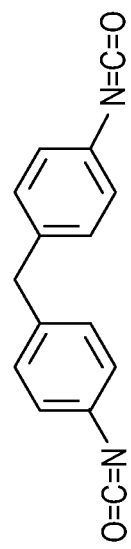

Other types of polyurethane oligomers can also be used, such as polycarbonate-based oligomers. In some embodiments, the PEU oligomer ("second precursor") may be made by reacting methylene diphenyl diisocyanate (MDI) (FIG. 5B) and poly(tetramethylene oxide) (PTMO) (FIG. 5C) in the first place and then capping the oligomer by reacting it with 2-hydroxyethyl methacrylate (HEMA) (FIG. 5D) to form acrylic functionalized end groups (e.g. methacrylate functionalized end-groups). An initiator (e.g. a UV initiator), such as 2-hydroxy-2-methylpropiophenone, may then be added, and/or a small amount of inhibitor, such as hydroquinone, may also be added to improve shelf life.

PTMO used to make a UDMA precursor may be of any molecular weight. In some embodiments, the PTMO may be from about 100 Da to about 5,000 Da. In some embodiments, the PTMO may be from about 400 Da to about 4000 Da, from about 400 Da to about 3000 Da, from about 400 Da to about 2000 Da, from about 400 Da to about 1200 Da, or from about 600 Da to about 1000 Da. In some embodiments, the PTMO is 250 Da. In some embodiments, the PTMO is 650 Da. In some embodiments, the PTMO is about 650 Da. In some embodiments, the PTMO is about 1000 Da. In some embodiments, PTMO molecules used to make a UDMA precursor are all the same or about the same size. In some other embodiments, the PTMO molecules used to make a UDMA precursor are different sizes. In some embodiments, the PTMO is a mixture of a first PTMO having a molecular weight about 650 Da and second PTMO have a molecular weight about 1000 Da. In embodiments in which more than one size of PTMO is used, any % ratio can be used. Any size of PTMO can be more than 10%, more than 20%, more than 30%, more than 40%, more than 50% of a mixture. In other embodiments, two or more species of UDMA may be made separately, and combined after manufacture.

Chemically speaking, UDMA molecules can be considered methyl methacrylate-terminated polyurethane chains. A methyl methacrylate-terminated polyurethane chains can be manufactured through an isocyanate-quenching and chain-terminating reaction to place methacrylate groups at both ends of a polyurethane. Chemical reactions that may take place include the acrylic free radical polymerization of MMA to form PMMA, polymerization of UDMA, copolymerization of MMA with UDMA, crosslinking of UDMA with PMMA, and self-crosslinking of UDMA. One view of the material is shown schematically in FIG. 2.

In some embodiments, UDMA alone may be polymerized to form a UDMA-based polymer adhesive. A UDMA-based polymer adhesive may be self-crosslinked. However, UDMA is a viscous oligomer that can be difficult to handle. Due to its high viscosity, the UDMA alone generally has limited surface wetting capabilities that, in turn, can limit its adhesion strength to IPN or semi-IPN containing materials. In addition, in some embodiments, a pure UDMA (post-crosslinking) polymer has a relatively low stiffness (E<100 MPa) that may be not high enough to bridge an IPN or semi-IPN containing material's-bone stiffness mismatch ($E_{IPN/semi-IPN\ containing\ material} \approx 35$ MPa, $E_{Bone} \approx 500\text{-}3500$ MPa). Stiffness bridging is important for some arthroplasty applications as it reduces the shear forces that are developed at the device-polymeric adhesive and polymeric adhesive-bone interfaces. (In other situations, stiffness bridging and the other limitations may not be an issue and a UDMA-based polymer may be a useful adhesive). In order to improve viscosity, an additional component (e.g. a polymer or a monomer that is able to polymerize with a urethane) may be added. Different amounts of a monomer, such as methyl methacrylate (MMA) may be added to different formulations. The more MMA, the less viscous the adhesive material is prior to curing. The viscosity of the adhesive prior to curing plays an important role in the proper application of the material during surgical implantation. For instance, the adhesive should be viscous enough to flow over a surface within a reasonable amount of time, but not so runny that it flows uncontrollably to undesired areas. Photoinitiator and inhibitor quantities can be adjusted accordingly. MMA copolymerizes with methacrylate-capped PU to form a new copolymer (FIG. 4) comprised of sections of PU and sections of PMMA. The final copolymer (PU PMMA) product has proven superior mechanical and adhesive properties than the PU oligomer alone in the uncured state.

UDMA (or other polyurethanes) and MMA mix very well and form a crosslinked UDMA-MMA copolymer that has good properties in terms of adhesion strength, stiffness and creep recovery. In addition, MMA is a partial solvent for Elasthane™ polyether polyurethanes and we hypothesize that this improves adhesion. The viscosity of the polymeric adhesive must also be considered so that the polymeric adhesive has good penetration into the cancellous bone pores (size: 200-1000 m). FIG. 11 demonstrates the final (post crosslinking) chemical composition of one embodiment of the cured polymeric adhesive as measured using various analytical techniques (FTIR, GC, TOC).

In some embodiments, an additional advantage of the described polymeric adhesive is low monomer release. Conventional PMMA bone cements are known to release MMA monomer into the body due to slow and incomplete polymerization. Early experiments have shown that the polymeric adhesive according to the disclosure has an initial MMA monomer release that is approximately two times lower than that of most conventional PMMA bone cements [6], believed to be in part due to crosslinking by the methacrylate-terminated UDMA macromonomers. In agreement with this data, an initial cytotoxicity assay (ISO 10993-5) yielded a score of 0 (0-nontoxic, 4-toxic) for one formulation of the described polymeric adhesive [8].

Any UDMA may be used. By UDMA is meant a urethane molecule made from any hard segment and usually two other chemicals (a soft segment, and a chain extender) each typically containing at least two hydroxyl groups (diol compounds) that form the basis of a UDMA structure. The UDMA can have any type of hard segment, soft segment, or chain extender. Any isocyanate can be used to form the hard segment (e.g. aliphatic or aromatic). Examples of materials that may be used include but are not limited to 1,5 napthalene diisocyanate (NDI), 2,6 tolyene diisocyanate or 2,4 toluene diisocyanate (TDI)3,3-bitoluene diisocyanate (TODI), cyclohexyl diisocyanate (CHDI), hexamethyl diisocyanate (HDI), isophorone diisocyanate (IPDI), methylene bis(p-phenyl) isocyanate, methylene diphenylisocyanate (MDI), and methylene bis (p-cyclohexyl isocyanate (H12MDI) and derivatives and combinations thereof. Any material can be used to form the soft segment. Examples of materials that can be used include but are not limited to hydrogenated polybutadiene. polyethylene oxide (PEO), hydroxy terminated butadiene, hydroxybutyl terminated polydimethylsiloxane (PDMS), hydroxyl terminated polyisobutylene, poly (1,6 hexyl 1,2 ethyl carbonate, polycaprolactone, polycarbonate, polyethylene adipate, polyhexamethylene carbonate glycol, polypropylene oxide (PPO), polytetramethylene adipate, poly(dimethylsiloxane), poly (tetramethylene oxide) (PTMO), and derivatives and combinations thereof. Any material may be used to form the chain extender portion. Examples of materials that may be used but are not limited to 1,4 butanediol, 4, 4'methylene bis (2-chloroaniline) (MOCA), ethylene diamine, ethylene glycol, and hexane diol and derivatives and combinations thereof.

In some embodiments, copolymerization includes a first initiator, and the first initiator comprises a photoinitiator, and the method further comprising projecting light on the photoinitiator to activate the photoinitiator; and copolymerizing the first, non-urethane-containing precursor with the second, urethane-containing precursor and forming an adhesive copolymer to thereby attach the orthopedic joint implant to the joint in response to the activated photoinitiator. Photopolymerization is widely and safely used in dental cement products. Any type of photoinitiator may be used, including, but not limited to acetophenone, benzophenone, benzoin ethyl ether, 4-benzoylbiphenyl, bisacrylphosphine oxide, 4,4'-bis(diethylamino)benzophenone, camphorquinone, 2-chlorothioxanthen-9-one, 4,4'-dihydroxybenzophenone, 4,4'-dimethylbenzil, ethylanthraquinone, 2-hydroxy-2-methylpropiophenone, 2,2-dimethoxy-2-phenylacetophenone, methybenzoylformate, monoacrylphosphine oxide, and phenylpropanedione. In some embodiments, a photoinitiator that has previously been used in the body such as in a bone cement or dental cement and appears to have long term biocompatibility may be chosen.

In one embodiment, the adhesive comprises low molecular weight polyurethane chains (25-99%), methyl methacrylate (MMA) monomer (0-75%), a polymeric photoinitiator (1-20%), and an inhibitor (1-500 ppm). The adhesive may be applied between the two materials to be bonded together, one of which is at least semi-transparent and allows light to pass through it.

Any amount of photoinitiator may be used that initiates (and propagates) copolymerization of the monomers. Between 0% to less than about 1%, to less than about 0.5%, to less than about 0.4%, to less than about 0.3%, to less than about 0.2%, or to less than about 0.1% photoinitiator may be used. More or less photoinitiator may be used for any reason as long as a copolymer can be made. An amount of photoinitiator may be chosen based on the stoichiometry of the reaction, and the amounts of the first precursor and second or additional precursors. For example, the amount of photoinitiator may depend on the MMA and UDMA content, since the molecular weights of MMA and UDMA are different. However, in some embodiments, a lower amount of photoinitiator may be used if for example, dual (hybrid) initiation including both photoinitiation and thermal (chemical) initiation are performed. A relatively higher amount of photoinitiator may be used if, for example, if an orthopedic joint implant, adhesive mixture, or other structure through which activating light must pass, has an opaqueness or otherwise reduces light transfer.

Light may be projected to activate the photoinitiator. Light may be projected for any length of time to cure or polymerize the adhesive precursor as needed. Light may be projected for between 0 seconds to about 10 seconds, to about 20 seconds, to about 30 seconds, to about 1 minute, to about 2 minutes, to about 3 minutes, to about 4 minutes, to about 5 minutes, to about 10 minutes. In some embodiments, light may be projected until the adhesive mixture has substantially entirely cured (e.g. for 10 seconds, 20 seconds, 30 seconds, 1 minute, 2 minutes, 3 minutes, 4 minutes, 5 minutes, or 10 minutes). In some embodiments, light may be projected continuously. In some other embodiments, light may be projected discontinuously, such as with one, two, three, or four or more than four on-off cycles. Each on cycle and each off cycle may be any length. A cycle may be the same time duration as another cycle, or may be a different time duration. A light may be projected discontinuously for any reason. A light may be projected discontinuously, for example, so as to start the polymerization process to increase an initial polymer mixture viscosity, allow time for implant or adhesive placement (e.g. in a joint), and then to further or complete the curing process after the implant is in place. A light may be projected discontinuously so as to control the polymerization rate, such as to reduce a speed of polymerization or reduce an amount of heat that is generated. A light may be projected with variable intensity so as to control a polymerization rate, such as to reduce a speed of polymerization or reduce an amount of heat generated. In some embodiments, intensity may start high and taper down, to, for example, reduce the polymerization rate and the amount of heat generated. In some embodiments, a high intensity burst may follow to ensure that conversion is sufficiently completed. In some embodiments, a temperature may be monitored (during polymerization), e.g., by infrared or contact thermometer. In some embodiments, an intensity of light can be adjusted, such as by a temperature-intensity feedback loop, so that the temperature does not exceed a physiologically relevant limit.

A light may be projected at any wavelength(s) that activates the photoinitiator. A projecting light may project ultraviolet light (UV), visible light, or infrared light. In some embodiments projecting light may comprise projecting UV light. In some embodiments projecting light may project blue light (e.g. between 400 nm and 500 nm; from 400 nm-420 nm, from 420 nm-440 nm, from 440 nm-460 nm, from 460 nm-480 nm, and/or from 480 nm-500 nm). In some embodiments, camphorquinone 1% w/w may be used as a photoinitiator in combination with an LED light source at 450 nm for photoinitiation. In some embodiments, the orthopedic joint implant comprises a semi-transparent material, and treating comprises projecting light through at least a portion of the semi-transparent material.

According to some embodiments, a method of copolymerizing an adhesive mixture includes copolymerizing the mixture in response to supplying a thermal or chemical initiator. Any thermal or chemical initiator may be used. In some embodiments, a thermal or chemical initiator is activated at the time it contacts an adhesive mixture. In some other embodiments, a thermal or chemical initiator may be activated by an electrical charge or elevated temperature. In other embodiments, a lower temperature may aid initiation. In other embodiments, an initiator may be present in a mixture, but may be prevented from activation by the action of an inhibitor.

In some embodiments, an adhesive mixture includes both a photoinitiator and a thermal initiator, or both initiators are applied along with an adhesive mixture (such as on a joint surface), and a method of copolymerizing an adhesive mixture includes copolymerizing the adhesive mixture in response to both an activated photoinitiator and a thermal initiator. Any one or more photoinitiators can be used at any step. Photoinitiators and chemical initiators may be chosen based on their solubility(ies) with the precursor solutions or other precursor materials. Initiators include, but are not limited to 2-hydroxy-2-methyl-propiophenone and 2-hydroxy-1-[4-(2-hydroxyethoxy) phenyl]-2-methyl-1-propanone, 2-oxoglutaric acid, azobisisobutyronitrile, benzoyl peroxide, camphorquinone, potassium persulfate, and sodium persulfate).

The composition and components for some embodiments of an adhesive precursor mixture, may include one or more of a first precursor (MMA), a second precursor (UDMA), a photoinitiator (camphorquinone), a thermal initiator (benzoyl peroxide), an accelerator (N,N-dimethyl-p-toludine), and an inhibitor (hydroquinone). The adhesive precursor mixture may be cured by photoinitiation and/or thermal initiation.

Long term biocompatibility is important for some embodiments of an adhesive copolymer, such as for use in the body in a joint implant. Although needing to perform very different functions, such as acid etching of tooth enamel and dentin, tolerating various forms of wear and abrasion after curing, matching thermal expansion of the tooth due to temperature changes, and maintaining an unchanging, aesthetically pleasing tooth color, use of certain materials in composite dental restoratives suggests they possess a long term biocompatibility that suggests they may be good choices for use in an adhesive copolymer, such as for attaching a orthopedic joint replacement to a joint surface.

Similarly, although existing bone cements have many limitations, especially for the purposes described herein, use of their components that appear to have shown long term biocompatibility or long term tolerance may be worthwhile. MMA, for example, has long been a component used in various bone cements.

FIGS. 6A-B show commercial products (dental adhesive cements, dental cavity liner, and orthopedic bone cement) that also contain constituents of an adhesive mixture made according to one aspect of the invention and that may have long term biocompatibility. In some embodiments, an inhibitor and/or accelerator may be added to a precursor mixture, in part, because it appears to have long term biocompatibility.

Two (or more) types of initiators may be applied for any reason that improves the polymerization reaction. A first initiator may control a viscosity of the material, may allow only partial curing to take place, or may allow only a portion of adhesive to attach. For example, use of a first photoinitiator may render an adhesive mixture more viscous and easier to handle. Use of a first photoinitiator may allow a user to place an implant in a preferred position, and to quickly cure the implant in the preferred position. The reaction may be very fast (less than 10 seconds, less than 20 seconds, less than 30 seconds, less than a minute, less than 2 minutes, or less than 3 minutes. Selective use of a first initiator may allow an implant to be put into position (such as on a joint surface) and attached to the surface, while a second initiator may attach the implant to a second surface (such as an attachment surface).

Using two types of initiators may increase the amount of monomer polymerized and thereby reduce undesired monomer release from the adhesive polymer (e.g., into a body of a patient). Using a second method of curing (e.g., thermal) after a first method of curing (e.g., photoinitiation) may allow areas of the adhesive mixture that are not sufficiently penetrated by a light source to be photocured to polymerize in response to thermal initiation.

One aspect of the invention provides a composition of matter comprising a urethane dimethacrylate-methyl methacrylate copolymer comprising a plurality of first polymer regions based on urethane dimethacrylate alternating with a plurality of second polymer regions based on methyl methacrylate to thereby form the urethane dimethacrylate-methyl methacrylate copolymer. In some embodiments, the urethane regions (the urethane dimethacrylate regions or modified urethane dimethacrylate regions) comprise about 60%

(w/w) to about 80% (w/w), about 60% (w/w) to about 90% (w/w), about 60% (w/w) to about 99% (w/w), or about 70% (w/w) to about 90% (w/w) of the adhesive copolymer. In some embodiments, the methyl methacrylate regions comprise from about 20% (w/w) to about 40% (w/w), from about 1% to about 20% (w/w), or from about 1% (w/w) to about 40% (w/w). In some embodiments, the UDMA regions include soft segments based on PTMO, and the soft segments have a molecular weight between about 100 Da and about 5000 Da. In some embodiments, the UDMA-MMA copolymer defines a compressive modulus between about 30 MPa and about 2000 Mpa. In some embodiments, the UDMA-MMA copolymer defines a tensile modulus between about 30 MPa and about 2000 Mpa. In some embodiments, the UDMA-MMA copolymer defines a failure strain between about 25% and 200%. As well as providing other advantages, such as excellent fixation capabilities and mechanical strength, UDMA combined with PMMA reduces the brittleness otherwise found in pure PMMA.

An accelerator may accelerate the decomposition of an initiator, for example to generate a free radical. Any type of accelerator(s) may be used, including but not limited to N,N-dimethyl-p-toluidine, N,N-dimethylaniline, N,N-dimethylaminobenzyl alcohol, N,N-dimethylaminobenzyl methacrylate, 2-(Dimethylamino)ethyl methacrylate, ethyl 4-(dimethylamino)benzoate, and 3,4-methylenedioxybenzene methoxyl methacrylate.

In some embodiments, a method of attaching an orthopedic joint implant to a joint includes the step of priming the attachment surface of the implant prior to contacting the surface of the implant with adhesive precursors. Priming the surface may include priming the surface with an organic solvent (e.g., acetone).

In some embodiments, a method of attaching an adhesive copolymer to a medical implant includes the step of swelling the implant with a solvent prior to applying the precursors to the implant. In some embodiments, at least a portion of the implant comprises a polyurethane, and any solvent that swells the polyurethane, but does not dissolve it may be used. The solvent is chosen based on the specific qualities and phases of the polymers and monomers. For instance, acetic acid is capable of swelling, but does not dissolve many polyurethanes. Other solvents that can be used include, but are not limited to, acetone, butanol (or any alkyl alcohol), dichloromethane, dimethylacetamide, diethylether, dimethylformamide, dimethylsulfoxide, methanol, propanol, tetrahydrofuran or combinations of these. Taking into account the solubilities in the phases of the polymer, solvents with varying degrees of swelling can be chosen. Solubilities of the solvents and components of the material to be swollen can be obtained from polymer textbooks such as The Polymer Handbook or can be measured experimentally. In some embodiments, an IPN or semi-IPN is formed between the adhesive copolymer and the orthopedic joint implant, such as after partially swelling the orthopedic joint implant with a solvent.

Figure 8A:
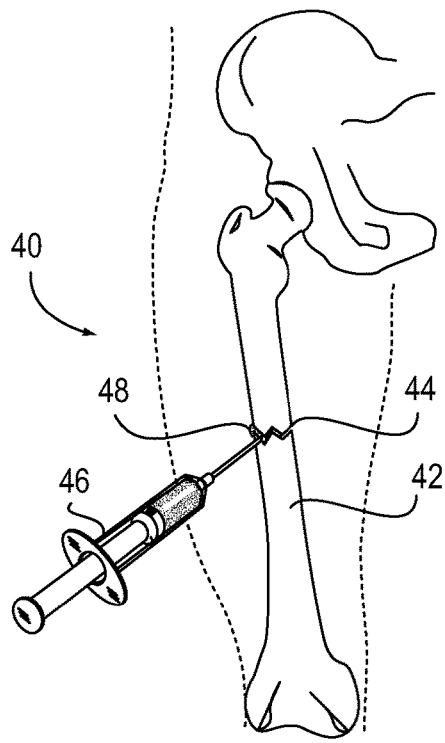
FIGS. 8A-8B shows a biodegradable adhesive copolymer being used to set a bone according to one aspect of the invention.
Figure 8B:
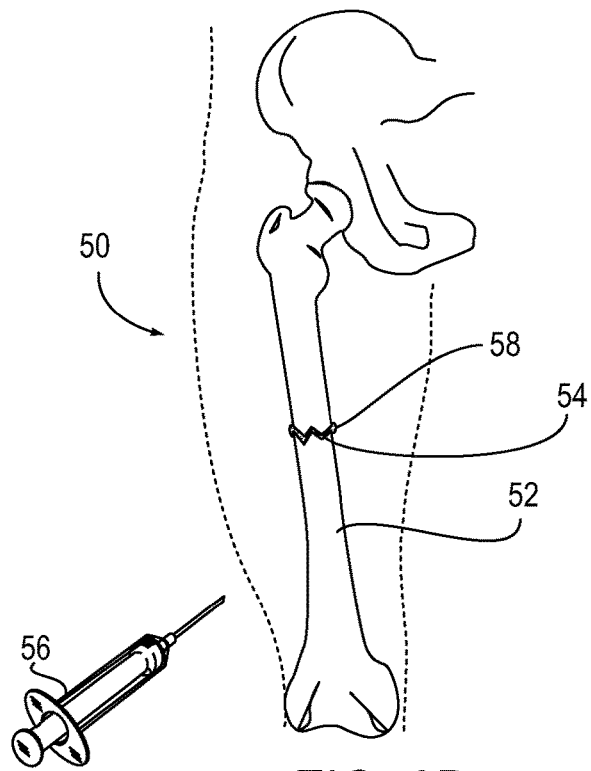
Figure 8C:
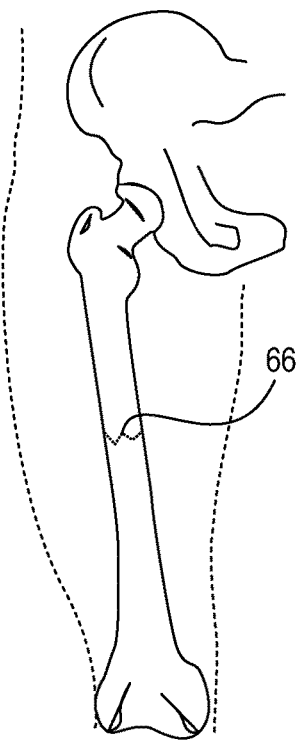
FIG. 8C shows the bone after the adhesive copolymer has biodegraded.

One aspect of the invention provides a method of attaching a first portion of a bone to a second portion of a bone, including the steps of applying a first, non-urethane-containing precursor, a second, urethane-containing precursor, and a first initiator to the attachment surface of the orthopedic joint implant; and copolymerizing the first precursor with the second precursor and forming an adhesive copolymer to thereby attach the first portion of the bone to the second portion of the bone. FIGS. 8A-C illustrate use of an adhesive copolymer to help set a bone. Patient 40 has a break in bone 42, exposing bone surface 44. A biodegradable adhesive precursor mixture 48 is premixed in syringe 46 and applied to the surface. In FIG. 8B, bone 52 of patient 50 is set by a layer of cured adhesive 58 after syringe 56 is removed. In FIG. 8C, the biodegraded adhesive has biodegraded and the new bone tissue 66 has grown into the region of the previous break to mend the break. A biodegradable adhesive may be based on, for example, a second urethane-containing precursor based on a lysine diisocyanate segment. A biodegradable adhesive may be degraded by, for example, contact with oxygen and/or with a body fluid such as, for example, blood, interstitial fluid, saliva, or urine.

One aspect of the invention provides a composition of matter including between 60% to 99% (e.g. 60% to 80%) urethane dimethacrylate monomer, between 1% to 40% (e.g. 20% to 40%) methyl methacrylate monomer, between 0% to 1% (w/w) initiator (e.g. a photoinitiator, a thermal initiator), between 0% and 1% accelerator; and between 0% to 0.01% inhibitor. composite adhesive combines the desirable ductility of polyurethane with the stiffness and strength of PMMA bone cement.

The relative concentrations of polyurethane chains and MMA monomer can be varied to alter the physical, mechanical and chemical properties of the adhesive. The composition may further include from 1% to 70% poly(methyl methacrylate powder). PMMA may provide useful properties while reducing the relative amount of unreacted monomer. In some embodiments, the initiator is camphorquinone or benzoyl peroxide. In some embodiments, the accelerator is hydroquinone. Any additional components mentioned herein may be added, such as an antibiotic or radiopaque material. Barium sulfate and iohexol (an iodine contrast agent) may be added to the adhesive to increase its radioopacity. In some embodiments, the composition defines a viscosity between about 1 Pa·s and about 5000 Pa·s.

At their contact interface, a polyurethane-based implant will form molecular entanglements and both physical and chemical bonds with the polyurethane-based adhesive, in spite of the fact that the device is a polyurethane-PAA composite and the adhesive is comprised of a polyurethane-MMA composite. Bonding is facilitated in particular by the common polyurethane component in both materials. For example, a gradient IPN or semi-IPN of PU and PAA will feature one side with a preponderance of PU relative to PAA, and this side would bond well with the UDMA-MMA composite adhesive. The invention provides a unique combination of polyurethane polymer chains and an MMA monomer in a UV-curable adhesive that has sufficient mechanical properties for orthopaedic, medical, commercial, and industrial applications that have high mechanical demands.

One aspect of the invention provides a kit or packaged components. The kit may be used to make an adhesive copolymer. A kit may contain the components in any combination that do not copolymerize before mixing, and that would, upon mixing, form an adhesive copolymer as described herein. In some embodiments, the components are packaged in two parts, Part A and Part B, that can be mixed together prior to use.

A kit may include a first reservoir comprising a first mixture including at least one of a urethane dimethacryate monomer and a methyl methacrylate monomer, at least one of a photoinitiator and a chemical initiator; and an inhibitor; a second reservoir comprising a second mixture comprising: at least one of a urethane dimethacrylate monomer and a methyl methacrylate monomer; an accelerator; wherein at least the first reservoir or the second reservoir comprises a urethane dimethacrylate monomer and at least the first reservoir or the second reservoir comprises a methyl methacrylate; and an instruction for use.

In some embodiments, both the first and the second reservoirs comprise a urethane dimethacrylate monomer and a methyl methacrylate monomer. In some embodiments, the second reservoir comprises an inhibitor. In some embodiments, the kit further includes poly(methyl methacrylate), such as a PMMA powder. The PMMA powder may be, for example from about 1% to about 70%, about 10% to about 60%, about 20% to about 50%, or about 30% to about 40% of the total weight of the components (the combined weight of the components of the first reservoir, the components of the second reservoir, and the PMMA). The poly(methyl methacrylate) may be any form and may be in one of the above mentioned reservoirs, or may be in a third reservoir. The PMMA (or the other components) may be in the form of a gel, a liquid, a powder, a putty, or a solid.

In some embodiments, a kit may include one or more additional components, such as an accelerator, an additive configured to prevent an infection (e.g., an anti-fungal treatment or an antibiotic), a filler, one or more initiators, a radiopaque material. In some embodiments, additional monomers or polymers. In some embodiments, the additional components may copolymerize with the UDMA and the MMA.

Figure 9A:
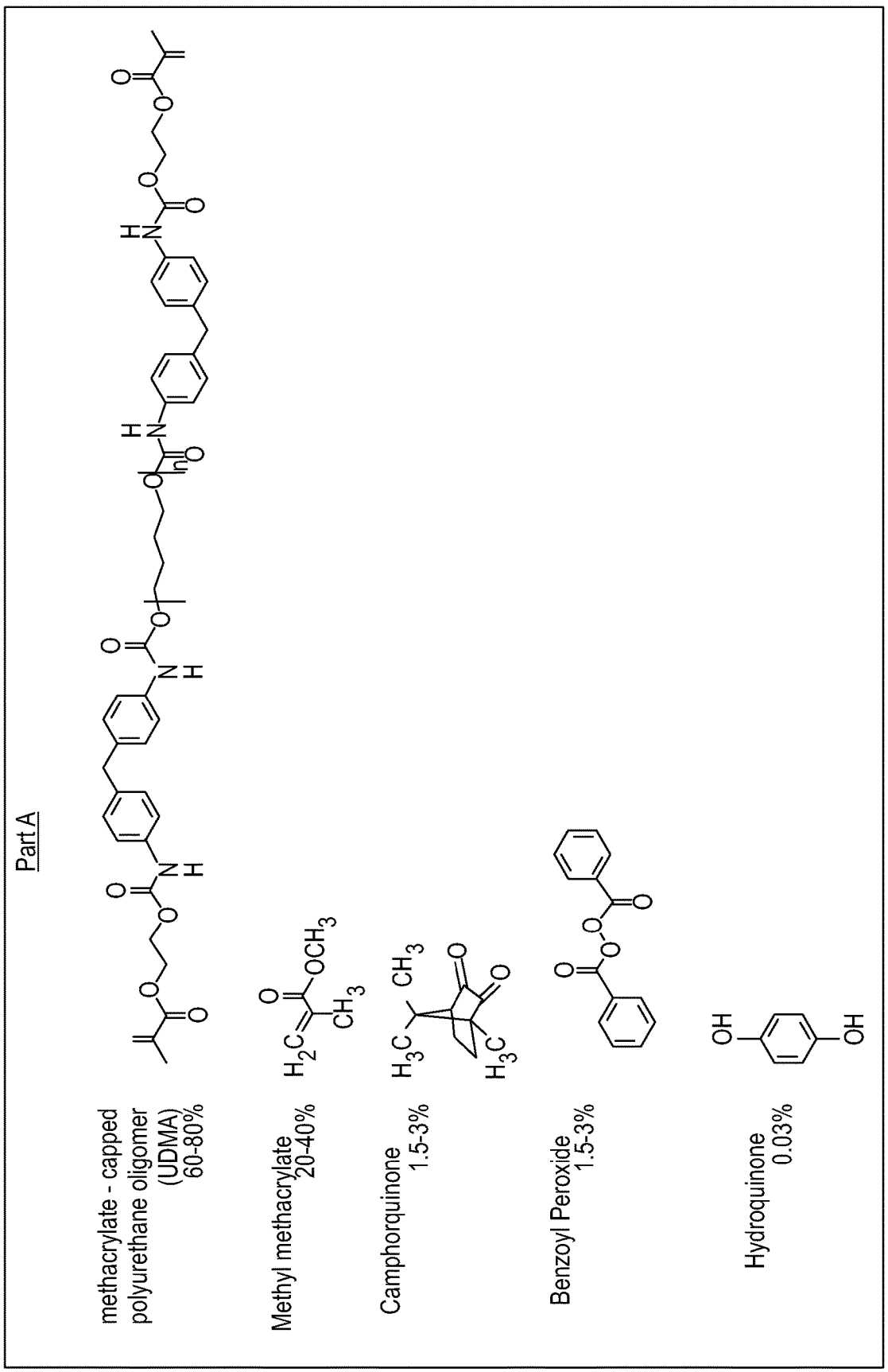
FIGS. 9A-9B show an embodiment of a two part adhesive kit that can be used to make an adhesive copolymer according to one aspect of the invention.
Figure 9B:
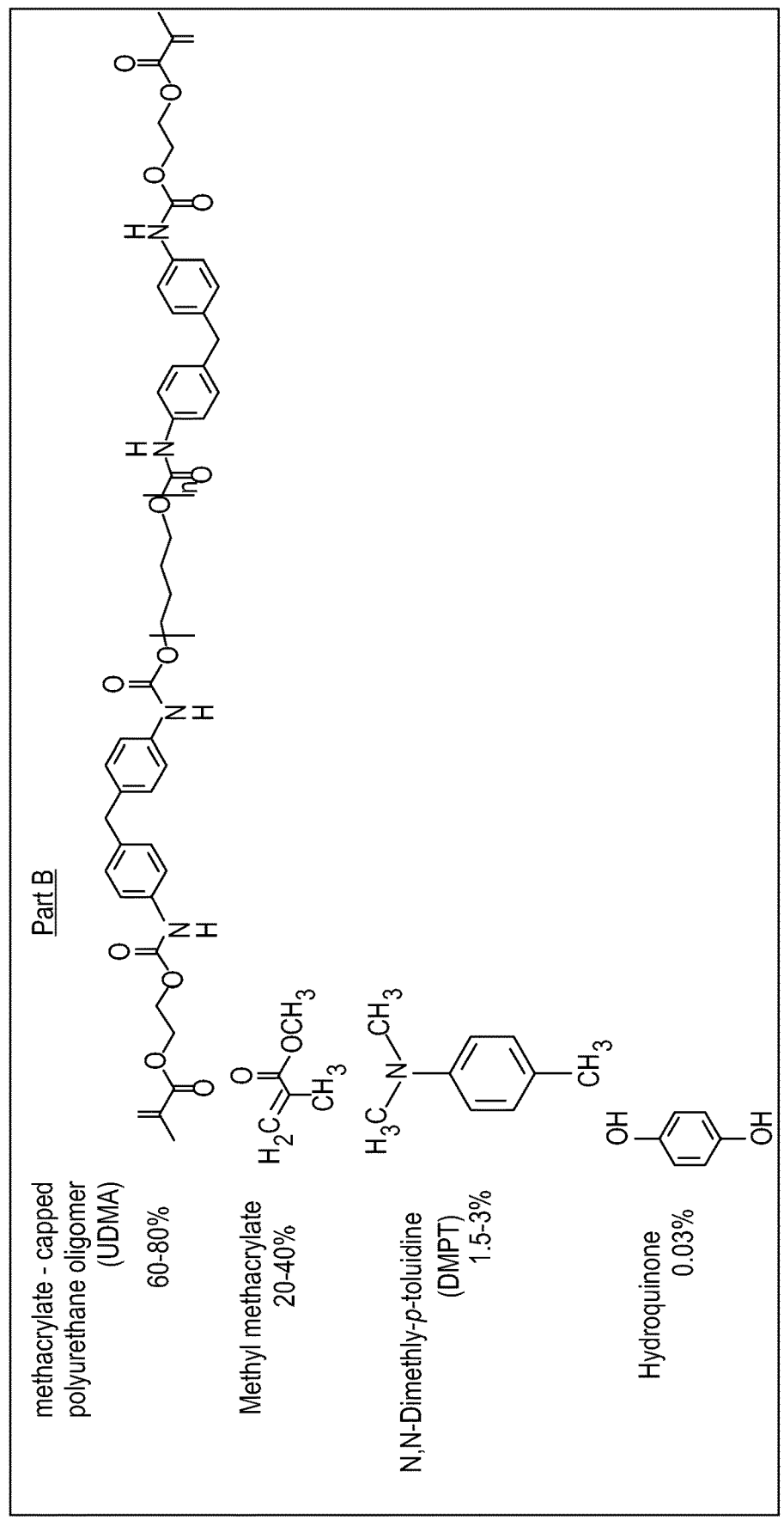

FIGS. 9A-B show an example of components for an adhesive copolymer kit. Both Parts contain the base materials (UDMA and MMA), and Part A contains the initiators while Part B contains the accelerator. In other embodiments, one or the other of the Parts may contain the UDMA and/or the MMA and/or other components in any combination that prevents premature polymerization. This polymeric adhesive hybrid formulation allows for fast curing (120 s) using blue light (450-470 nm) via a photoinitiator (Camphorquinone), but it also allows for slower curing (5-20 min) due to the thermal/chemical initiator—accelerator combination (Benzoyl Peroxide and N,N-Dimethyl-p-toluidine). Therefore, areas that have not been adequately exposed to blue light are subsequently fully cured even in the absence of light. A kit may have any amounts of components described herein.

Figure 10:
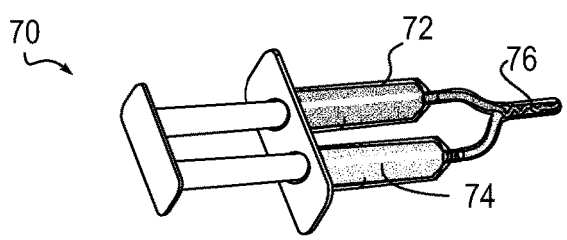
FIG. 10 shows an embodiment of a two part adhesive according to one aspect of the invention.

In some embodiments, a kit may include a syringe having two reservoirs and the syringe may be useful for dispensing an adhesive mixture into a bone, joint, or other space or onto a surface (e.g. it may have a needle or nozzle). FIG. 10 shows syringe 70 with a first reservoir with a first mixture 72, and a second reservoir with a second mixture 74. The syringe includes a chamber 76 for combining or mixing the contents of the first and second reservoirs together. In one embodiment, the two parts are packaged in a two-barrel syringe (25 mL per barrel) and configured to be mixed (mixing ratio 1:1) just before use using a long (8 in) mixing nozzle tip.

In some embodiments, the first mixture defines a viscosity between about 1 Pa·s and about 5000 Pa·s, or between about 1000 Pa·s and about 4000 Pa·s, or between about 2000 Pa·s and about 3000 Pa·s.

EXAMPLES

Example 1

This is a prophetic example. A cartilage replacement material comprising an interpenetrating polymer network of polyetherurethane and cross linked sodium polyacrylate was bonded to cancellous bone. Suitable cartilage materials are described, e.g., in U.S. application Ser. No. 12/499,041 and in U.S. application Ser. No. 13/219,348, the disclosures of which are incorporated herein by reference. The adhesive comprised low molecular weight polyetherurethane chains (60%), methyl methacrylate (MMA) monomer (30%), an acrylated benzophenone photoinitiator (10%), and hydroquinone (200 ppm). The polyurethane chains are made from of poly(tetramethylene oxide) (PTMO), methylene diphenyl diisocyanate (MDI), and hydroxyacrylate (HEA) or hydroxyethyl methacrylate (HEMA). The adhesive (viscous liquid) was applied between the tissue replacement material and the cancellous bone. To cure the adhesive, UV light was applied to the adhesive by shining the light through the tissue replacement material for 10 minutes. The adhesive chemically bonded to the tissue replacement material and was anchored to the cancellous bone via penetration into and subsequent solidification within the bone pores.

Adhesive materials according to embodiments of this invention have the characteristic advantages of attaining the following characteristics simultaneously: (1) high tensile and compressive strength, (2) high tensile and compressive modulus, (3) the ability to chemically bond to polyurethane and PMMA substrates, and (4) the ability to fix compliant implants to bone and other biological tissues through rapid curing with exposure to UV light. An example of said compliant implant is a cartilage replacement device or resurfacing prosthesis that takes the place of damaged articular cartilage in the body and reconstitutes the low friction, load bearing properties of hyaline cartilage in mammalian joints. Any joint containing cartilage can be resurfaced with a compliant bearing material anchored with the adhesive described in this invention. The adhesive can also be used to anchor replacement materials for fibrocartilaginous structures (such as the meniscus) or other load-bearing structures in the body such as bursae.

Many parameters may be varied when preparing the adhesive compositions of this invention, such as the conditions of polymerization (i.e. ambient oxygen, UV intensity, UV wavelength, exposure time, temperature), polyurethane constituents, crosslinking density, molecular weight of precursor polymers, and relative weight percent of polymers.

Example 2

Three adhesives were formulated comprising low molecular weight polyetherurethane chains (60%), methyl methacrylate (MMA) monomer (30%), an acrylated benzophenone photoinitiator (10%), and hydroquinone (200 ppm). The polyurethane chains were made from poly(tetramethylene oxide) (PTMO), methylene diphenyl diisocyanate (MDI), and hydroxyacrylate (HEA) or hydroxyethyl methacrylate (HEMA). Adhesive 1 had PTMO 650 MW and PTMO 1000 MW of 50%-50%; Adhesive 2 had PTMO 1000 MW 100%; and Adhesive 3 had PTMO 650 MW 100%.

Figure 12:
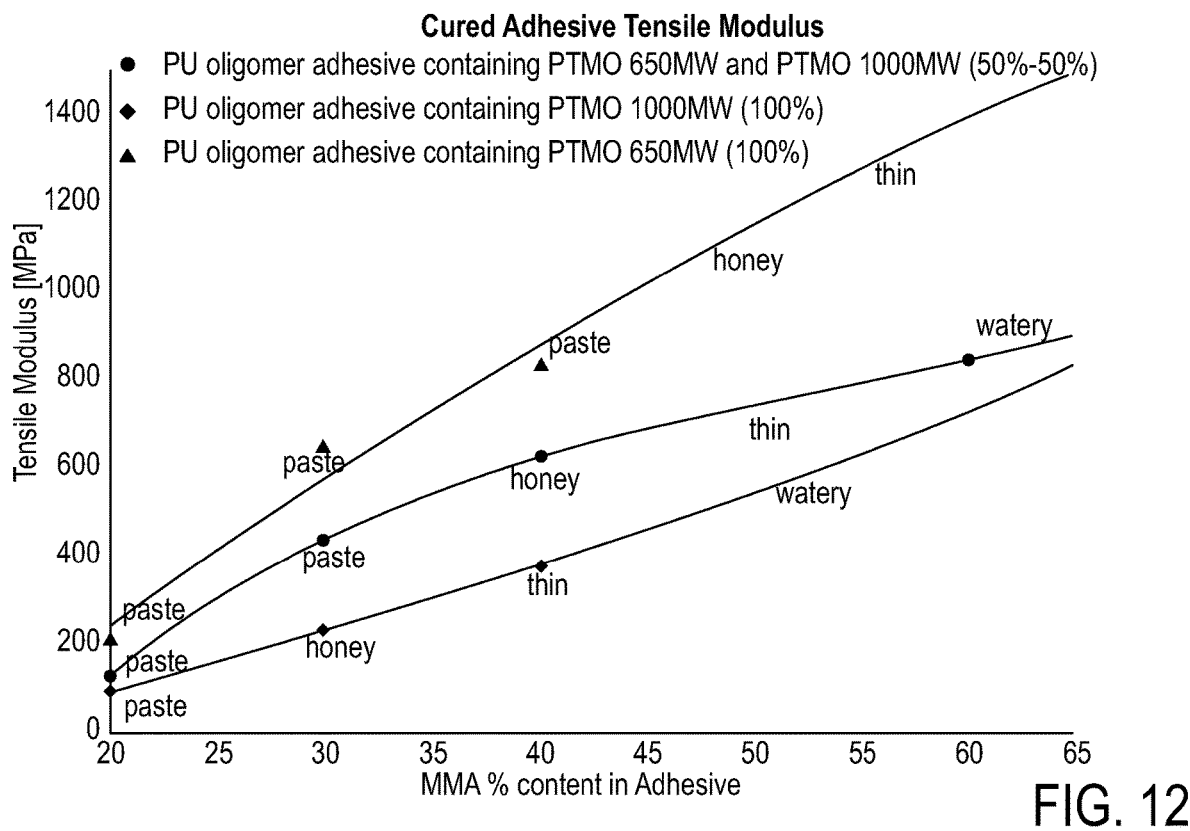
FIGS. 12 and 13 show tensile properties of different compositions of adhesive copolymers made according to some embodiments of the invention.

The tensile properties of Adhesives 1-3 were measured using dogbone sample according to ASTM D638-IV. FIG. 12 shows the tensile modulus at a stress of 2 Mpa of the new adhesives, with Adhesive 1 data represented by circles, Adhesive 2 data represented by diamonds, and Adhesive 3 data represented by triangles. As shown, addition of MMA increases the tensile stiffness of the adhesive, reaching values as high as 900 MPa. Other formulations can go even higher in stiffness. It also shows that lower molecular weight (MW) of the polyurethane chains (Adhesive 3) leads to higher stiffness than higher MW chains (Adhesive 2).

Figure 13:
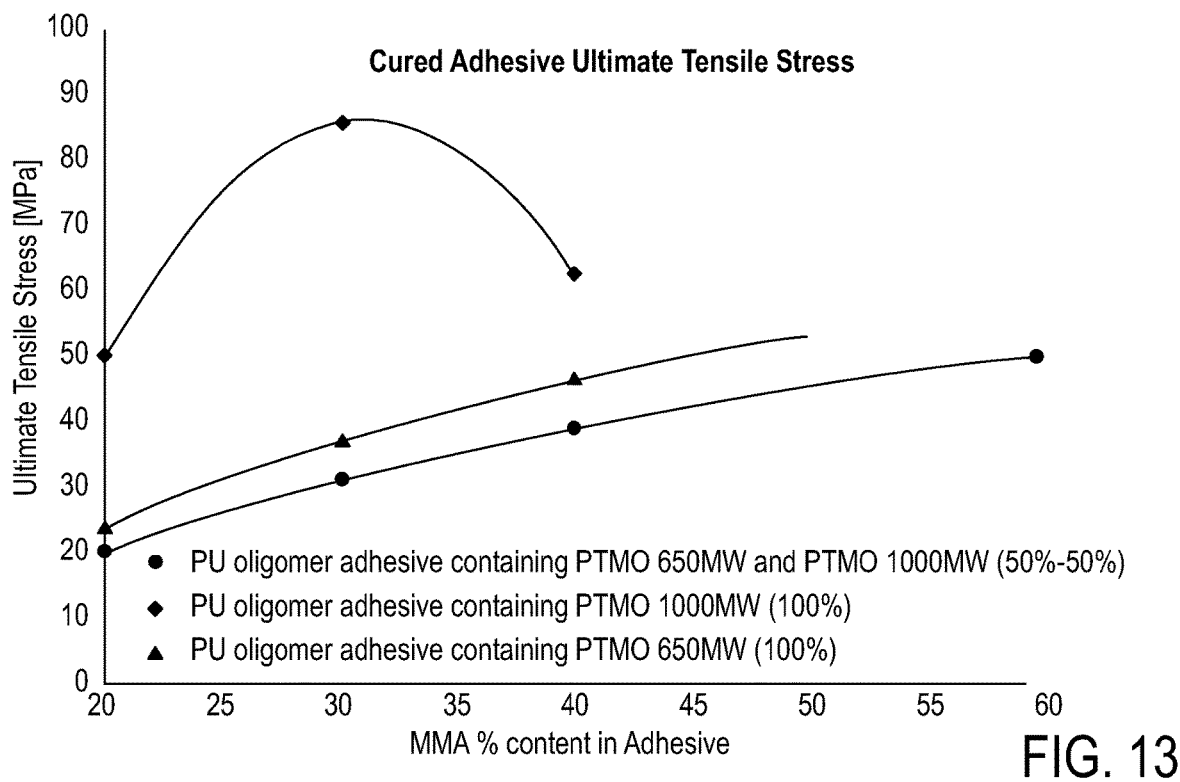

FIG. 13 shows the ultimate tensile strength of the new adhesives, with Adhesive 1 data represented by circles, Adhesive 2 data represented by diamonds, and Adhesive 3 data represented by triangles. As shown, addition of MMA renders the material stronger in tension. Again, lower MW polyurethane chains tends to yield stronger (higher ultimate tensile stress) materials for MMA content >=30%.

Example 3

Figure 14:
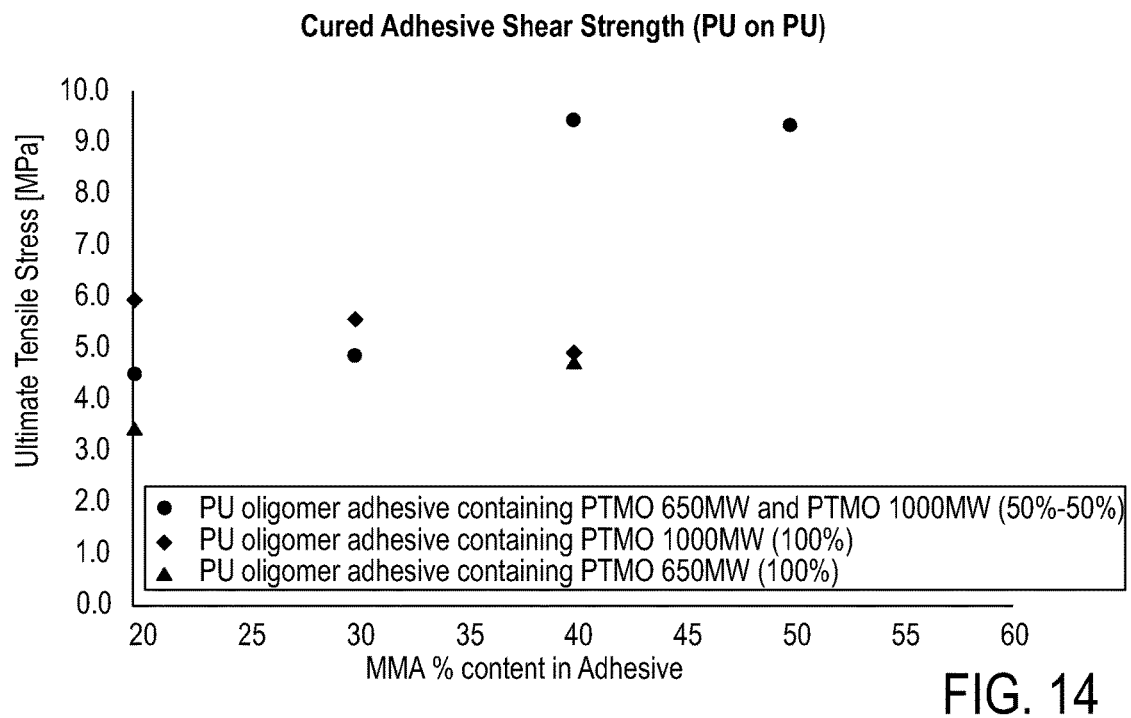
FIG. 14 shows shear strength results of adhesive copolymers such as those used in FIGS. 12 and 13 adhered to a polyurethane.

A lap shear test was conducted after bonding two sheets of Elasthane 75D polyetherurethane using Adhesives 1, 2 and 3 above. As described above, the three different adhesive formulations differ by polyurethane soft segment chemistry (molecular weight MW of PTMO chains). The results are shown in FIG. 14, with Adhesive 1 data represented by circles, Adhesive 2 data represented by diamonds, and Adhesive 3 data represented by triangles. As shown, Adhesive 1, having a mixed MW (50%-50% PTMO 650 MW PTMO 1000 MW) yields superior shear strength.

Example 4

Figure 15:
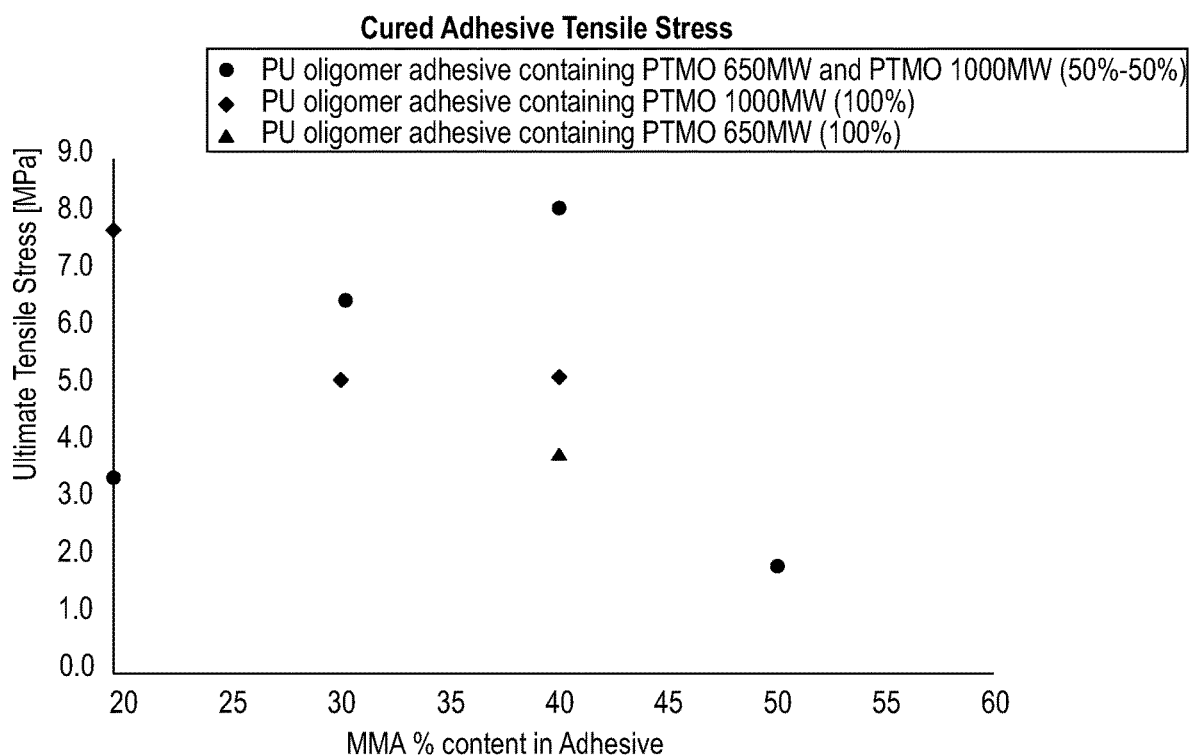
FIG. 15 shows shear strength of adhesive copolymers such as those used in FIGS. 12-14 adhered to a bone.

A lap shear test was conducted after bonding a sheet of polyetherurethane to cancellous bone with Adhesives 1, 2 and 3 above. As described above, the three different adhesive formulations differ by polyurethane soft segment chemistry (molecular weight MW of PTMO chains). The results are shown in FIG. 15, with Adhesive 1 data represented by circles, Adhesive 2 data represented by diamonds, and Adhesive 3 data represented by triangles. As shown, shear strength values range from 3-8 MPa with failure usually occurring within the bone itself rather than the adhesive or the adhered material.

Example 5: An Exemplary Synthesis Procedure of the UDMA for One Embodiment of the Polymeric Adhesive The chemical composition of urethane dimethacrylate (UDMA) may be tailored to match the polyurethane structure of the anchoring surface of an IPN or semi-IPN containing material or device. More specifically, in some embodiments, the IPN or semi-IPN containing material or device has an anchoring surface comprised of Elasthane™ 75D, a medical poly-ether-urethane. Elasthane™ 75D is an MDI (4,4-Methylenebis(phenyl isocyanate)) based polyurethane that contains PTMO (poly(tetramethyl) glycol) of molecular weight 650 Da as the soft segment and BD (2-Butene-1,4-diol) as the chain extender. In some embodiments, the UDMA in the polymeric adhesive closely matches the structure of Elasthane™ 75D by employing the same hard and soft segments (FIG. 9). To facilitate cross-linking, the UDMA is terminated with HEMA (2-Hydroxyethyl methacrylate) (FIG. 9). This similarity between the polymeric adhesive and Elasthane™ 75D is key to the adhesive capability of polymeric adhesive as we hypothesize that hydrogen bonds between the hard segments of the Elasthane™ and the polymeric adhesive are formed, developing a strong adhesive force.

UDMA Synthesis Steps (200 g batch). Raw materials used in the formulation of UDMA. MDI, PTMO, and HEMA are obtained from Sigma-Aldrich.

1. Using a 1-liter 3-necked round bottom flask equipped with mechanical stirring and $N_2$ purging line, add 0.219 mol pre-dried (at 60° C. overnight in a vacuum oven) MDI. Turn on the $N_2$ purging, and then submerge the flask in a 60° C. water bath. Wait for 30 min to allow the MDI to melt.

2. Add 0.107 mol pre-dried (at 60° C. overnight in a vacuum oven) PTMO (Mw: 650-1000 Da) via an addition funnel over 30 min while maintaining vigorous stirring. If the PTMO freezes in the funnel, heat it up with a heat gun to maintain the addition speed. Continue stirring for 60 min after adding the PTMO.

3. Add 0.225 mol HEMA via an addition funnel in one batch. Continue stirring for 4 h.

4. At the end of the reaction, add 0.1 wt % of hydroquinone based on the total weight of synthesized cement. Stir for 10 min before storing the synthesized UDMA in the refrigerator.

Example 6: Synthesis of the Polymeric Adhesive

Some embodiments of the polymeric adhesive can be formulated by mixing synthesized UDMA with the desired amount of MMA and other ingredients, such as initiator and accelerator. The mixing procedure of an example based on 30 wt % MMA, 1 wt % camphorquinone (photoinitiator), 1 wt % benzoyl peroxide (thermal initiator), and 1 wt % N,N-dimethyl-p-toluidine (accelerator) formulation (PUA-50-30-CQ1.0-BP1.0-DMPT1.0) [nomenclature used here and throughout is the following, or based on the following: PUA-% of PTMO 650 (remainder is PTMO 1000-% MMA content-photoinitiator-photoinitiator concentration (w/w)-thermal initiator-thermal initiator concentration (w/w)-accelerator-accelerator concentration (w/w)—other/optional constituent—other/optional constituent concentration-Lot #] is given below:

Part A a. Add 20 g of synthesized UDMA into a capped 50-mL centrifuge tube.

b. Add 0.596 g camphorquinone (CQ), 0.506 g benzoyl peroxide (BP), and 8.935 g MMA into a capped 20-mL glass vial. Gently shake the vial until the CQ and BP dissolve completely.

c. Add the MMA mixed with initiators into the centrifuge tube containing UDMA; vigorously stir with a mechanical stirrer for 5 min to ensure thorough mixing.

Part B d. Weigh 20 g of synthesized UDMA in a capped 50-mL centrifuge tube (tube B).

e. Add 0.596 g N,N-dimethyl-p-toluidine (DMPT) and 8.935 g MMA into a capped 20-mL glass vial. Gently shake the vial until the DMPT dissolves completely.

f. Add the MMA mixed with accelerator into the centrifuge tube containing UDMA (tube B); vigorously stir with a mechanical stirrer for 5 min to ensure thorough mixing.

Packaging g. Degas both vials using light centrifugation.

h. Slowly pour Part A into one cartridge of the dual syringe and Part B into the other cartridge. Cap the syringe and install pistons. Wrap the syringe with aluminum foil and store it upright.

The polymeric adhesive is now ready to use, which can be cured via photo and/or thermal initiation. The polymeric adhesive can be formulated with either CQ or BP alone, which are the light-cure only or thermo-cure only versions, respectively.

Sterilization

As a proof-of-concept, a high-viscosity formulation of one embodiment of the polymeric adhesive (PUA-50-30-CQ1.ACC1) has been successfully filtered. Using a pressure of approximately 100 psi, the polymeric adhesive was passed through a 0.2 μm filter (hydrophilic, Fluoropore, Millipore) at room temperature. The experience was that the filter needed to be pre-wetted with a low-viscosity polymeric adhesive (PUA-50-60) before filtration could be performed with the higher viscosity formulation. The polymeric adhesive cured after filtration.

Example 7: Curing Duration

Figure 16:
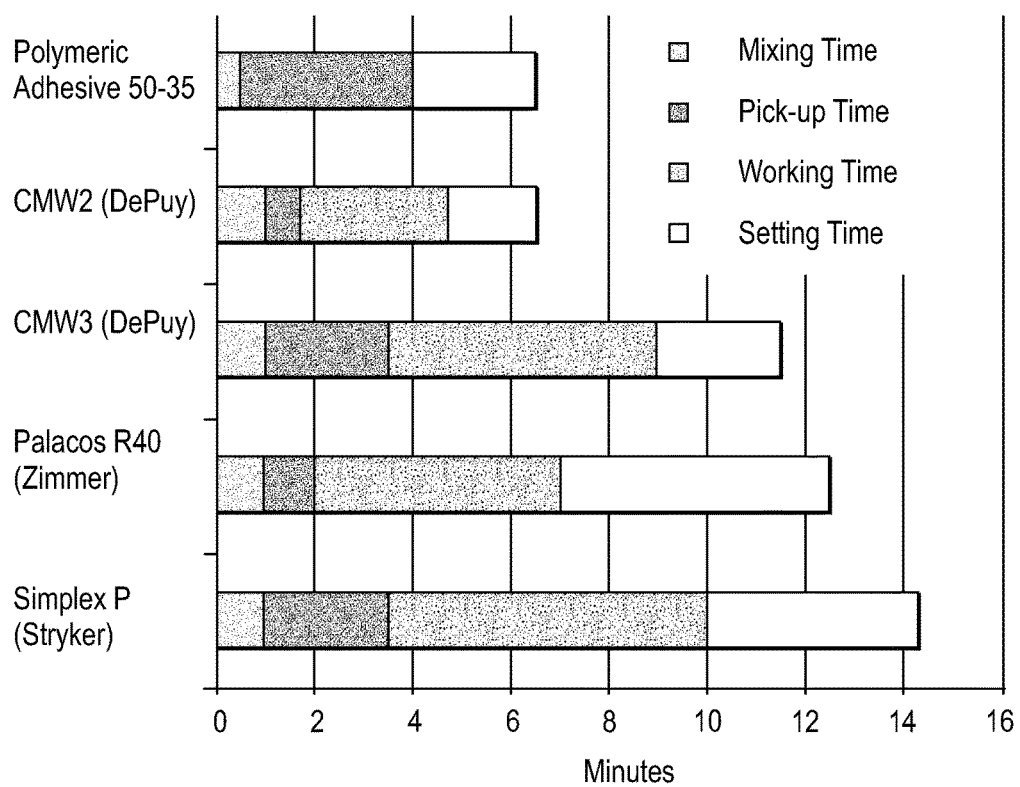
FIG. 16 shows the curing times for adhesive copolymers made according to some embodiments of the invention compared with curing times for PMMA bone cements.

As with other orthopaedic and dental cements, the curing dynamics of the described polymeric adhesives can be adjusted by altering the concentrations of the initiators and accelerators. For curing with blue light, one embodiment of the polymeric adhesive has been designed to cure within 2 min. For thermal curing, one embodiment of the polymeric adhesive has been designed to have doughing (i.e. working) and setting times (as defined in ASTM F451-08) in the range seen for PMMA bone cements (FIG. 16). These result in full curing of the polymeric adhesive within 20 min without light exposure (see next section). The current short working/setting time is desired for some applications, but finalized surgical instrumentation and procedure may require a longer working time.

Curing dynamics for several PMMA bone cements and the described polymeric adhesive (thermal cure only, no light exposure). The data for CMW, Palacos, and Simplex P were obtained from a CMW brochure [10] and show times at 18° C. The data for the polymeric adhesive (PUA-50-35-CQ1.1-BP0.95-DMPT1.1) was estimated from a preliminary study performed at room temperature (~23° C.) that did not fully conform to the test method described in ASTM F451-08. (The values for the polymeric adhesive have been estimated from a preliminary study).

Example 8: Conversion Study Using ATR-FTIR

In some embodiments of the polymeric adhesive, the main component is structurally similar to commercially available UDMA. Thus, the rationale of conversion calculation for UDMA that was previously reported in the literature [9] was followed. In the FTIR spectrum, the stretching absorption of the vinyl C=C in UDMA and MMA appears at 1637 $cm^{-1}$ and the stretching absorption of the aromatic C=C in UDMA appears at 1598 $cm^{-1}$. The aromatic C=C absorbance is used as a standard to which the vinyl C=C absorbance is normalized. The conversion is calculated by the following equation:

$$DC = \left[1 - \frac{(A_{C=C}/A_{Ar})_{polymer}}{(A_{C=C}/A_{Ar})_{monomer}}\right] \times 100\%$$

where DC is the degree of double bond conversion, $(A_{c=c}/A_{Ar})_{polymer}$ is the ratio of vinyl C=C absorbance to aromatic C=C absorbance in the cured polymeric adhesive, and $(A_{c=c}/A_{Ar})$monomer is the ratio of vinyl C=C absorbance to aromatic C=C absorbance in the uncured polymeric adhesive.

Figure 17:
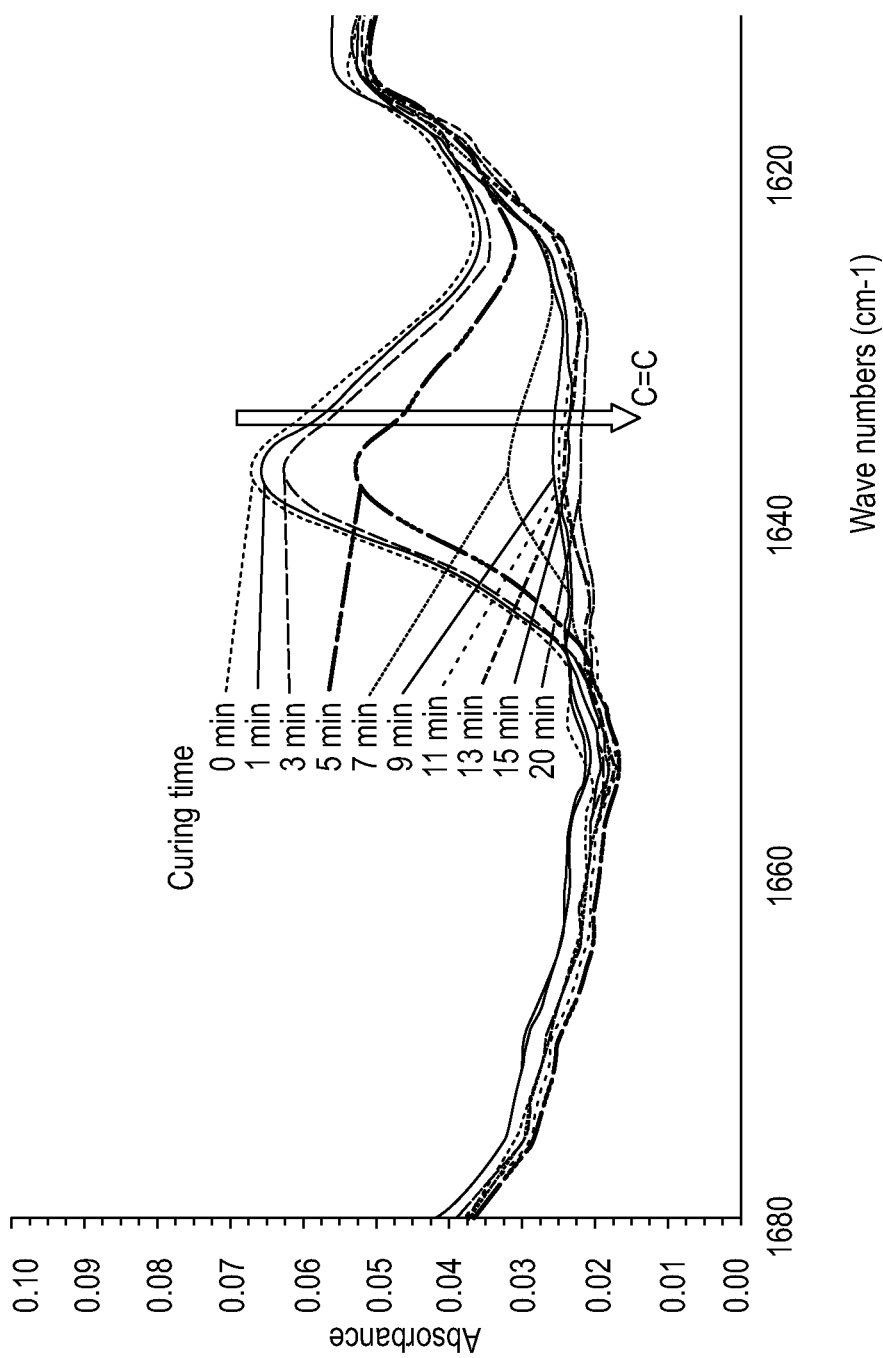
FIG. 17 shows FTIR curing processes for adhesive copolymers made using thermal curing according to some embodiments of the invention.

FIG. 17 shows FTIR spectra of the thermally cured polymeric adhesive at different curing times (0-20 min).

FIG. 17 shows the thermal curing process of PUA-50-30-CQ1.0-BP0.85-DMPT1.0-Lot #26 at room temperature. The disappearance of the vinyl C=C peak over time indicates an increasing conversion. Depending on the baseline correction mode, full spectrum baseline correction or partial baseline correction, the calculated conversion differs by about 20% at the end of curing, as shown in FIG. 18A. FIG. 18A shows the degree of C=C bond conversion vs. time for the polymeric adhesive PUA-50-30-CQ1.0-BP0.85-DMPT1.0-Lot #26 via only thermal curing.

Example 9

The conversion of the polymeric adhesive cured by blue light was also studied based on this method, using the same polymeric adhesive. Due to the fast polymerization rate of blue light curing, we only conducted the conversion study on a fully cured sample, which was cured for 2 min. The results are summarized in FIG. 18B. FIG. 18B shows the Degree of C=C conversion of the polymeric adhesive PUA-50-30-CQ1.0-BP0.85-DMPT1.0-Lot #26 cured by blue light. Three techniques for signal baseline correction (BSL) were evaluated. The full baseline correction takes the entire spectrum into account while the partial baseline correction only uses a region of the spectrum.

Example 10: Leaching Properties

A leachables analysis was conducted on some embodiments of the polymeric adhesive samples, and results were compared to samples of Stryker® Simplex® P PMMA bone cement. Samples were incubated in ultrapure water and leachables were evaluated by measuring the carbon and nitrogen content in the water with a TOC/TC machine. Following the rationale of ASTM F451-08, samples were made in a mold so that leaching could only occur from one surface of defined surface area. To simulate a worst-case scenario, the polymeric adhesive samples (PUA-50-30-CQ1.3-DMPT1.0) (n=2) were placed in the ultrapure water before blue light curing (2 min). After mixing the Simplex® P according to the manufacturer's recommendations, samples (n=2) were placed in the molds and submerged in ultrapure water 4 min after mixing began. Because MMA monomer is the main leachable for PMMA bone cement, and theoretically the main leachable for the polymeric adhesive, the amount of leached MMA monomer was calculated from the carbon content of the ultrapure water, assuming all carbon was from MMA. In addition, to remove volatiles from the solutions (i.e., MMA monomer), solutions were dried in an oven and remaining carbon and nitrogen were re-dissolved in ultrapure water. The carbon and nitrogen content was determined and compared to the initial measurements to determine amount of volatiles in the leachables.

Figure 19A:
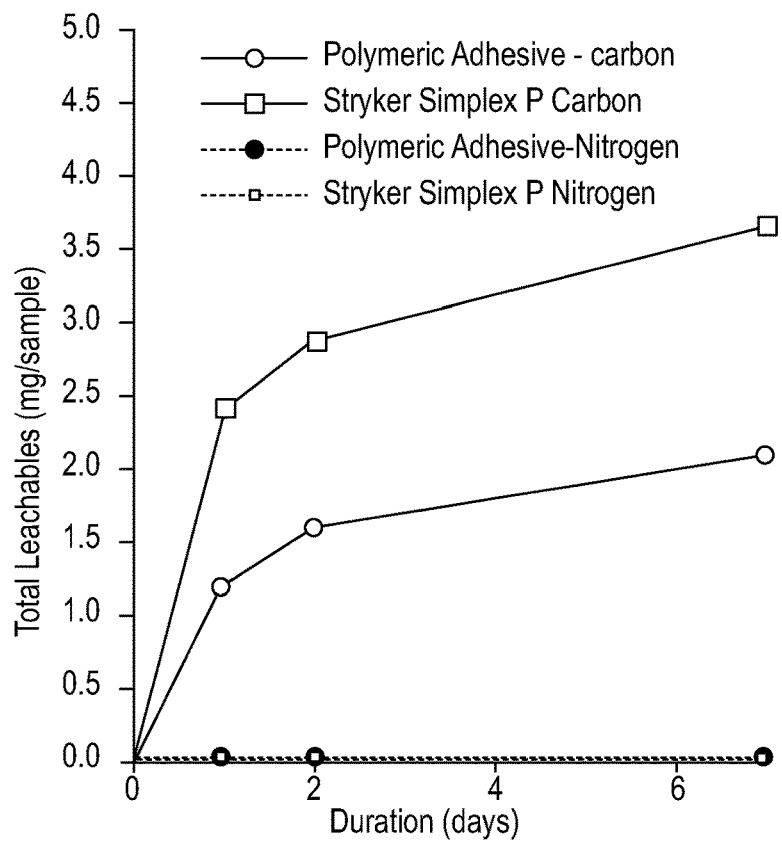
FIG. 19A shows amounts of carbon and nitrogen leaching from adhesive copolymers made according to one embodiment of the invention.
Figure 19B:
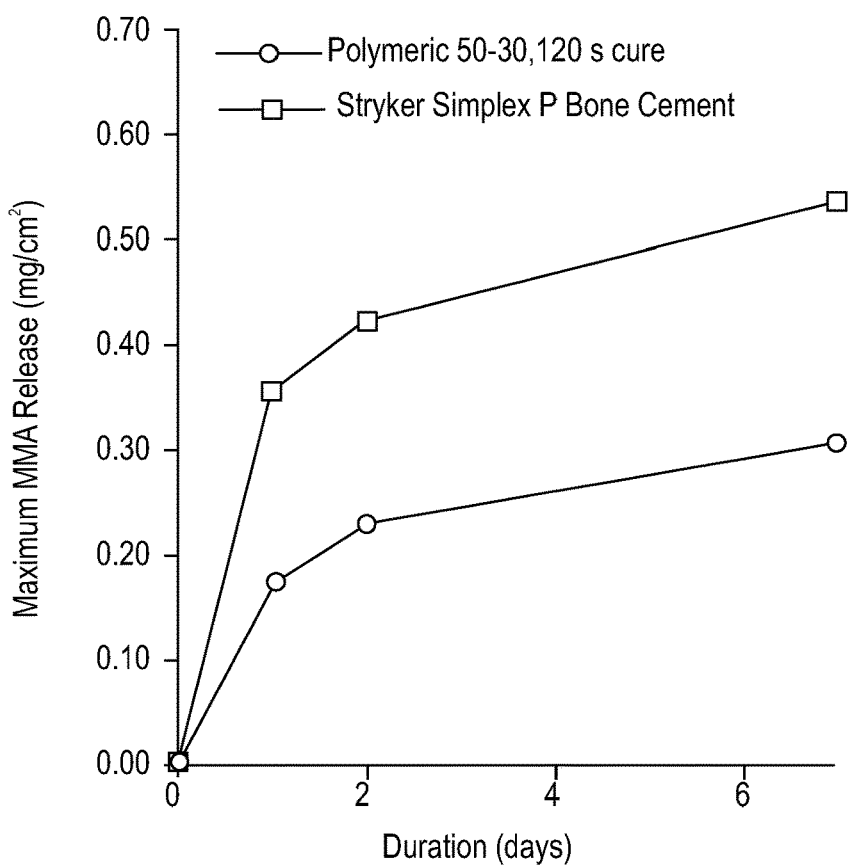
FIG. 19B shows amounts of MMA monomer released from adhesive copolymers made according to one embodiment of the invention.

FIG. 19A shows carbon and nitrogen leachables in ultrapure water over 7 days. Nitrogen leaching approached the detection limit of the measurement system. The polymeric adhesive formulation was PUA-50-30-CQ1.3-DMPT1.0. FIG. 20B shows maximum MMA monomer release over 7 days. This calculation assumes that all carbon was MMA. The higher non-volatile carbon leachables in the polymeric adhesive (FIG. 19B) suggests that this plot shows an overestimation of MMA release for the polymeric adhesive. The polymeric adhesive formulation was PUA-50-30-CQ1.3-DMPT1.0. FIG. 21 shows volatile and non-volatile components of carbon leachables. For the polymeric adhesive samples, the non-volatile carbon was always less than 37% of the total carbon, while for Simplex® P samples the non-volatile carbon was always less than 12% of the total carbon. These results indicate that MMA monomer was the main leachable in both materials. The polymeric adhesive formulation was PUA-50-30-CQ1.3-DMPT1.0.

Figure 20:
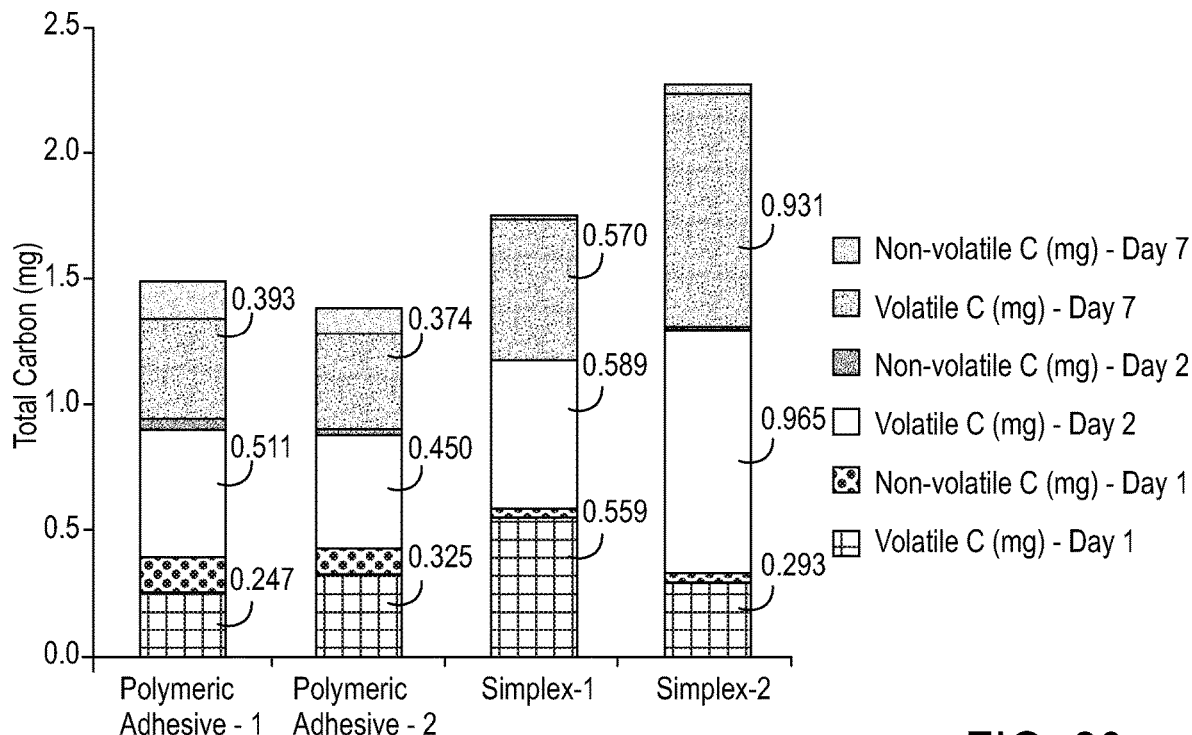
FIG. 20 shows amounts of carbon leachables from adhesive copolymers made according to some embodiments of the invention.
Figure 21:
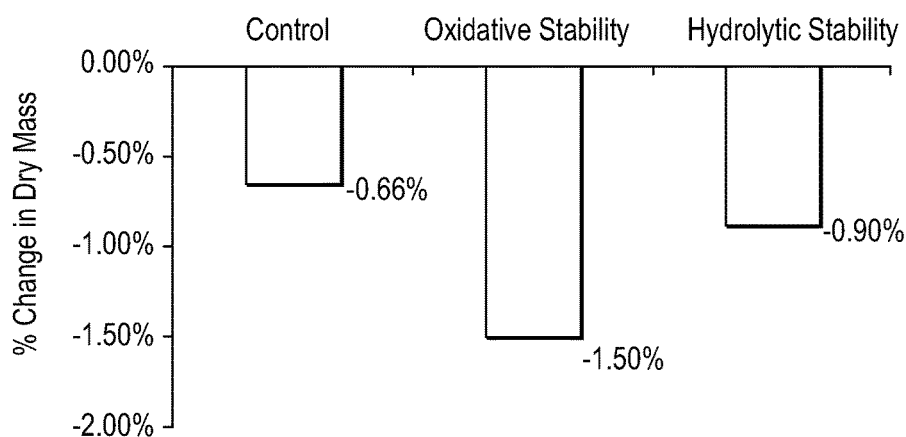
FIG. 21 shows the stability results from accelerated biostability testing of adhesive copolymers made according to some embodiments of the invention.

The described polymeric adhesive leached approximately 40-50% less carbon and MMA monomer than Simplex® P bone cement (FIGS. 20A-B). These results for Simplex® P fall within the range of MMA monomer release reported in the literature [6-7]. In contrast to carbon, the polymeric adhesive leached up to 60% more nitrogen than Simplex® P (FIG. 19A). However, cumulative nitrogen leaching for the polymeric adhesive samples was only 0.040 mg per 1.25 g sample. For the polymeric adhesive samples, the non-volatile carbon was always less than 37% of the total carbon, while for Simplex® P samples the non-volatile carbon was always less than 12% of the total carbon (FIG. 20). These results indicate that MMA monomer was the main leachable in both materials and that the polymeric adhesive had a larger component of leachables that were not MMA, which is likely to be initiator (camphorquinone).

Example 11: Oxidative Stability

Accelerated biostability testing of the polymeric adhesive. Compared to control samples, changes in dry mass were not statistically different for either oxidative stability samples (p=0.058) or hydrolytic stability samples (p=0.307). One set of control samples were used for both oxidative and hydrolytic stability tests.

Accelerated biostability testing was conducted following ISO 10993-13. As a screening test for evaluating oxidative stability, we chose harsher, more accelerated conditions than those recommended in the ISO standard. The ISO-recommended accelerated oxidative stability test involves incubating the samples in 3% hydrogen peroxide at an elevated temperature for 60 days. To further accelerate the test, we incubated polymeric adhesive (PUA-50-30-CQ1.0-EDMAB1.0 [EDMAB=Ethyl 4-(dimethylamino)benzoate]) samples (n=3) in 30% hydrogen peroxide at 52° C. for 14 days (solutions were changed twice per week). Changes in dry mass were compared with changes for control samples (n=3) that were maintained in phosphate buffered saline (PBS, pH 7.4) at 52° C. for 14 days. All samples were equilibrated in PBS before drying for mass measurements.

As can be seen in FIG. 21, samples exposed to these oxidative conditions showed a slight decrease in mass. Compared with control samples, the change in dry mass was approaching statistical significance (p=0.058). These slight changes in dry mass under highly accelerated oxidation conditions support the oxidative stability of the polymeric adhesive.

Example 12: Hydrolytic Stability

As a screening test for evaluating hydrolytic stability, we again chose harsher, more accelerated conditions than those recommended in the ISO 10993-13 standard. The ISO-recommended accelerated hydrolytic stability test involves incubating the samples in PBS at an elevated temperature for 60 days. To further accelerate the test, we incubated polymeric adhesive (PUA-50-30-CQ1.0-EDMAB1.0) samples (n=3) in a basic saline solution at pH 10.6 ($OH^-$ ions induce hydrolysis, so every increase in pH of 1.0 should increase the hydrolysis rate by 10) at 52° C. for 14 days. Theoretically, these incubation conditions are the equivalent of over 170 years at body temperature and pH. Changes in dry mass were compared with changes for control samples (n=3) that were maintained in phosphate buffered saline (PBS, pH 7.4) at 52° C. for 14 days. All samples were equilibrated in PBS before drying for mass measurements.

As can be seen in FIG. 21, samples exposed to these hydrolytic conditions showed a slight decrease in mass. The change in dry mass was not statistically different than the change for control samples (p=0.307). This result under accelerated hydrolytic conditions supports the hydrolytic stability of the polymeric adhesive.

Example 13: Biocompatibility Testing

The ISO cytotoxicity test (ISO 10993-5) was conducted on the following polymeric adhesive formulation: PUA-50-30-CQ1.0-EDMAB1.0. A plate of polymeric adhesive was cured under blue light for 2 min. The cytotoxicity test (24 h extraction at 37° C. in serum-supplemented MEM solution) showed a score of 0 after 48 h, indicating no cytotoxicity (0=non-cytotoxic, 4=highly cytotoxic) [8].

Example 14: Mechanical Properties

FIG. 22 shows a summary of the mechanical properties of the polymeric adhesive (PUA-50-35). Values obtained from [2-7].

The polymeric adhesive technology was invented to attach IPN or semi-IPN containing materials or devices to bone. The mechanical properties of the polymeric adhesive have been engineered to meet the biomechanical requirements for a joint replacement device (FIG. 22). The compressive and tensile stiffness have been tuned to form a bridge between cancellous bone and the anchoring surface of IPN or semi-IPN containing materials or devices. The failure strain has also been engineered to be high enough to allow for the finite deformations of the compliant IPN or semi-IPN containing materials or devices without cracking. The adhesion strength to IPN or semi-IPN containing materials or devices anchoring surfaces, measured using peel tests, approaches the tear strength of the IPN or semi-IPN containing materials or device itself, signifying a secure bond between the device and the cement that limits relative micromotion. In addition, the interfacial bond strength to bone, measured in lap-shear tests, is comparable to the bond strength achieved by PMMA bone cement, which are both higher than the strength of bone itself. Furthermore, the polymeric adhesive is a crosslinked material that has excellent creep properties. In all these aspects, the mechanical properties of the polymeric adhesive are comparable to or exceed those of conventional PMMA bone cement, rendering the polymeric adhesive a viable method for IPN or semi-IPN containing materials or devices attachment.

Mechanical Testing Methods

Example 15: Tensile Testing

Figure 23A:
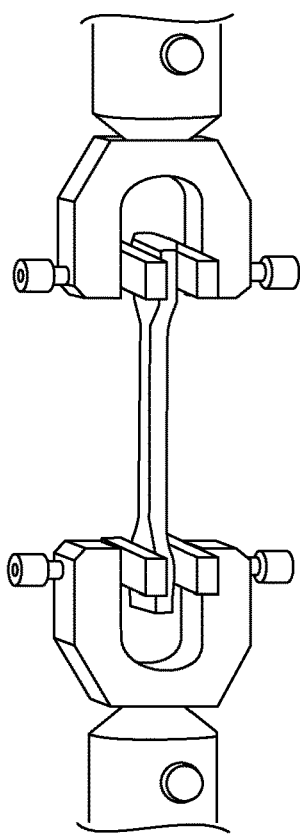
FIG. 23A shows a testing device.
Figure 23B:
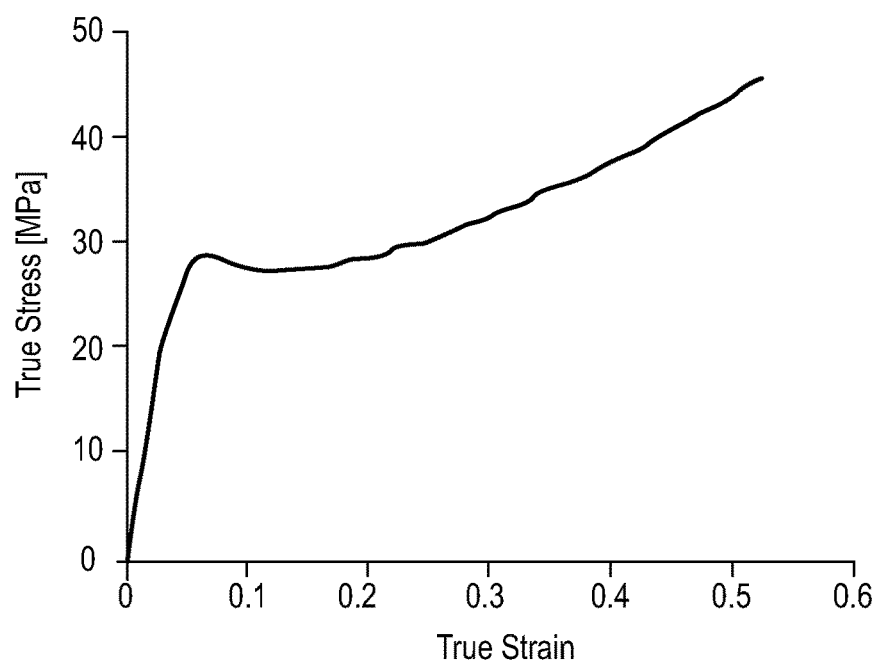
FIG. 23B shows the results of true stress-true strain tensile testing of an adhesive copolymer using a testing device shown schematically in FIG. 23A.

FIG. 23A shows a schematic of the tensile test setup. FIG. 23B shows typical true stress—true strain tensile plot for a polymeric adhesive formulation (PUA-100-35-CQ1.15-BP0.98-DMPT1.15). Elastic modulus at 2 MPa is found by taking the tangent over the stress range of 2±0.75 MPa.

Tensile testing for the polymeric adhesive was performed. Samples were prepared by curing plates of the polymeric adhesive between two glass plates, using spacers for even thickness. Using a cutting die, the polymeric adhesive plates were cut into dumbbell shaped samples for testing. After a period of incubation at 37° C. in PBS, samples were tested using the tensile grips of the mechanical tester. Samples were pulled in tension at a rate of 4.064 mm/s until failure in a 37° C. water bath. Data analysis yielded stress-strain curves, tensile moduli, tensile strength and ultimate tensile strain for the tested samples. FIGS. 23A-B shows the tensile test setup and a typical stress-strain curve for the polymeric adhesive PUA-100-35.

Example 16: Compressive Testing

Figure 24A:
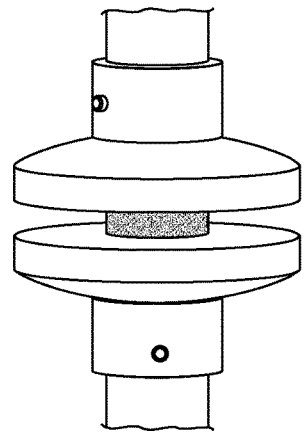
FIG. 24A shows a testing device.
Figure 24B:
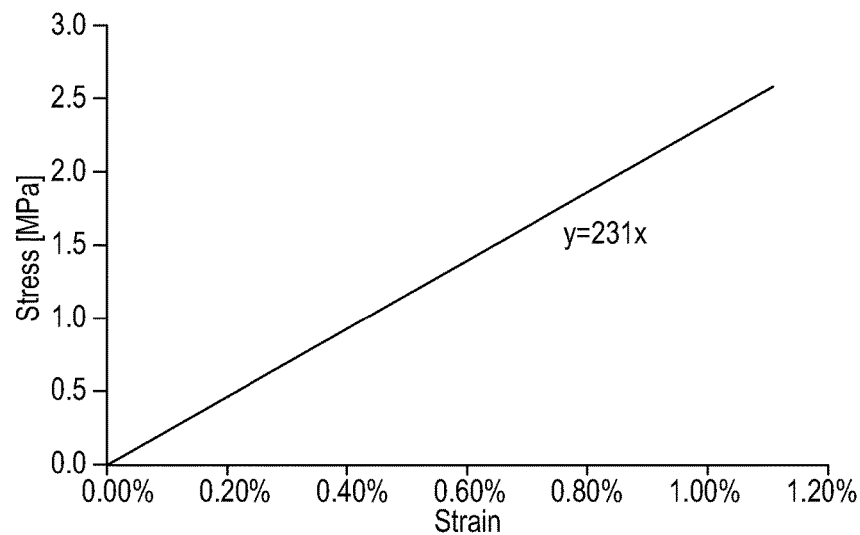
FIG. 24B shows the results of compressive testing of an adhesive copolymer using a testing device shown schematically in FIG. 24A.

FIG. 24A shows a schematic of the compression (unconfined) test setup. FIG. 24B shows a typical stress—strain curve for PUA-50-35-CQ1.11-BP0.95-DMPT1.11. The elastic modulus was found to be 231 MPa.

Example 17: Creep Testing

Figure 25A:
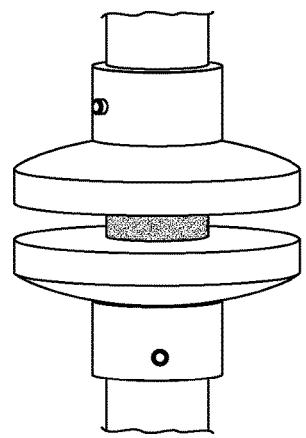
FIG. 25A shows a testing device.
Figure 25B:
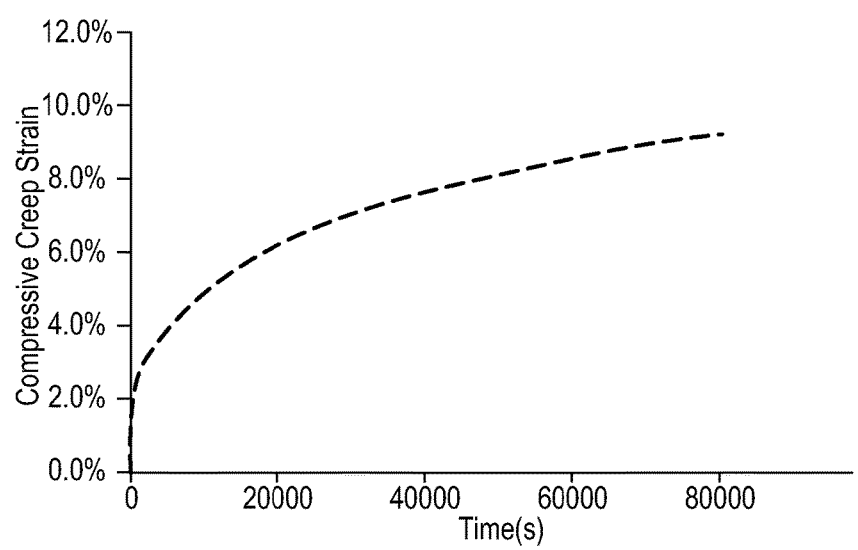
FIG. 25B shows the results of compressive creep testing of an adhesive copolymer using a testing device shown schematically in FIG. 25B.

FIG. 25A: Schematic of the compressive creep (unconfined) test setup. FIG. 25B: A typical compressive creep curve for the polymeric adhesive (PUA-50-35-C1.11-BP0.95-DMPT1.11) sample over a 22 h period.

Figure 26A:
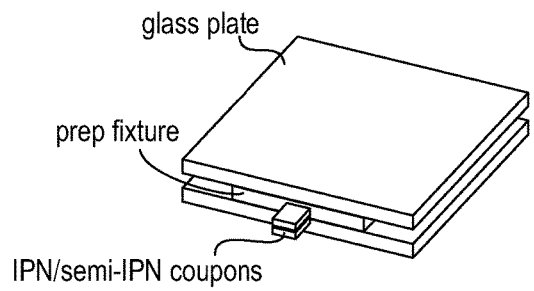
FIGS. 26A-26B show a schematic of a fixture setup for performing a peel test.

Compressive creep testing for one embodiment of the polymeric adhesive. Samples were prepared by curing the polymeric adhesive in 5-mL culture tubes, and then using a lathe to machine the samples into cylinders of 12.5±0.25 mm in thickness and 9.5±0.25 mm in diameter. After a period of incubation at 37° C. in PBS, samples were tested using the compression platens of the mechanical tester. Samples were loaded at a rate of 10 N/s to a maximum holding stress of 2.7 MPa. This stress was held for 22 h to monitor the creep properties of the material. After the creep test was completed, the stress was relieved to a 5 N load at a rate of 10 N/s. The 5-N load was held for 30 min before the sample was measured for compression set (residual strain at 30 min). Each sample remained unloaded in an incubation chamber for at least 24 h before being measured for permanent creep (residual strain at 24 h). FIG. 26A shows the compressive creep test setup and a typical creep response for PUA-50-35-CQ1.11-BP0.95-DMPT1.11.

Example 18: Peel Testing

Figure 26B:
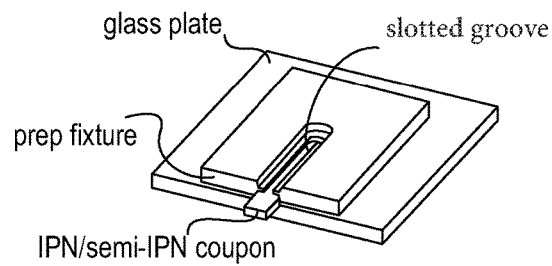

FIGS. 26A-B show the peel test preparation fixture used to make test coupons assembled (FIG. 26A) and disassembled (FIG. 27B) for clarity.

Figure 27A:
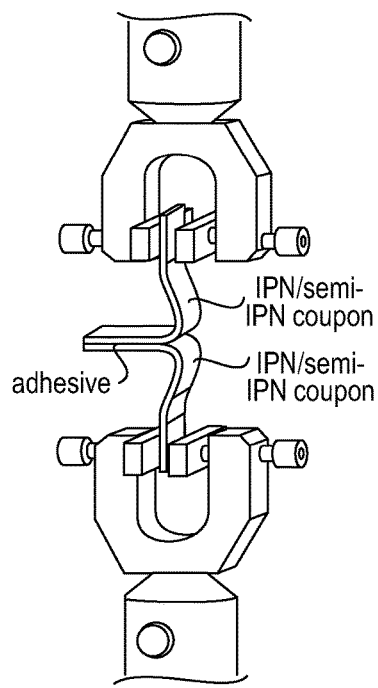
FIG. 27B shows the results of peel testing of an adhesive copolymer using a testing device shown schematically in FIG. 27A.
Figure 27B:
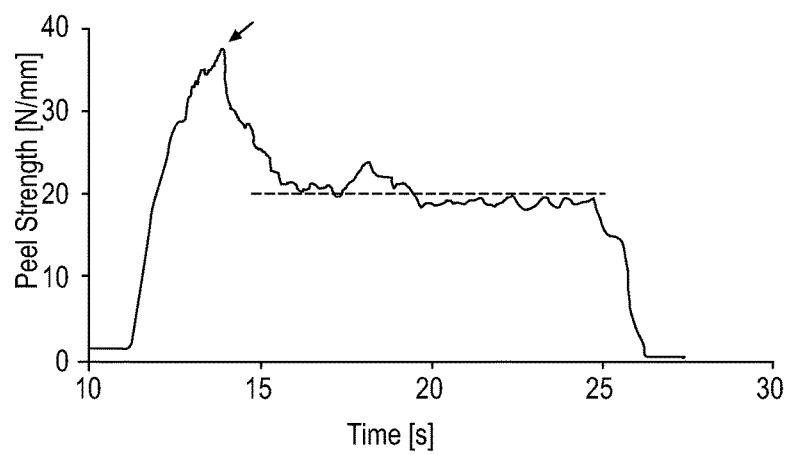

FIGS. 27A-B show schematics of the peel test setup. FIG. 27A: A typical peel test of the polymeric adhesive (PUA-100-35.CQ1.15-BP0.98-DMPT1.15) adhered between two micro-roughened Elasthane™ 75D (polyurethane) coupons. The arrow points at the peak (peel initiation) strength, while the dashed line represents the average peel propagation strength.

Peel testing for one embodiment of the polymeric adhesive was performed. Using the T-Test peel method, we evaluated the peel strength (force required to peel per unit width) required to initiate a peel (peel initiation strength) and to propagate the peel (peel propagation strength). Samples were prepared using a custom peel sample preparation fixture (FIGS. 26A-B). IPN or semi-IPN containing coupons were securely placed on each side of a slotted groove creating a confined cavity between the coupons, with only one opening for polymeric adhesive injection. The IPN or semi-IPN containing coupons were compressed between two glass plates using clamping clips. Then, polymeric adhesive was injected into the opening between the coupons (FIG. 26B). Once the cavity was filled with the polymeric adhesive, the sample was cured and then removed from the fixture. Inventors developed this preparation system in order to ensure every peel sample had a consistent polymeric adhesive width, length and thickness (3.175 mm, 30 mm and 2 mm, respectively) that conform (proportionally) to the ASTM standard. This confined area of the polymeric adhesive reduces the tearing of IPN or semi-IPN containing coupons by increasing the IPN or semi-IPN containing material-to-polymeric adhesive ratio as well as minimizes excess polymeric adhesive flash from the intended test area.

After a period of incubation at 37° C. in PBS, samples were setup and tested using the tensile grips of the mechanical tester (FIGS. 27A-B). The unadhered ends of the sample were placed into each tensile grip, creating a 90 degree angle between the axis of the grips and the adhered end of the sample. Samples were pulled in tension at a rate of 4.23 mm/s until peeling was complete. Data analysis yielded the peak and propagation peel strengths for each sample.

Example 19: Bone Lap-Shear Testing

Figure 28:
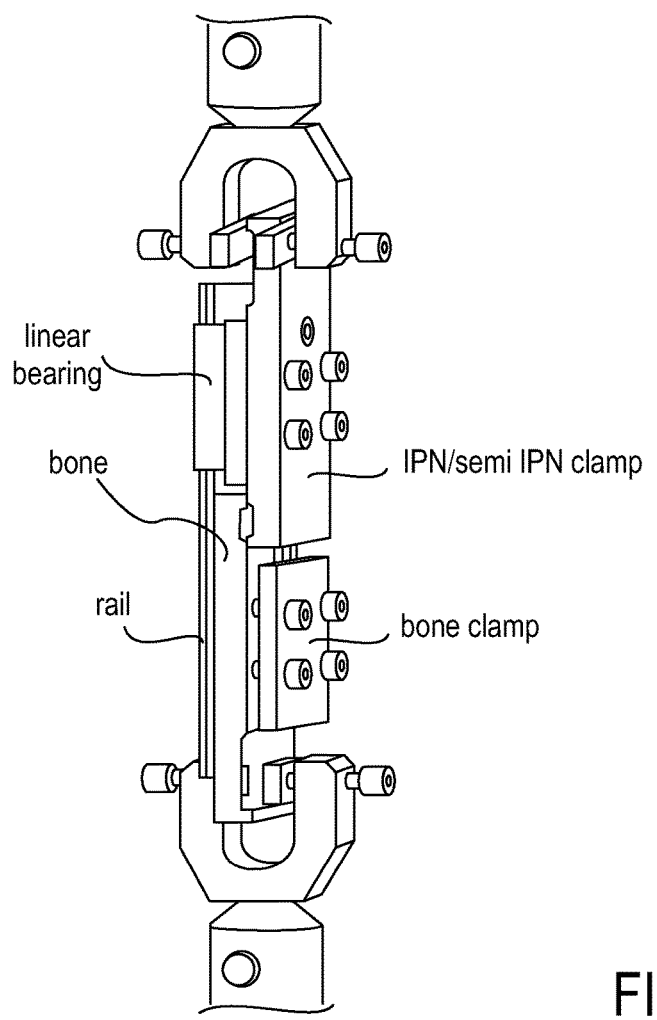
FIG. 28 shows a schematic of a lap shear test device.

FIG. 28 shows a schematic of the bone lap-shear test setup.

Bone lap-shear testing was performed in accordance with ASTM D3163. Samples were prepared by curing polymeric adhesive between a coupon of cancellous bone (taken from the bovine distal femur) and a coupon of polyurethane, both of the same width. Special attention was given in creating loading conditions that would only subject the coupons to shear. Therefore, a linear bearing system was employed that ensured only axial movement of the bone relative to the IPN or semi-IPN containing coupon. In addition, due to initial bone failures (tensile failure) an end support was added to the feature so that bone would be compressed rather than tensioned. The entire system was mounted on the universal testing system using the tensile grips.

The samples were cured and incubated at 37° C. before testing. Using the tensile grips of the mechanical tester, the unadhered ends of the sample were placed in the upper and lower grips. The samples were then pulled in tension at a shear rate of 0.15±0.1 MPa/s until failure. Data analysis yielded the maximum shear stress for each sample.

Example 20: Viscosity Testing

Figure 29:
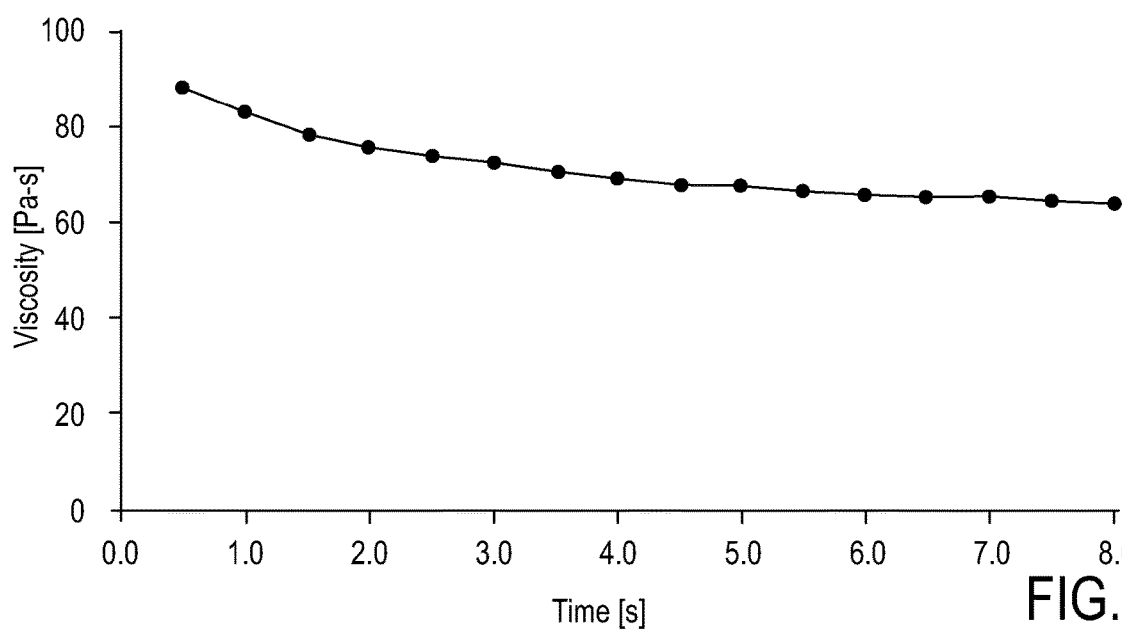
FIG. 29 shows a viscosity profile over time of an adhesive copolymer made according to one embodiment of the invention.

FIG. 29 shows viscosity-time profile of polymeric adhesive (PUA-50-30-CQ1.0-DMPT1.0 (light cure only)) at 23° C. Typical thixotropic behavior of polymeric adhesive is observed in this chart. As the cement is subjected to a constant shear rate, the viscosity profile decreases over time.

Viscosity testing for the polymeric adhesive was performed using a Brookfield HBTCP Dial Viscometer. Each polymeric adhesive formulation was loaded into a 3-mL syringe (with a 0.5 mL resolution) by injecting the polymeric adhesive from a double-barrel syringe directly into the back of the sample syringe. No thermal initiator was added to this batch of polymeric adhesive to prevent curing while testing the polymeric adhesive. Each sample syringe was then capped to prevent exposure to air and wrapped in aluminum foil to prevent exposure to ambient lighting. Each sample syringe was placed in a temperature-regulated environment that matched the desired testing temperature for at least 12 h, allowing time for temperature equilibrium and any material restructuring required during the equilibrium process.

Figure 30:
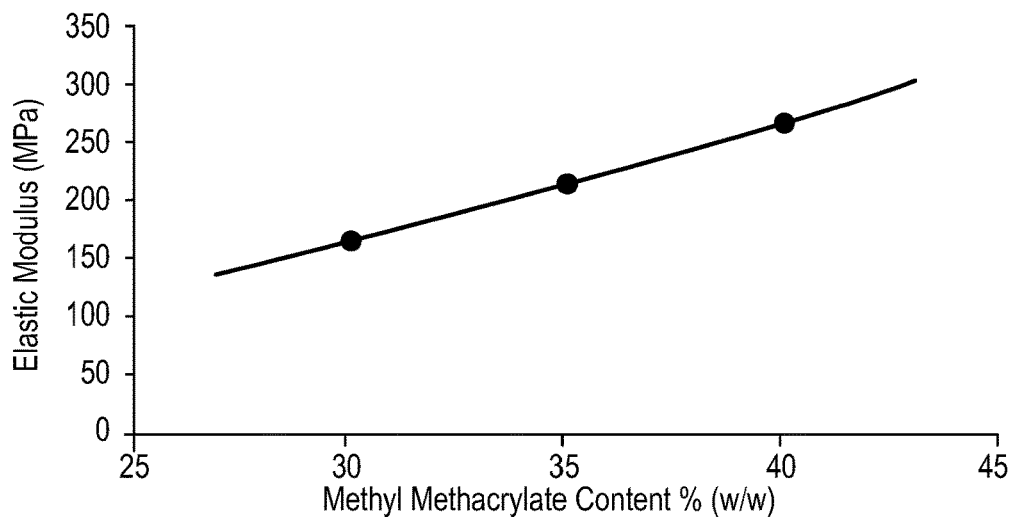
FIG. 30 shows the elastic modulus of adhesive copolymers made with different amounts of MMA monomers according to some embodiments of the invention.

To perform testing, 0.5 mL of the polymeric adhesive was dispensed from the syringe to the center of the viscometer sample cup. The sample was then left for 45-60 minutes in the sample cup to allow it to further equilibrate to the desired testing temperature. All polymeric adhesive formulations were subjected to testing at 18° C., 23° C., and 37° C. The speed of the viscometer was dependent on the viscosity of the sample, ranging from 0.5 RPM to 20 RPM. Higher viscosity samples required higher RPM. Due to the thixotropic properties of the polymeric adhesive (decreasing viscosity at a constant shear rate over time), measurements were made every 30 s for 8 min as shown in FIG. 30. The average of the sixteen measurements was reported as the viscosity of the polymeric adhesive formulation at the specific temperature. Viscosity for the polymeric adhesive is reported in Pascals per second (Pa-s).

Mechanical Properties as a Function of Material Composition

FIG. 30 shows elastic modulus of the polymeric adhesive versus the MMA-content in the final material. These data points were obtained from the following polymeric adhesive formulations (in order from left to right):

PUA-50-30-CQ1.0-BP0.85-DMPT1.0,
PUA-50-35-CQ1.11-BP0.95-DMPT1.11,
PUA-50-40-CQ1.22-BP1.04-DMPT1.22

The described polymeric adhesive is designed to bridge the stiffness mismatch between the compliant IPN or semi-IPN containing device and the cancellous bone to which it is anchored. Using the information from these measurements, the right formulation can be selected to better match the product specs.

An MMA-content in the range of 35% for some orthopedic implants is suggested in terms of compressive properties.

Example 21: Hardness (Shore D) vs MMA %

Figure 31:
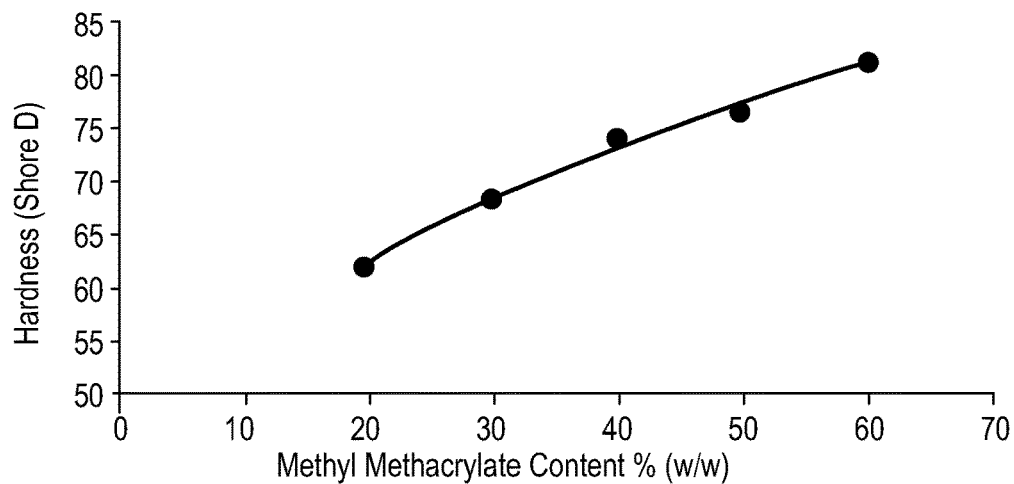
FIG. 31 shows the hardness of adhesive copolymers made with different amounts of MMA monomers according to some embodiments of the invention.

FIG. 31 shows polymeric adhesive hardness (Shore D) versus the MMA-content.

Figure 32:
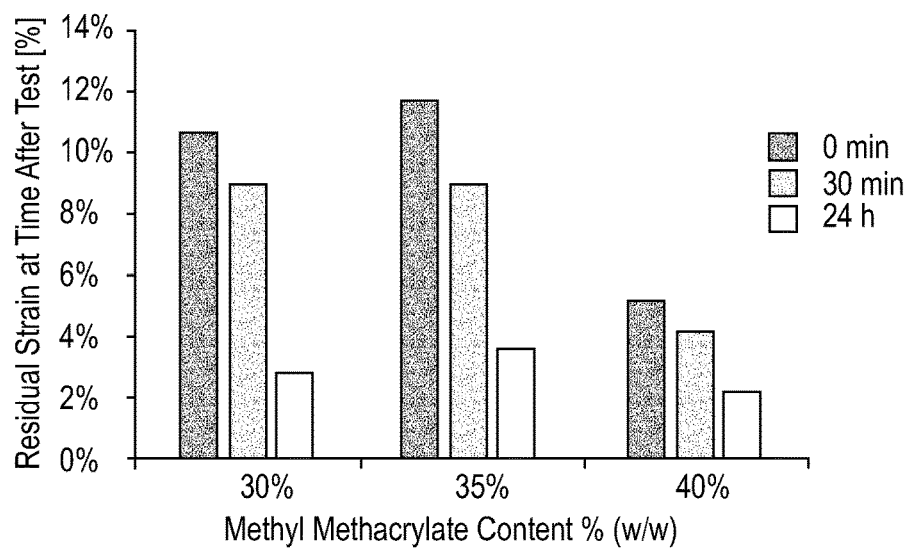
FIG. 32 shows creep recovery of adhesive copolymers made with different amounts of MMA monomer according to some embodiments of the invention.

Similar to the compressive stiffness, polymeric adhesive hardness increases with increasing MMA-content (FIG. 32). The polymeric adhesive was cured inside OD=10 mm polypropylene cylinders, and then were machined transversely flat on a vertical mill. A digital durometer was then used to measure hardness.

As can be seen in FIG. 31, the higher the MMA-content, the more the material resembles PMMA. Accordingly, the lower the MMA-content, the more the material resembles pure UDMA.

Example 22

FIG. 32 shows creep recovery after 22 h of loading at 2.7 MPa. The data show the remaining strain at 0 min, 30 min, and 24 h after the 2.7 MPa load has been removed and the sample was allowed to recover its thickness. Data for three polymeric adhesive are shown (from left to right: PUA-50-30-CQ1.0-BP0.85-DMPT1.0, PUA-50-35-CQ1.11-BP0.95-DMPT1.11, and PUA-50-40-CQ1.22-BP1.04-DMPT1.22).

It is important for a bone cement to maintain good creep properties for the working tolerances of a compliant cartilage replacement to be maintained. The described polymeric adhesive is a crosslinked material that recovers very well after the load is removed. One important note here has to be made on the time to recover. The described polymeric adhesive presents a rather large viscoelastic time constant, which means that it takes a long time to reach the equilibrium strain when a compressive load is applied and to relax upon load removal. FIG. 32 shows the creep recovery behavior for various polymeric adhesive formulations.

An MMA content of 30%-35% is suggested for some medical implants.

Example 23: Peel Strength vs. MMA %

Figure 33A:
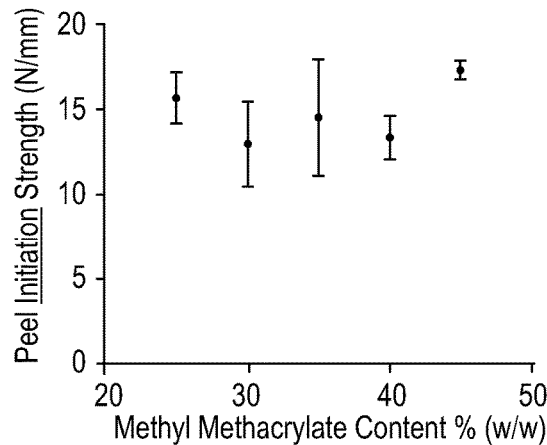
FIG. 33A shows peel initiation strength of adhesive copolymers made with different amounts of MMA monomer on a polyether urethane according to some embodiments of the invention.
Figure 33B:
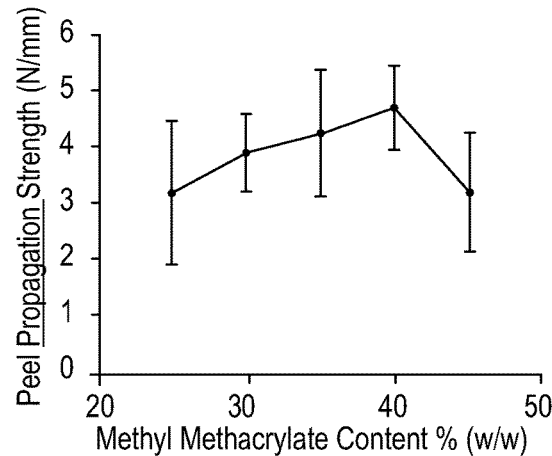
FIG. 33B shows peel propagation strength of adhesive copolymers made with different amount of MMA monomer on a polyether urethane according to some embodiments of the invention.

FIGS. 33A-B show peel initiation (FIG. 33A) and peel propagation (FIG. 33B) strength for smooth Elasthane™ 65D plates and five polymeric adhesive formulations (In order from left to right: PUA-50-25-CQ0.88-BP0.73-DMPT0.88, PUA-50-30-CQ1.0-BP0.85-DMPT1.0, PUA-50-35-CQ1.11-BP0.95-DMPT1.11, PUA-50-40-CQ1.22-BP1.04-DMPT1.11, and PUA-50-45-CQ1.41-BP1.2-DMPT1.41).

Peel properties are probably the most efficient method to qualify an adhesive. The described polymeric adhesive demonstrates high peel strength, both at the initiation level and at the propagation level. FIGS. 33A-B demonstrate the peel properties of the described polymeric adhesive on smooth Elasthane™ 65D (used here as a proxy for Elasthane™ 75D that comprises the anchoring surface of IPN or semi-IPN containing materials or devices). MMA % had no significant effect on peel strength in the 30-40% MMA-content range.

Figure 34A:
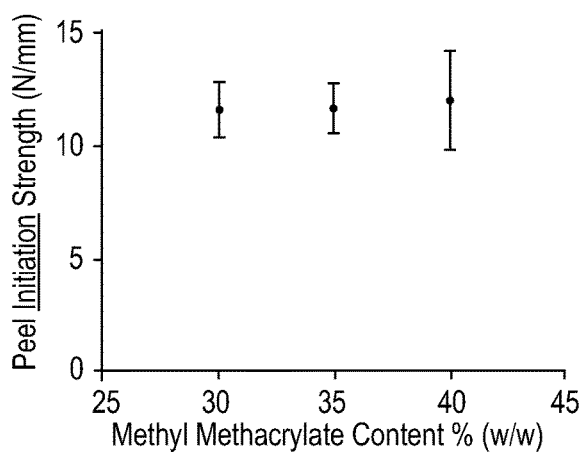
FIG. 34A shows peel initiation strength of adhesive copolymers made with different amounts of MMA monomer on an IPN or semi-IPN implant device according to some embodiments of the invention.
Figure 34B:
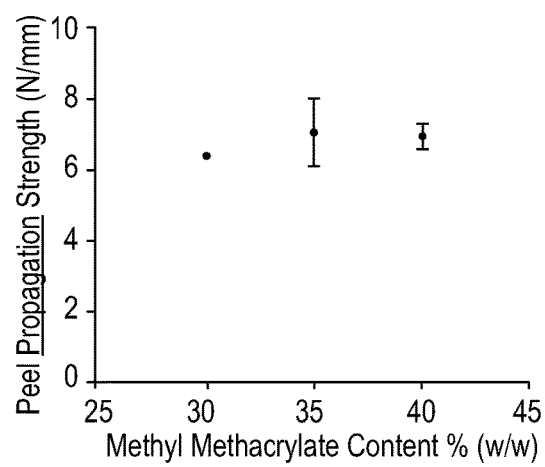
FIG. 34B shows peel propagation strength of adhesive copolymers made with different amount of MMA monomer on an IPN or semi-IPN implant device according to some embodiments of the invention.

FIG. 34A-B show peel initiation (FIG. 35A) and peel propagation (FIG. 34B) strength for an IPN or semi-IPN containing acetabular device for three polymeric adhesive formulations (In order from left to right: PUA-50-30-CQ1.0-BP0.85-DMPT1.0, PUA-50-35-CQ1.11-BP0.95-DMPT1.11, and PUA-50-40-CQ1.22-BP1.04-DMPT1.11).

Peel tests were also conducted on the anchoring surface of IPN/semi-IPN devices which showed a high peel strength, as shown in FIGS. 34A-B. Nonetheless, we have the goal of reaching a peel strength equal to the tear strength of the IPN or semi-IPN containing material itself (approx. 30 N/mm), so additional ways to increase peel strength are of interest.

No significant difference was observed within the 30%-40% MMA-content span. MMA-content in the range of 30%-40% is suggested for some medical implants.

Example 24: Viscosity vs. MMA %

Figure 35:
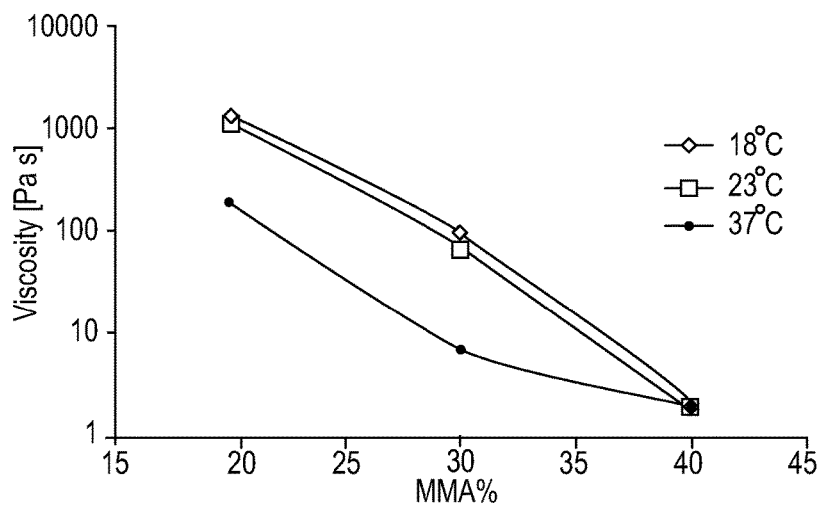
FIG. 35 shows another set of results for viscosities of adhesive copolymers made with different amounts of MMA monomers according to some embodiments of the invention.

FIG. 35 shows another set of viscosity-MMA % profiles for the polymeric adhesive (PUA-50-30-CQ1.0-DMPT1.0) at 18° C., 23° C., and 37° C. performed after refinements were made to the materials and/or test processes. See also FIG. 14 and FIG. 15.

From the wide range of viscosities available with different polymeric adhesive formulations, the optimal viscosity range lies between 20% and 40% MMA-content for some embodiments. In some embodiments, outside of this MMA-content range viscosities are not functionally viable for some arthroplasty applications (either too viscous to inject or too runny to use). In evaluating viscosity, relationships between temperature and viscosity and MMA-content and viscosity were determined.

For reference: OR temperature is approximately 18° C., room temperature is 23° C., open incision temperature is 34° C., and body (core) temperature is 37° C.

Generally, there is an inverse relationship between temperature and viscosity, where an increasing temperature results in lower viscosities. Similarly, an inverse relationship between MMA-content and viscosity has been established, in which more MMA in the polymeric adhesive formulation yields lower viscosities. Results for polymeric adhesive not containing the thermal initiator (thermal initiator would cause instant polymerization and viscosity values could not be measured effectively) are shown in FIG. 36.

To optimize surgical handling for some medical implants (e.g. orthopedic implants), a viscosity in the range of 10-100 Pa-s is desirable and range of MMA % within 30-35% is suggested.

Example 25

Figure 36:
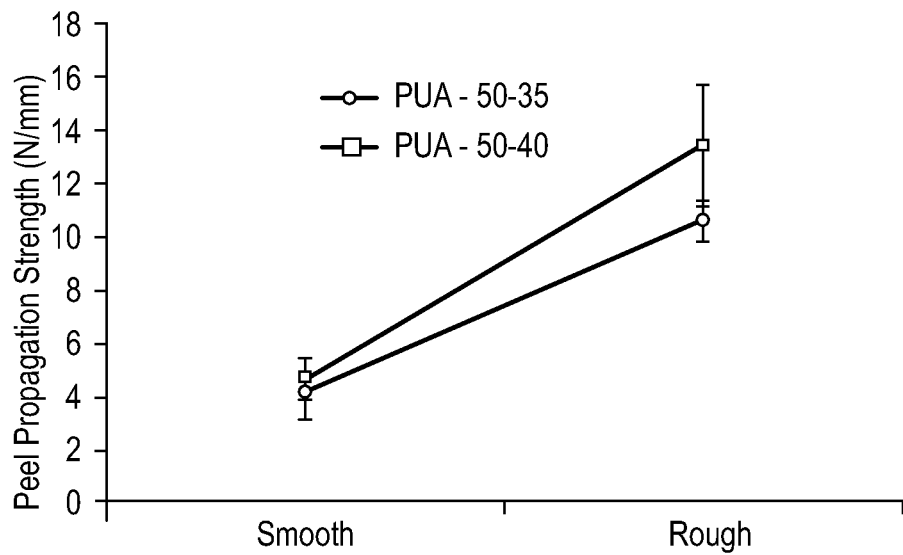
FIG. 36 shows a comparison of peel propagation strength for adhesive copolymers on smooth and roughened polyether urethanes.

Peel Strength vs. Surface Roughness FIG. 36 shows a comparison of peel propagation strength for a smooth and a roughened Elasthane™ 65D surface, using two different polymeric adhesive formulations (PUA-50-35-CQ1.11-BP0.95-DMPT1.11 and PUA-50-40-CQ1.22-BP1.04-DMPT1.22).

Adding roughness to the adhesion surfaces greatly increases the peel strength as it provides more surface area for molecular interaction as long as the wettability of the cement is maintained. Smooth Elasthane™ 65D plates were sanded to a roughness of approximately $R_a$=200 µm and tested in a peel test. As expected, the adhesion force was significantly increased (almost doubled). Therefore, adding roughness to the anchoring surface of the IPN or semi-IPN containing devices is recommended. FIG. 36 demonstrates the differences between rough and smooth coupon geometries.

For reference, initial tests with roughened Elasthane™ 75D showed a peak peel strength in the 30-40 N/mm range while the peel propagation strength reached approximately 20 N/mm. These values are approaching the tear strength of IPN or semi-IPN containing devices or materials itself.

Add a bi-level roughness profile to the anchoring surface of IPN or semi-IPN containing materials or devices may improve the adhesion properties: a macro-roughness of approximately $R_a$=100-200 µm with an additional micro-roughness of 10-20 µm for some medical implants. It is hypothesized that this bi-level roughness will ensure that the surface available for adhesion is maximized.

Figure 37:
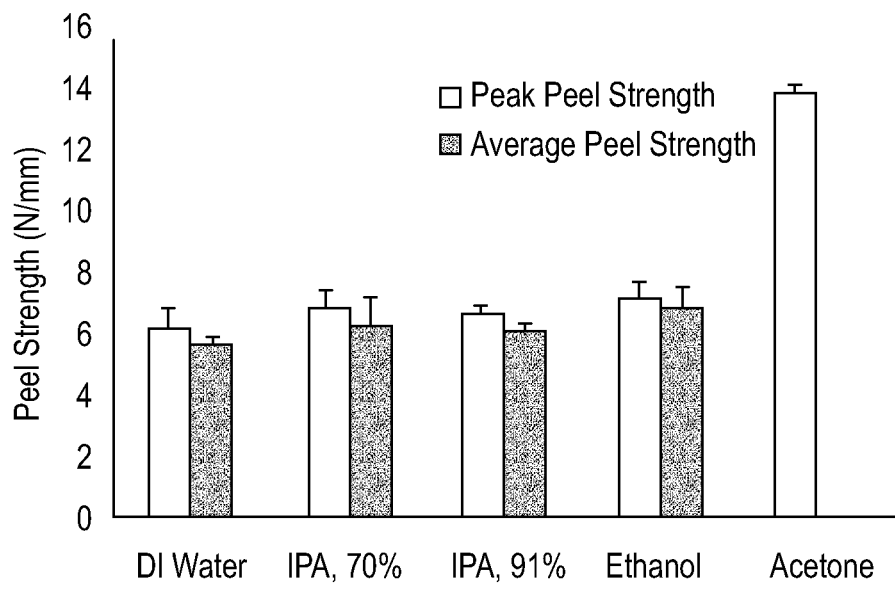
FIG. 37 shows peel strength for adhesive copolymers adhered to polyether urethanes after various surface treatments.
Figure 38:
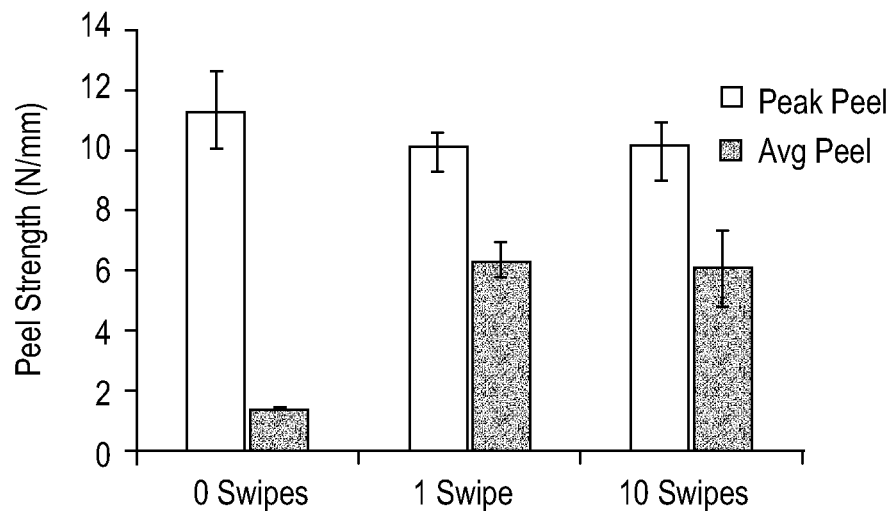
FIG. 38 shows a comparison of peel strength for adhesive copolymers adhered to polyether urethanes with and without surface acetone priming.

Example 26: An IPN or Semi-IPN Containing Device's Surface Preparation Vs. Peel Strength FIG. 37 shows a polymeric adhesive PUA-50-30-CQ1.0-EDMAB1.0 (light cure only) to PU (Elasthane™ 80A and 65D) peel strength for various PU surface preparation solutions. PU samples were swiped with the indicated solution. The acetone primed samples did not really peel, but rather tore, so no average value is recorded. Note that average peel strength is reported in this test (not propagation peel strength). FIG. 38 shows testing of polymeric adhesive PUA-50-30-CQ1.0-EDMAB1.0 (light cure only) on IPN or semi-IPN containing coupons without any acetone treatment (0 swipes) produced a relatively low propagation peel strength. However, swiping with acetone resulted in an almost five-fold increase in propagation peel strength. No significant change was seen when more swipes were performed.

Figure 39:
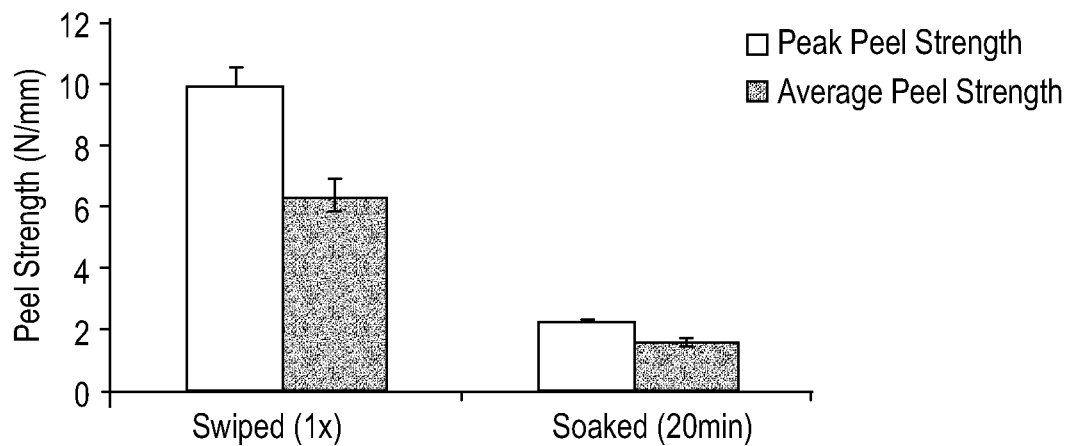
FIG. 39 shows peel strength for adhesive copolymers adhered to an IPN or semi-IPN with different acetone application techniques.

FIG. 39 shows the peel strength of the described polymeric adhesive PUA-50-30-CQ. 10-EDMAB1.0 (light cure only) to the IPN or semi-IPN containing material was dependent on the way acetone was applied to the coupons. Subjecting the coupons to a single swipe of acetone provided three to five times higher peel strength than simply soaking the coupons in acetone for 20 min.

The adhesion of described polymeric adhesive to polyether polyurethanes (PU), such as an IPN or semi-IPN containing anchoring surface, can be increased by swiping the PU surface with acetone. It was found by peel tests that PU strips swiped with acetone showed >100% higher peel strength than those swiped with water, ethanol, 70% IPA, or 91% IPA, as shown in FIG. 37.

Another factor that may affect the adhesion to PU is the actual act of swiping the surface itself. As shown in FIG. 39, the propagation peel strength of the PU surface swiped with acetone is almost five times higher than for a sample simply soaked in acetone (no swiping).

Given that acetone is a better swelling solvent for PU than water, ethanol, or IPA, it is hypothesized that the higher peel strength may be due to the morphological change on PU surfaces that is induced by partial swelling with acetone. The surface of PU becomes momentarily slightly swollen, and the mobility of polymer chains is increased. Further, these more mobile chains are somehow aligned by the swiping process and, thus, the acetone swiping process leads to an increase of the bonding between PU and the described polymeric adhesive. This phenomenon appears to fully occur with one swipe as swiping ten times did not improve the peel strength over swiping one time (FIG. 39).

Although the action mechanism is not well understood, mechanical swiping of the anchoring surface of IPN or semi-IPN containing materials or devices with acetone prior to implantation is suggested for some embodiments.

Example 27

Figure 40:
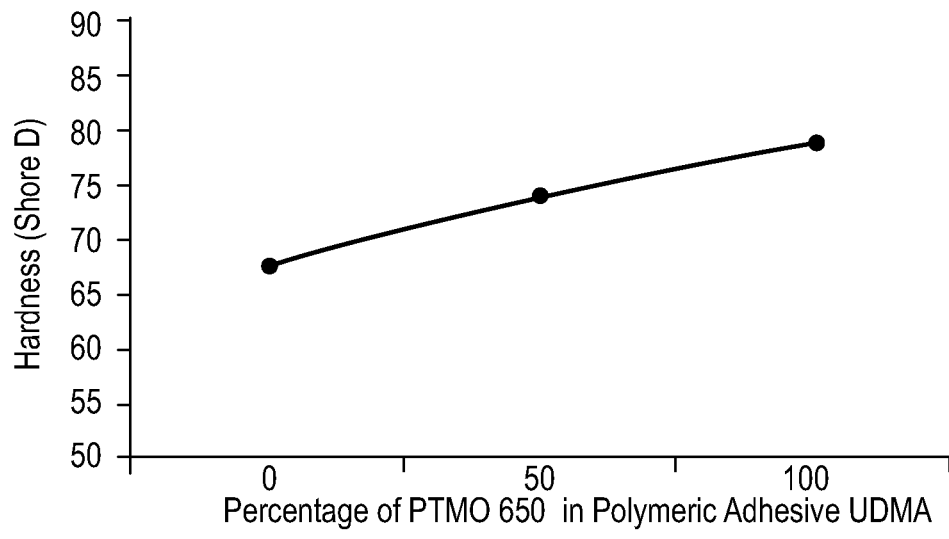
FIG. 40 shows hardness of adhesive copolymers made with UDMA with different amounts and weights of PTMO starting material.

Hardness vs. PTMO Molecular Weight FIG. 40 shows polymeric adhesive Hardness versus polyol (PTMO) molecular weight contribution. The x-axis shows the percentage of PTMO 650 in the formulation of polymeric adhesive UDMA, the rest being PTMO 1000. From left to right, the polymeric adhesive constituents are as follows: PUA-00-35-CQ1.1-BP0.95-DMPT1.1, PUA-50-35-1.11-BP0.95-DMPT1.11, PUA-100-35-CQ1.15-BP0.98-DMPT1.15.

In the described polymeric adhesive, PTMO polyol is the soft segment of the UDMA component. PTMO comes in various molecular weights. Elasthane™ 75D and Elasthane™ 65D use PTMO of molecular weight 650 Da while Elasthane™ 55D uses PTMO of molecular weight 1000 Da. We hypothesized that matching the PTMO molecular weight of Elasthane™ 75D would result in optimal adhesion between the polymeric adhesive and the anchoring surface of the IPN or semi-IPN containing materials or device. The adhesive and stiffness characteristics of the polymeric adhesive were explored for the two PTMO molecular weights. In general, the higher the molecular weight of the PTMO, the softer the material as there is more w/w soft segment material (FIG. 30). If the molecular weight of the PTMO is too high, solidification of the UDMA will occur. The following batches were made and tested:

polymeric adhesive containing 0% PTMO 650 and 100% PTMO 1000 polymeric adhesive containing 50% PTMO 650 and 50% PTMO 1000 polymeric adhesive containing 100% PTMO 650 and 0% PTMO 1000.

Example 28: Tensile Modulus and Strength vs. PTMO Molecular Weight

Figure 41:
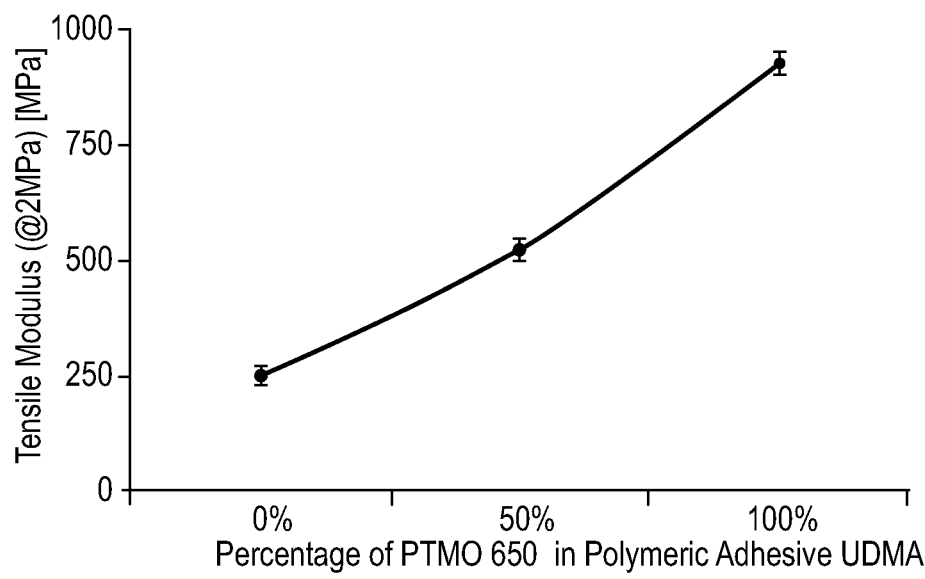
FIG. 41 shows tensile modulus of adhesive copolymers made with UDMA with different amounts of PTMO starting materials.

FIG. 41 shows tensile modulus of polymeric adhesive (at 2 MPa) versus PTMO molecular weight contribution. The x-axis shows the percentage of PTMO 650 in the formulation of polymeric adhesive UDMA, the rest being PTMO 1000. From left to right, the polymeric adhesive formulations are as follows: PUA-00-35-CQ1.1-BP0.95-DMPT1.1, PUA-50-35-CQ1.11-BP0.95-DMPT1.11, PUA-100-35-CQ1.15-BP0.98-DMPT1.15.

FIGS. 42A-B show another set of results for ultimate Engineering Strain (FIG. 42A) and Ultimate Engineering Stress (FIG. 42B) of the polymeric adhesive versus PTMO molecular weight contribution performed after refinements were made to the processes. See also FIG. 12. The x-axis shows the percentage of PTMO 650 in the formulation of the described polymeric adhesive UDMA, the rest being PTMO 1000. From left to right, the polymeric adhesive formulations are as follows: PUA-00-35-CQ1.1-BP0.95-DMPT1.1, PUA-50-35-CQ1.11-BP0.95-DMPT1.11, PUA-100-35-CQ1.15-BP0.98-DMPT1.15.

The molecular weight of the PTMO used in the formulation of the described polymeric adhesive has a profound impact on the tensile properties of the final material. The lower the molecular weight, the stiffer the material is in tension (FIG. 40). The polymeric adhesive has been formulated as a mix of PTMO 650 and PTMO 1000 or simply containing one or the other. As shown in FIG. 41, the tensile modulus may vary by almost four-fold between the all-PTMO 650 formulation and the all-PTMO 1000 formulation. However, the all-PTMO 650 formulation is more brittle, as its ultimate strain (engineering) is less than half that of the all-PTMO 1000 formulation (FIG. 41). In contrast, tensile strength was not significantly affected by PTMO molecular weight (FIG. 41).

A PTMO molecular weight of 650 at 50% or more of the total PTMO is suggested to maintain sufficient stiffness and failure properties for some medical implants.

Example 29: Peel Strength vs. PTMO Molecular Weight

FIGS. 43A-B show polymeric adhesive peak peel initiation (FIG. 43A) and peel propagation (FIG. 43B) strength versus the PTMO molecular weight contribution. The x-axis shows the percentage of PTMO 650 in the formulation of polymeric adhesive UDMA, the rest being PTMO 1000. From left to right in each chart, the polymeric adhesive constituents are as follows: PUA PUA-00-35-CQ1.1-BP0.85-DMPT1.1, PUA-50-35-CQ1.11-BP0.95-DMPT1.11, PUA-100-35-CQ1.15-BP0.98-DMPT1.15.

As mentioned previously, some IPNs or semi-IPNs contain Elasthane™ 75D, which consists of PTMO of molecular weight 650 Da. The adhesive properties of the described polymeric adhesive were explored for the two PTMO molecular weights of 650 and 1000 Da. The following batches were made and tested for adhesion to smooth Elasthane™ 65D (which contains PTMO 650); results are presented in FIGS. 43A-B:

polymeric adhesive containing 0% PTMO 650 and 100% PTMO 1000 (PUA-00-35-CQ1.1-BP0.85-DMPT1.1)
polymeric adhesive containing 50% PTMO 650 and 50% PTMO 1000 (PUA-50-35-CQ1.11-BP0.95-DMPT1.11)
polymeric adhesive containing 100% PTMO 650 and 0% PTMO 1000 (PUA-100-35-CQ1.15-BP0.98-DMPT1.15).

No significant differences in peel strength were observed when varying PTMO 650 and PTMO 1000 content under these test conditions. These results suggests that any concentration of PTMO 650 and 1000 may be useful some medical (e.g. orthopedic) implants.

Example 30: General

FIG. 44 shows a summary of the MMA content parametric studies of various properties of adhesive copolymers made using different amounts of MMA monomer, including results presented above. Dark shaded areas indicate amounts of MMA in adhesive compositions that may be particularly useful for some orthopedic implants. Light shaded areas indicate other tested compositions that may be useful for other applications. Overall, approximately 35% MMA content may be optimal for some medical (orthopedic joint) implants.

Current data suggest that modulus may be the only parameter that is substantially affected by PTMO molecular weight. All things being equal, it may be advantageous to have the PTMO in the described polymeric adhesive match that in the device, namely PTMO 650 in one particular embodiment.

REFERENCES

[1] Charnley J. (1972) *Acrylic Cement in Orthopaedic Surgery*. Edinburgh, London: Churchill Livingstone.
[2] Morgan E F et al. (2001). Dependence of yield strain of human trabecular bone on anatomic site. *J Biomech* 34:569-577.
[3] Ohman C et al. (2007). Mechanical testing of cancellous bone from the femoral head: Experimental errors due to off-axis measurements. *J Biomech* 40:2426-2433.
[4] Lewis G (1997). Properties of acrylic bone cement: State of the art review. *JBMR* 38:155-182.
[6] Puska M A et al. (2005). Exothermal characteristics and release of residual monomers from fiber-reinforced oligomer-modified acrylic bone cement. *J Biomat App* 20:51-64.
[7] Simplex™ P Bone Cement, Stryker Orthopaedics (Mahwah, N.J.). Product Literature LSB Rev. 3, 2006.
[9] Barszczewska-Rybarek (2012). *Journal of Applied Polymer Science*, Vol. 123, 1604-1611.
[10] Bone Cement Time Setting Chart, DePuy Orthopaedics (Warsaw, Ind.), http://www.depuy.com/sites/default/files/products/files/DO_Bone_Cement_Setting_Time_Chart.pdf.
[11] Orr J F, Dunne N J, Quinn J C. (2003). Shrinkage stresses in bone cement. *Biomaterials* 24(17):2933-40.
[12] Kwong F N, Power R A. (2006). A comparison of the shrinkage of commercial bone cements when mixed under vacuum. *J Bone Joint Surg Br.* 88(1):120-2.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:
1. A device comprising: (a) a polymeric implant, (b) a metal or ceramic material, and (c) a urethane dimethacrylate-methyl methacrylate copolymer adhering the polymeric implant to the metal or ceramic material, the urethane dimethacrylate-methyl methacrylate copolymer comprising a plurality of first polymer regions based on urethane dimethacrylate and a plurality of second polymer regions based on methyl methacrylate.

2. The device of claim 1, wherein the plurality of first polymer regions based on urethane dimethacrylate comprises a plurality of hard segments and soft segments.

3. The device of claim 1, wherein the implant is an orthopedic joint implant comprising a polyurethane IPN or a polyurethane semi-IPN.

4. The device of claim 1, wherein the implant is an orthopedic joint implant comprising a polyether urethane IPN or a polyether urethane semi-IPN.

5. The device of claim 1, wherein the first polymer regions based on urethane dimethacrylate comprise about 60%-99% (w/w) of the copolymer and the second polymer regions based on methyl methacrylate comprise about 1%-40% (w/w) of the copolymer.

6. The device of claim 1, wherein the first polymer regions based on urethane dimethacrylate comprise about 60%-80% (w/w) of the copolymer and the second polymer regions based on methyl methacrylate comprise about 20%-40% (w/w) of the copolymer.

7. The device of claim 2, wherein the hard segment of the first polymer region based on urethane dimethacrylate comprises one or more of: 1,5 naphthalene diisocyanate (NDI), 2,6 toluene diisocyanate or 2,4 toluene diisocyanate (TDI), 3,3-bitoluene diisocyanate (TODI), cyclohexyl diisocyanate (CHDI), hexamethyl diisocyanate (HDI), isophorone diisocyanate (IPDI), methylene bis(p-phenyl) isocyanate, methylene diphenylisocyanate (MDI), and methylene bis (p-cyclohexyl isocyanate) (HMDI).

8. The device of claim 2, wherein the soft segment of the first polymer region based on urethane dimethacrylate comprises one or more of: polybutadiene, polyethylene oxide (PEO), hydroxy terminated butadiene, hydroxybutyl terminated polydimethylsiloxane (PDMS), hydroxyl terminated polyisobutylene, poly (1,6 hexyl 1,2 ethyl carbonate), polycaprolactone, polycarbonate, polyethylene adipate, polyhexamethylene carbonate glycol, polypropylene oxide (PPO), polytetramethylene adipate, poly(dimethylsiloxane), and poly(tetramethylene oxide) (PTMO).

9. The device of claim 2, wherein the hard segment of the first polymer region based on the urethane dimethacrylate comprises methylene diphenylisocyanate (MDI) and the soft segment of the first polymer region based on the urethane dimethacrylate comprises poly(tetramethylene oxide) (PTMO).

10. The device of claim 1, wherein the urethane dimethacrylate-methyl methacrylate copolymer defines a compressive modulus between about 30 MPa and about 2000 MPa.

11. The device of claim 1, wherein the urethane dimethacrylate-methyl methacrylate copolymer defines a tensile modulus between about 30 MPa and 2000 MPa.

12. The device of claim 1, wherein the urethane dimethacrylate-methyl methacrylate copolymer defines a tensile failure strain between about 25% and about 200%.

13. The device of claim 1, further comprising a radiopaque material.

14. A method of adhering a polymeric implant to a metal or ceramic material comprising copolymerizing a mixture containing a first non-urethane-containing precursor, a second urethane-containing precursor, and an initiator to form an adhesive copolymer comprising a non-urethane-containing portion based on the first precursor and a urethane-containing portion based on the second precursor, wherein the adhesive copolymer is a urethane dimethacrylate-methyl methacrylate copolymer that comprises a plurality of first polymer regions based on urethane dimethacrylate and a plurality of second polymer regions based on methyl methacrylate.

15. The method of claim 14, wherein the mixture further comprises an accelerator and an inhibitor.

16. The method of claim 14, wherein the initiator comprises a free-radical initiator.

17. The method of claim 14, wherein the free-radical initiator comprises a photoinitiator, a thermal initiator, or both.

18. The method of claim 17, wherein the initiator comprises a photoinitiator, and wherein the method comprises projecting light onto the photoinitiator thereby activating the photoinitiator and copolymerize the first non-urethane-containing precursor with the second urethane-containing precursor to form the adhesive copolymer.

19. The method of claim 18, wherein projecting light includes projecting a blue light, a UV light or a broad spectrum light.

20. The method of claim 18, wherein the polymeric implant includes a semi-transparent material, and projecting light includes projecting light through at least a portion of the semi-transparent material.

* * * * *